United States Patent
Sugimoto et al.

(10) Patent No.: US 10,548,899 B2
(45) Date of Patent: Feb. 4, 2020

(54) QUINAZOLINONE AND BENZOTRIAZINONE COMPOUNDS WITH CHOLINERGIC MUSCARININ M1 RECEPTOR POSITIVE ALLOSTERIC MODULATOR ACTIVITY

(71) Applicant: TAKEDA PHARMACEUTICAL COMPANY LIMITED, Osaka-shi, Osaka (JP)

(72) Inventors: Takahiro Sugimoto, Kanagawa (JP); Shinkichi Suzuki, Kanagawa (JP); Hiroki Sakamoto, Kanagawa (JP); Masami Yamada, Kanagawa (JP); Minoru Nakamura, Kanagawa (JP); Makoto Kamata, Kanagawa (JP); Kenichiro Shimokawa, Kanagawa (JP); Masaki Ogino, Kanagawa (JP); Eiji Kimura, Kanagawa (JP); Masataka Murakami, Kanagawa (JP); Takuto Kojima, Kanagawa (JP); Jinichi Yonemori, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 15/769,295

(22) PCT Filed: Oct. 19, 2016

(86) PCT No.: PCT/JP2016/081016
§ 371 (c)(1),
(2) Date: Apr. 18, 2018

(87) PCT Pub. No.: WO2017/069173
PCT Pub. Date: Apr. 27, 2017

(65) Prior Publication Data
US 2018/0303841 A1    Oct. 25, 2018

(30) Foreign Application Priority Data
Oct. 20, 2015   (JP) ................................ 2015-206780

(51) Int. Cl.
| | |
|---|---|
| *A61K 31/53* | (2006.01) |
| *A61K 31/517* | (2006.01) |
| *C07D 403/06* | (2006.01) |
| *C07D 403/10* | (2006.01) |
| *C07D 405/14* | (2006.01) |
| *C07D 401/14* | (2006.01) |
| *C07D 239/88* | (2006.01) |
| *C07D 401/06* | (2006.01) |

(Continued)

(52) U.S. Cl.
CPC ............ *A61K 31/53* (2013.01); *A61K 31/517* (2013.01); *A61P 25/04* (2018.01); *A61P 25/16* (2018.01); *A61P 25/18* (2018.01); *A61P 25/28* (2018.01); *C07D 239/88* (2013.01); *C07D 401/06* (2013.01); *C07D 401/14* (2013.01); *C07D 403/06* (2013.01); *C07D 403/10* (2013.01); *C07D 405/14* (2013.01)

(58) Field of Classification Search
CPC .. C07D 239/88; C07D 401/06; C07D 401/14; C07D 403/06; C07D 403/10; C07D 405/14
See application file for complete search history.

(56) References Cited

U.S. PATENT DOCUMENTS

| | | | |
|---|---|---|---|
| 5,486,512 | A | 1/1996 | Gregor |
| 5,538,983 | A | 7/1996 | Buxbaum et al. |

(Continued)

FOREIGN PATENT DOCUMENTS

| | | |
|---|---|---|
| JP | 2001-131173 | 5/2001 |
| WO | 94/00448 | 1/1994 |

(Continued)

OTHER PUBLICATIONS

Mistry et al. (Chem. Neurosci. 2016, 7, 647-661—PD Feb. 18, 2016).*

(Continued)

*Primary Examiner* — Valerie Rodriguez-Garcia
(74) *Attorney, Agent, or Firm* — Hamre, Schumann, Mueller & Larson, P.C.

(57) ABSTRACT

The present invention provides a compound which has a cholinergic muscarinic M1 receptor positive allosteric modulator activity and may be useful as a medicament such as an agent for the prophylaxis or treatment of Alzheimer's disease, schizophrenia, pain, sleep disorder, Parkinson's disease dementia, Lewy body dementia and the like. The present invention relates to a compound represented by the formula (I) or a salt thereof. In the formula (I), each symbol is as described in the attached specification.

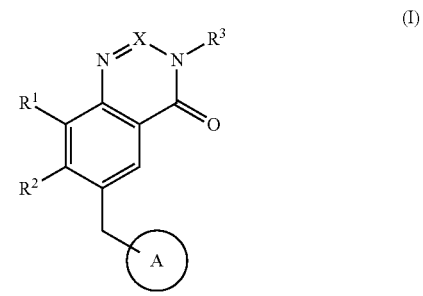

(I)

11 Claims, No Drawings

(51) Int. Cl.
*A61P 25/28* (2006.01)
*A61P 25/04* (2006.01)
*A61P 25/18* (2006.01)
*A61P 25/16* (2006.01)

(56) References Cited

U.S. PATENT DOCUMENTS

| | | | |
|---|---|---|---|
| 5,744,476 | A | 4/1998 | Locke et al. |
| 6,569,897 | B1 | 5/2003 | Cushman et al. |
| 7,678,363 | B2 | 3/2010 | Barlow et al. |
| 9,315,458 | B2 | 4/2016 | Yamada et al. |
| 9,403,802 | B2 | 8/2016 | Sakamoto et al. |
| 9,499,516 | B2 | 11/2016 | Yamada et al. |
| 9,518,042 | B2 | 12/2016 | Yamada et al. |
| 9,549,928 | B2 | 1/2017 | Messer et al. |
| 2003/0220315 | A1 | 11/2003 | Cushman et al. |
| 2004/0023951 | A1 | 2/2004 | Bymaster et al. |
| 2004/0044023 | A1 | 3/2004 | Cantillon |
| 2004/0102450 | A1 | 5/2004 | Ewing et al. |
| 2004/0266659 | A1 | 12/2004 | LaBerge |
| 2006/0009414 | A1 | 1/2006 | Frey, II et al. |
| 2006/0233843 | A1 | 10/2006 | Conn et al. |
| 2007/0049576 | A1 | 3/2007 | Barlow et al. |
| 2009/0082342 | A1 | 3/2009 | Uldam et al. |
| 2009/0082388 | A1 | 3/2009 | Hacksell et al. |
| 2009/0124604 | A1 | 5/2009 | Nash et al. |
| 2009/0124609 | A1 | 5/2009 | Albrecht et al. |
| 2009/0318436 | A1 | 12/2009 | Albrecht et al. |
| 2010/0120842 | A1 | 5/2010 | Barlow et al. |
| 2010/0152169 | A1 | 6/2010 | Nash et al. |
| 2010/0256120 | A1* | 10/2010 | Brown ............ C07D 239/91 514/218 |
| 2011/0020423 | A1 | 1/2011 | Elenko et al. |
| 2011/0224198 | A1* | 9/2011 | Kuduk ............ C07D 239/88 514/228.2 |
| 2011/0319386 | A1 | 12/2011 | Barlow et al. |
| 2012/0046273 | A1 | 2/2012 | Twose et al. |
| 2012/0129877 | A1 | 5/2012 | Martinez Gil et al. |
| 2013/0116272 | A1 | 5/2013 | Kuduk et al. |
| 2013/0184298 | A1 | 7/2013 | Kuduk et al. |
| 2013/0289019 | A1 | 10/2013 | Chau |
| 2014/0088119 | A1 | 3/2014 | Messer et al. |
| 2014/0099356 | A1 | 4/2014 | Elenko et al. |
| 2014/0349976 | A1 | 11/2014 | Hacksell et al. |
| 2015/0126487 | A1 | 5/2015 | Sakamoto et al. |
| 2015/0265593 | A1 | 9/2015 | Elenko et al. |
| 2015/0307451 | A1 | 10/2015 | Yamada et al. |
| 2015/0307497 | A1 | 10/2015 | Sugimoto |
| 2016/0152598 | A1 | 6/2016 | Yamada et al. |
| 2016/0152603 | A1 | 6/2016 | Yamada et al. |
| 2017/0081332 | A1 | 3/2017 | Sugimoto et al. |
| 2017/0095465 | A1 | 4/2017 | Elenko et al. |
| 2017/0112820 | A1 | 4/2017 | Elenko et al. |
| 2017/0121308 | A1 | 5/2017 | Ogino et al. |
| 2018/0250270 | A1 | 9/2018 | Chase et al. |

FOREIGN PATENT DOCUMENTS

| | | |
|---|---|---|
| WO | 96/00062 | 1/1996 |
| WO | 98/30243 | 7/1998 |
| WO | 99/36384 | 7/1999 |
| WO | 99/37304 | 7/1999 |
| WO | 00/32590 | 6/2000 |
| WO | 01/07436 | 2/2001 |
| WO | 01/46192 | 6/2001 |
| WO | 02/03684 | 1/2002 |
| WO | 02/074293 | 9/2002 |
| WO | 03/045315 | 6/2003 |
| WO | 2004/073639 | 9/2004 |
| WO | 2004/087158 | 10/2004 |
| WO | 2006/090143 | 8/2006 |
| WO | 2006/113485 | 10/2006 |
| WO | 2007/020411 | 2/2007 |
| WO | 2007/025177 | 3/2007 |
| WO | 2007/044937 | 4/2007 |
| WO | 2007/075567 | 7/2007 |
| WO | 2007/125287 | 11/2007 |
| WO | 2007/125290 | 11/2007 |
| WO | 2007/125293 | 11/2007 |
| WO | 2008/008539 | 1/2008 |
| WO | 2008/036843 | 3/2008 |
| WO | 2008/113072 | 9/2008 |
| WO | 2009/032116 | 3/2009 |
| WO | 2009/032124 | 3/2009 |
| WO | 2009/032125 | 3/2009 |
| WO | 2009/039460 | 3/2009 |
| WO | 2009/064848 | 5/2009 |
| WO | 2009/064852 | 5/2009 |
| WO | 2009/091374 | 7/2009 |
| WO | 2010/042603 | 4/2010 |
| WO | 2010/059773 | 5/2010 |
| WO | 2010/096338 | 8/2010 |
| WO | 2010/102218 | 9/2010 |
| WO | 2010/123716 | 10/2010 |
| WO | 2011/011060 | 1/2011 |
| WO | 2011-025851 | 3/2011 |
| WO | 2011/049731 | 4/2011 |
| WO | 2011/075371 | 6/2011 |
| WO | 2011/084371 | 7/2011 |
| WO | 2011/159553 | 12/2011 |
| WO | 2012/003147 | 1/2012 |
| WO | 2012/047702 | 4/2012 |
| WO | 2012/149524 | 11/2012 |
| WO | 2012/170599 | 12/2012 |
| WO | 2013/129622 | 9/2013 |
| WO | 2013/142236 | 9/2013 |
| WO | 2014/077401 | 5/2014 |
| WO | 2014/102233 | 7/2014 |
| WO | 2014/117920 | 8/2014 |
| WO | 2014/176460 | 10/2014 |
| WO | 2014/182695 | 11/2014 |
| WO | 2015/163485 | 10/2015 |
| WO | 2015/174534 | 11/2015 |
| WO | 2015/190564 | 12/2015 |
| WO | 2016/208775 | 12/2016 |
| WO | 2017/044693 | 3/2017 |
| WO | 2017/155050 | 9/2017 |
| WO | 2018/122845 | 7/2018 |

OTHER PUBLICATIONS

Patani, et al., "Bioisosterism: A Rational Approach in Drug Design", Chem. Rev. 1996, 96, 3147-3176.

Wess, Jurgen et al. Muscarinic acetylcholine receptors: mutant mice provide new insights for drug development. Nature Reviews Drug Discovery. vol. 6, Sep. 2007, pp. 721-733.

International Search Report issued for PCT/JP2016/069189, dated Oct. 6, 2016, 5 pages.

Kuduk, Scott D. et al. Novel M1 allosteric ligands: a patent review, Expert Opinion on Therapeutic Patents, vol. 22, No. 12, Oct. 23, 2012, pp. 1385-1398. Online [retrieved on Sep. 22, 2016] retrieved at: <http://www.tandfonline.com/loi/ietp20>, 15 pages.

Adbul-Ridha, et al., "Mechanistic Insights into Allosteric Structure-Function Relationships at the M1 Muscarinic Acetylcholine Receptor", The Journal of Biological Chemistry, vol. 289, No. 48, pp. 33701-33711, Nov. 28, 2014.

Mistry, et al., "Novel Fused Arylpyrimidinone Based Allosteric Modulators of the M1 Muscarinic Acetylcholine Receptor", ACS Chemical Neuroscience, 2016, vol. 7, No. 5, pp. 647-661.

Reddy, et al., "Synthesis of 6,6'-methylenebisquinazolinones and 7,7'-methylenebis-1,4-benzodiazephine-2,5-diones", Indian Journal of Chemistry, Section B: Organic Chemistry Including Medicinal Chemistry, vol. 41B(11), Nov. 2002, pp. 2405-2409.

Compound of CAS Registry No. 1497582-45-2, Dec. 18, 2013.

International Search Report issued in related International Application No. PCT/JP2016/081016, dated Jan. 17, 2017, 4 pages.

* cited by examiner

QUINAZOLINONE AND BENZOTRIAZINONE COMPOUNDS WITH CHOLINERGIC MUSCARININ M1 RECEPTOR POSITIVE ALLOSTERIC MODULATOR ACTIVITY

TECHNICAL FIELD

The present invention relates to a heterocyclic compound which has a cholinergic muscarinic M1 receptor positive allosteric modulator activity and may be useful as a medicament such as an agent for the prophylaxis or treatment of Alzheimer's disease, schizophrenia, pain, sleep disorder, Parkinson's disease dementia, Lewy body dementia and the like. As used herein, the positive allosteric modulator activity refers to an action to potentiate receptor function by binding at a different site from that of an endogenous activator (acetylcholine for this receptor).

BACKGROUND OF THE INVENTION

Acetylcholine is a neurotransmitter that induces signal transduction in the central nervous system and the neuromuscular connections (the parasympathetic nerve and motor nerve). In the central nervous system, nuclei of origin of the acetylcholine neuron are in the brain stem and forebrain, and those acetylcholine neurons project to cerebral cortex, hippocampus, and limbic area. In addition, some interneurons in some brain areas such as striatum utilize acetylcholine as a neurotransmitter. Acetylcholine receptor is classified into a ligand dependent-ion channel (cholinergic nicotinic receptor) and a G-protein-coupled receptor (cholinergic muscarinic receptor). The cholinergic muscarinic receptor is one kind of receptor for excitatory neurotransmitter, acetylcholine, and was named based on the selective activation of the receptor by muscarine. The muscarinic receptor is further classified into subtypes of M1 to M5. The M1 receptor is known to be mainly distributed in the brain, and deeply involved particularly in learning, memory, sleep, neuropathic pain, and the like. The importance of cholinergic muscarinic M1 receptor in brain physiology is well known, and a compound which enhances M1 receptor function is expected to be useful as an agent for the prophylaxis or treatment of psychiatric diseases, neurodegenerative diseases, memory disorders, pain, sleep disorders, Parkinson's disease dementia, Lewy body dementia and the like (non-patent document 1).

WO 2014/102233 (patent document 1) discloses the following compound which is a COMT inhibitor and useful for the treatment of Parkinson's disease, dementia, depression, schizophrenia and the like.

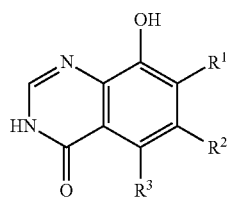

wherein each symbol is as defined in the document.

WO 2007/020411 (patent document 2) discloses the following compound which is a cytokine inhibitor and useful for the treatment of rheumatoid arthritis, asthma, inflammatory bowel disease, multiple sclerosis, AIDS, sepsis shock and the like.

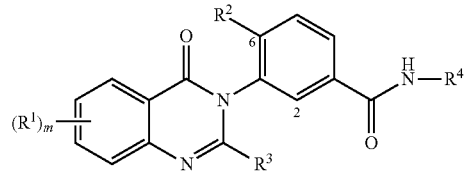

wherein each symbol is as defined in the document.

WO 2006/090143 (patent document 3) discloses the following compound which is a cytokine inhibitor and useful for the treatment of rheumatoid arthritis, asthma, inflammatory bowel disease, multiple sclerosis, AIDS, sepsis shock and the like.

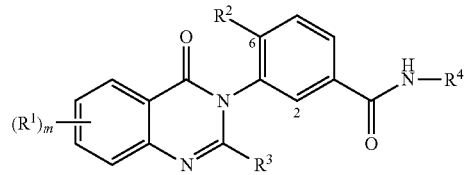

wherein each symbol is as defined in the document.

WO 2001/007436 (patent document 4) discloses the following compound which is an FXa inhibitor and useful for anticoagulation and the treatment of arthritis, Alzheimer's disease and the like.

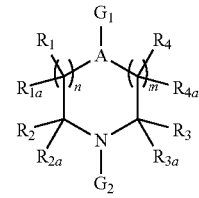

wherein each symbol is as defined in the document.

WO 2000/032590 (patent document 5) discloses the following compound which is an FXa inhibitor and useful for anticoagulation and the treatment of arthritis, Alzheimer's disease and the like.

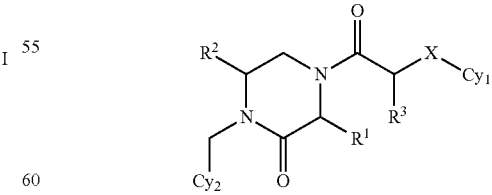

wherein each symbol is as defined in the document.

WO 99/37304 (patent document 6) discloses the following compound which is an FXa inhibitor and useful for anticoagulation and the treatment of arthritis, Alzheimer's disease and the like.

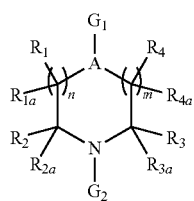

wherein each symbol is as defined in the document.

WO 2013/129622 (patent document 7) discloses the following compound as a compound having a cholinergic muscarinic M1 receptor positive allosteric modulator (M1PAM) activity and useful for the treatment of Alzheimer's disease, schizophrenia, pain, sleep disorder and the like.

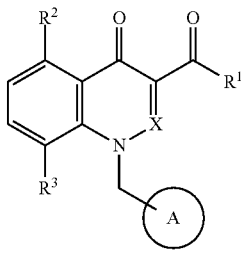

wherein each symbol is as defined in the document.

WO 2014/077401 (patent document 8) discloses the following compound as a compound having an M1PAM activity and useful for the treatment of Alzheimer's disease, schizophrenia, pain, sleep disorder and the like.

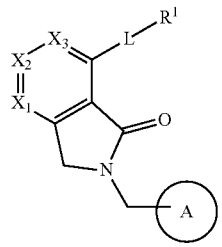

wherein each symbol is as defined in the document.

DOCUMENT LIST

Patent Documents patent document 1: WO 2014/102233
patent document 2: WO 2007/020411
patent document 3: WO 2006/090143
patent document 4: WO 2001/007436
patent document 5: WO 2000/032590
patent document 6: WO 99/37304
patent document 7: WO 2013/129622
patent document 8: WO 2014/077401

Non-Patent Document non-patent document 1: Nature Reviews Drug Discovery, 2007, 6, 721-733.

SUMMARY OF THE INVENTION

Problems to be Solved by the Invention

The development of a compound having a cholinergic muscarinic M1 receptor (M1 receptor) positive allosteric modulator activity and useful as an agent for the prophylaxis or treatment of for Alzheimer's disease, schizophrenia, pain, sleep disorder, Parkinson's disease dementia, Lewy body dementia and the like is desired. As used herein, the positive allosteric modulator activity refers to an action to bind to a site different from endogenous activator (acetylcholine for said receptor) to reinforce the receptor function.

Means of Solving the Problems

The present inventors have conducted intensive studies in an attempt to solve the aforementioned problems and found that a compound represented by the following formula (I) may have a cholinergic muscarinic M1 receptor positive allosteric modulator activity, which resulted in the completion of the present invention.

Accordingly, the present invention relates to the following.

[1] A compound represented by the formula:

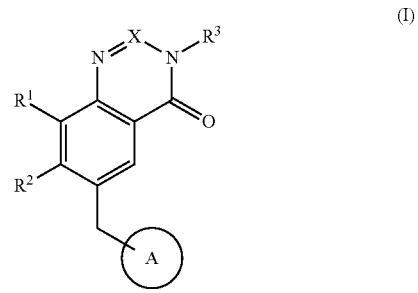

(I)

wherein $R^1$ is a hydrogen atom, a halogen atom, a cyano group, an optionally substituted hydrocarbon group, or a hydroxy group substituted by a hydrocarbon group optionally substituted by a halogen atom;

$R^2$ is a hydrogen atom or a substituent;

$R^3$ is a hydrogen atom, an optionally substituted $C_{1-6}$ alkyl group, an optionally substituted heterocyclic group, an optionally substituted non-aromatic hydrocarbon ring group, or an aromatic hydrocarbon ring group optionally substituted by 1 to 3 substituents selected from (1) a halogen atom, (2) a cyano group and (3) an optionally substituted hydrocarbon group;

ring A is an optionally further substituted 4- to 6-membered monocyclic hydrocarbon ring, an optionally further substituted 5- or 6-membered monocyclic aromatic heterocycle, or a 4- to 6-membered monocyclic non-aromatic heterocycle optionally further substituted by 1 to 3 substituents selected from (1) a cyano group, (2) a halogen atom, (3) an optionally substituted hydroxy group, (4) an optionally substituted heterocyclic group and (5) an optionally substituted hydrocarbon group; and X is CH or N, or a salt thereof (sometimes to be abbreviated as "compound (I)" in the present specification).

[2] The compound described in the aforementioned [1], wherein ring A is an optionally further substituted 4- to

[3] The compound described in the aforementioned [1], wherein $R^1$ is a hydrogen atom, a halogen atom, a $C_{1-6}$ alkyl group or a $C_{1-6}$ alkoxy group;

$R^2$ is a hydrogen atom, a halogen atom, a $C_{1-6}$ alkyl group or a $C_{1-6}$ alkoxy group;

$R^3$ is (1) a hydrogen atom, (2) a $C_{1-6}$ alkyl group optionally substituted by 1 to 3 substituents selected from 3- to 14-membered non-aromatic heterocyclic groups, (3) a 3- to 14-membered non-aromatic heterocyclic group optionally substituted by 1 to 3 hydroxy groups, (4) a 5- to 14-membered aromatic heterocyclic group optionally substituted 1 to 3 cyano groups, (5) a $C_{3-10}$ cycloalkyl group optionally substituted by 1 to 3 hydroxy groups, or (6) a $C_{6-14}$ aryl group optionally substituted by 1 to 3 substituents selected from (a) a halogen atom, and (b) a cyano group;

ring A is (1) a benzene ring optionally further substituted by 1 to 3 substituents selected from (a) a halogen atom, (b) a cyano group, (c) a $C_{1-6}$ alkoxy group optionally substituted by 1 to 5 halogen atoms, and (d) a 5- to 14-membered aromatic heterocyclic group optionally substituted by 1 to 3 $C_{1-6}$ alkyl groups, (2) a 5- or 6-membered monocyclic aromatic heterocycle optionally further substituted by 1 to 3 substituents selected from (a) a halogen atom, (b) a $C_{1-6}$ alkyl group, and (c) a 5- to 14-membered aromatic heterocyclic group optionally substituted by 1 to 3 $C_{1-6}$ alkyl groups, or (3) a 4- to 6-membered monocyclic non-aromatic heterocycle optionally further substituted by 1 to 3 substituents selected from (a) a cyano group, and (b) a 5- to 14-membered aromatic heterocyclic group; and X is CH or N, or a salt thereof.

[4] The compound described in the aforementioned [1], wherein $R^1$ is a hydrogen atom, a halogen atom, a $C_{1-6}$ alkyl group or a $C_{1-6}$ alkoxy group;

$R^2$ is a hydrogen atom, a halogen atom, a $C_{1-6}$ alkyl group or a $C_{1-6}$ alkoxy group;

when one of $R^1$ and $R^2$ is a hydrogen atom, then the other is other than a hydrogen atom;

$R^3$ is (1) a hydrogen atom, (2) a $C_{1-6}$ alkyl group optionally substituted by 1 to 3 substituents selected from 3- to 14-membered non-aromatic heterocyclic groups, (3) a 3- to 14-membered non-aromatic heterocyclic group optionally substituted by 1 to 3 hydroxy groups, (4) a 5- to 14-membered aromatic heterocyclic group optionally substituted 1 to 3 cyano groups, (5) a $C_{3-10}$ cycloalkyl group optionally substituted by 1 to 3 hydroxy groups, or (6) a $C_{6-14}$ aryl group optionally substituted by 1 to 3 substituents selected from (a) a halogen atom, and (b) a cyano group;

ring A is (1) a benzene ring optionally further substituted by 1 to 3 substituents selected from (a) a halogen atom, (b) a cyano group, (c) a $C_{1-6}$ alkoxy group optionally substituted by 1 to 5 halogen atoms, and (d) a 5- to 14-membered aromatic heterocyclic group optionally substituted by 1 to 3 $C_{1-6}$ alkyl groups, (2) a 5- or 6-membered monocyclic aromatic heterocycle optionally further substituted by 1 to 3 substituents selected from (a) a halogen atom, (b) a $C_{1-6}$ alkyl group, and (c) a 5- to 14-membered aromatic heterocyclic group optionally substituted by 1 to 3 $C_{1-6}$ alkyl groups, or (3) a 4- to 6-membered monocyclic non-aromatic heterocycle optionally further substituted by 1 to 3 substituents selected from (a) a cyano group, and (b) a 5- to 14-membered aromatic heterocyclic group; and X is CH or N, or a salt thereof.

[5] The compound described in the aforementioned [1], wherein $R^1$ is a hydrogen atom, a halogen atom or a $C_{1-6}$ alkyl group;

$R^2$ is a $C_{1-6}$ alkyl group;

$R^3$ is (1) a $C_{1-6}$ alkyl group optionally substituted by 1 to 3 substituents selected from 3- to 14-membered non-aromatic heterocyclic groups, (2) a 3- to 14-membered non-aromatic heterocyclic group optionally substituted by 1 to 3 hydroxy groups, or (3) a $C_{3-10}$ cycloalkyl group optionally substituted by 1 to 3 hydroxy groups;

ring A is (1) a benzene ring optionally further substituted by 1 to 3, 5- to 14-membered aromatic heterocyclic groups optionally substituted by 1 to 3 $C_{1-6}$ alkyl groups, (2) a 5- or 6-membered monocyclic aromatic heterocycle optionally further substituted by 1 to 3 substituents selected from (a) a halogen atom, and (b) a 5- to 14-membered aromatic heterocyclic group optionally substituted by 1 to 3 $C_{1-6}$ alkyl groups, or (3) a 4- to 6-membered monocyclic non-aromatic heterocycle optionally further substituted by 1 to 3 substituents selected from (a) a cyano group, and (b) a 5- to 14-membered aromatic heterocyclic group; and X is CH or N, or a salt thereof.

[6] The compound described in the aforementioned [1], wherein $R^1$ is a halogen atom or a $C_{1-6}$ alkyl group;

$R^2$ is a $C_{1-6}$ alkyl group;

$R^3$ is (1) a 3- to 14-membered non-aromatic heterocyclic group optionally substituted by 1 to 3 hydroxy groups, or (2) a $C_{3-10}$ cycloalkyl group optionally substituted by 1 to 3 hydroxy groups;

ring A is (1) a benzene ring optionally further substituted by 1 to 3, 5- to 14-membered aromatic heterocyclic groups optionally substituted by 1 to 3 $C_{1-6}$ alkyl groups, or (2) a 5- or 6-membered monocyclic aromatic heterocycle optionally further substituted by 1 to 3, 5- to 14-membered aromatic heterocyclic groups optionally substituted by 1 to 3 $C_{1-6}$ alkyl groups; and X is CH or N, or a salt thereof.

[7] 8-Fluoro-3-((3S,4S)-4-hydroxytetrahydro-2H-pyran-3-yl)-7-methyl-6-(4-(1H-pyrazol-1-yl)benzyl)quinazolin-4(3H)-one, or a salt thereof.

[8] 3-((3S,4S)-4-Hydroxytetrahydro-2H-pyran-3-yl)-7,8-dimethyl-6-(4-(1-methyl-1H-pyrazol-3-yl)benzyl)-1,2,3-benzotriazin-4(3H)-one, or a salt thereof.

[9] 3-((1S,2S)-2-Hydroxycyclohexyl)-7,8-dimethyl-6-((6-(1-methyl-1H-pyrazol-4-yl)pyridin-3-yl)methyl)quinazolin-4(3H)-one, or a salt thereof.

[10] A medicament comprising the compound described in the aforementioned [1] or a salt thereof.

[11] The medicament described in the aforementioned [10], which is a cholinergic muscarinic M1 receptor positive allosteric modulator.

[12] The medicament described in the aforementioned [10], which is a prophylactic or therapeutic drug for Alzheimer's disease, schizophrenia, pain, sleep disorder, Parkinson's disease dementia or Lewy body dementia.

[13] The compound described in the aforementioned [1] or a salt thereof, for use in the prophylaxis or treatment of Alzheimer's disease, schizophrenia, pain, sleep disorder, Parkinson's disease dementia or Lewy body dementia.

[14] A method of cholinergic muscarinic M1 receptor positive allosteric modulation in a mammal, which comprises administering an effective amount of the compound described in the aforementioned [1] or a salt thereof to the mammal.

[15] A method for the prophylaxis or treatment of Alzheimer's disease, schizophrenia, pain, sleep disorder, Parkinson's disease dementia or Lewy body dementia in a mammal, which comprises administering an effective amount of the compound described in the aforementioned [1] or a salt thereof to the mammal.

[16] Use of the compound described in the aforementioned [1] or a salt thereof for the production of an agent for the prophylaxis or treatment of Alzheimer's disease, schizophrenia, pain, sleep disorder, Parkinson's disease dementia or Lewy body dementia.

Effect of the Invention

The compound of the present invention may have a cholinergic muscarinic M1 receptor positive allosteric modulator activity, and may be useful as a medicament such as an agent for the prophylaxis or treatment of, for example, Alzheimer's disease, schizophrenia, pain, sleep disorder, Parkinson's disease dementia, Lewy body dementia and the like.

DETAILED DESCRIPTION OF THE INVENTION

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5 halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5 halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5 halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5 halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5 halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5 halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following Substituent Group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,

(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl)($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the above-mentioned Substituent Group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-5}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkyl-phosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent Group A".

Preferable examples of the optionally substituted amino group include an amino group, a mono- or di-(optionally halogenated $C_{1-6}$ alkylamino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl)amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl)amino group (e.g., N-acetyl-N-methylamino) and a ($C_{1-6}$ alkyl) ($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent Group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent Group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent Group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxy group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent Group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from Substituent Group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from Substituent Group A".

Preferable examples of the optionally substituted silyl group include a tri-$C_{1-6}$ alkylsilyl group (e.g., trimethylsilyl, tert-butyl(dimethyl)silyl).

In the present specification, examples of the "hydrocarbocycle" include a $C_{6-14}$ aromatic hydrocarbocycle, $C_{3-10}$ cycloalkane, and $C_{3-10}$ cycloalkene.

In the present specification, examples of the "$C_{6-14}$ aromatic hydrocarbocycle" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "C$_{3-10}$ cycloalkene" include cyclopropene, cyclobutene, cyclopentene, cyclohexene, cycloheptene and cyclooctene.

In the present specification, examples of the "heterocycle" include aromatic heterocycle and non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiine, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxathiine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepanine, diazepane, azepine, azocane, diazocane, oxepane and the like; and 9- to 14-membered fused polycyclic (preferably bi or tricyclic) non-aromatic heterocycles such as dihydrobenzofuran, dihydrobenzoimidazole, dihydrobenzooxazole, dihydrobenzothiazole, dihydrobenzoisothiazole, dihydronaphto[2,3-b]thiophene, tetrahydroisoquinoline, tetrahydroquinoline, 4H-quinolizine, indoline, isoindoline, tetrahydrothieno[2,3-c]pyridine, tetrahydrobenzoazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring-constituting atom.

Each symbol in the formula (I) is explained below.

R$^1$ is a hydrogen atom, a halogen atom, a cyano group, an optionally substituted hydrocarbon group, or a hydroxy group substituted by a hydrocarbon group optionally substituted by a halogen atom.

As the "optionally substituted hydrocarbon group" for R$^1$, a C$_{1-6}$ alkyl group is preferable.

As the "hydroxy group substituted by a hydrocarbon group optionally substituted by a halogen atom" for R$^1$, a C$_{1-6}$ alkoxy group optionally substituted by 1 to 5 halogen atoms is preferable.

R$^1$ is preferably a hydrogen atom, a halogen atom (e.g., chlorine atom, fluorine atom), a C$_{1-6}$ alkyl group (e.g., methyl) or a C$_{1-6}$ alkoxy group (e.g., methoxy). R$^1$ is more preferably a hydrogen atom, a halogen atom (e.g., fluorine atom) or a C$_{1-6}$ alkyl group (e.g., methyl). R$^1$ is further preferably a halogen atom (e.g., fluorine atom) or a C$_{1-6}$ alkyl group (e.g., methyl). Among others, a C$_{1-6}$ alkyl group (e.g., methyl) is preferable.

R$^2$ is a hydrogen atom or a substituent.

As the "substituent" for R$^2$, a halogen atom, a cyano group, an optionally substituted hydrocarbon group, or a hydroxy group substituted by a hydrocarbon group optionally substituted by a halogen atom is preferable.

As the "optionally substituted hydrocarbon group" for R$^2$, a C$_{1-6}$ alkyl group is preferable.

As the "hydroxy group substituted by a hydrocarbon group optionally substituted by a halogen atom" for R$^2$, a C$_{1-6}$ alkoxy group optionally substituted by 1 to 5 halogen atoms is preferable.

R$^2$ is preferably a hydrogen atom, a halogen atom (e.g., chlorine atom), a C$_{1-6}$ alkyl group (e.g., methyl) or a C$_{1-6}$ alkoxy group (e.g., methoxy). R$^2$ is more preferably a C$_{1-6}$ alkyl group (e.g., methyl).

In a preferable embodiment of the present invention, when one of R$^1$ and R$^2$ is a hydrogen atom, the other is other than a hydrogen atom.

R$^3$ is a hydrogen atom, an optionally substituted C$_{1-6}$ alkyl group, an optionally substituted heterocyclic group, an optionally substituted non-aromatic hydrocarbon ring group, or an aromatic hydrocarbon ring group optionally substituted by 1 to 3 substituents selected from (1) a halogen atom, (2) a cyano group and (3) an optionally substituted hydrocarbon group.

As the substituent of the "optionally substituted C$_{1-6}$ alkyl group" for R$^3$, 1 to 3 substituents selected from 3- to 14-membered non-aromatic heterocyclic groups (e.g., tetrahydrofuranyl) is/are preferable.

As the "heterocyclic group" of the "optionally substituted heterocyclic group" for R$^3$, a 3- to 14-membered non-aromatic heterocyclic group (e.g., tetrahydropyranyl) or a 5- to 14-membered aromatic heterocyclic group (e.g., pyridyl) is preferable. As the substituent thereof, 1 to 3 substituents selected from a cyano group and a hydroxy group is/are preferable.

As the "non-aromatic hydrocarbon ring group" of the "optionally substituted non-aromatic hydrocarbon ring group" for R$^3$, a C$_{3-10}$ cycloalkyl group (e.g., cyclopentyl, cyclohexyl) is preferable. As the substituent thereof, 1 to 3 hydroxy groups are preferable.

As the "aromatic hydrocarbon ring group" of the "aromatic hydrocarbon ring group optionally substituted by 1 to 3 substituents selected from (1) a halogen atom, (2) a cyano group and (3) an optionally substituted hydrocarbon group"

for $R^3$, a $C_{6-14}$ aryl group (e.g., phenyl) is preferable. As the "optionally substituted hydrocarbon group" which is the substituent thereof, a $C_{1-6}$ alkyl group optionally substituted by 1 to 5 halogen atoms, a $C_{2-6}$ alkenyl group, a $C_{2-6}$ alkynyl group, a $C_{3-10}$ cycloalkyl group, a $C_{3-10}$ cycloalkenyl group or a $C_{6-14}$ aryl group is preferable.

$R^3$ is preferably
(1) a hydrogen atom,
(2) a $C_{1-6}$ alkyl group (e.g., methyl) optionally substituted by 1 to 3 substituents selected from 3- to 14-membered non-aromatic heterocyclic groups (e.g., tetrahydrofuranyl),
(3) a 3- to 14-membered non-aromatic heterocyclic group (e.g., tetrahydropyranyl) optionally substituted by 1 to 3 hydroxy groups,
(4) a 5- to 14-membered aromatic heterocyclic group (e.g., pyridyl) optionally substituted 1 to 3 cyano groups,
(5) a $C_{3-10}$ cycloalkyl group (e.g., cyclopentyl, cyclohexyl) optionally substituted by 1 to 3 hydroxy groups, or
(6) a $C_{6-14}$ aryl group (e.g., phenyl) optionally substituted by 1 to 3 substituents selected from
(a) a halogen atom (e.g., fluorine atom), and
(b) a cyano group.

$R^3$ is more preferably
(1) a $C_{1-6}$ alkyl group (e.g., methyl) optionally substituted by 1 to 3 substituents selected from 3- to 14-membered non-aromatic heterocyclic groups (e.g., tetrahydrofuranyl),
(2) a 3- to 14-membered non-aromatic heterocyclic group (e.g., tetrahydropyranyl) optionally substituted by 1 to 3 hydroxy groups, or
(3) a $C_{3-10}$ cycloalkyl group (e.g., cyclopentyl, cyclohexyl) optionally substituted by 1 to 3 hydroxy groups.

$R^3$ is further preferably
(1) a 3- to 14-membered non-aromatic heterocyclic group (e.g., tetrahydropyranyl) optionally substituted by 1 to 3 hydroxy groups, or
(2) a $C_{3-10}$ cycloalkyl group (e.g., cyclopentyl, cyclohexyl) optionally substituted by 1 to 3 hydroxy groups.

In another embodiment, $R^3$ is preferably
(1) a $C_{1-6}$ alkyl group (e.g., methyl) substituted by 1 to 3 substituents selected from 3- to 14-membered non-aromatic heterocyclic groups (e.g., tetrahydrofuranyl),
(2) a 3- to 14-membered non-aromatic heterocyclic group (e.g., tetrahydropyranyl) optionally substituted by 1 to 3 hydroxy groups,
(3) a 5- to 14-membered aromatic heterocyclic group (e.g., pyridyl) optionally substituted 1 to 3 cyano groups, or
(4) a $C_{6-14}$ aryl group (e.g., phenyl) optionally substituted by 1 to 3 substituents selected from (a) a halogen atom (e.g., fluorine atom) and (b) a cyano group.

In another embodiment, $R^3$ is more preferably
(1) a $C_{1-6}$ alkyl group (e.g., methyl) substituted by 1 to 3 substituents selected from 3- to 14-membered non-aromatic heterocyclic groups (e.g., tetrahydrofuranyl), or
(2) a 3- to 14-membered non-aromatic heterocyclic group (e.g., tetrahydropyranyl) optionally substituted by 1 to 3 hydroxy groups.

In another embodiment, $R^3$ is further preferably a 3- to 14-membered non-aromatic heterocyclic group (e.g., tetrahydropyranyl) optionally substituted by 1 to 3 hydroxy groups.

Ring A is an optionally further substituted 4- to 6-membered monocyclic hydrocarbon ring, an optionally further substituted 5- or 6-membered monocyclic aromatic heterocycle, or a 4- to 6-membered monocyclic non-aromatic heterocycle optionally further substituted by 1 to 3 substituents selected from (1) a cyano group, (2) a halogen atom, (3) an optionally substituted hydroxy group, (4) an optionally substituted heterocyclic group and (5) an optionally substituted hydrocarbon group.

Ring A is preferably an optionally further substituted 4- to 6-membered monocyclic hydrocarbon ring, an optionally further substituted 5- or 6-membered monocyclic aromatic heterocycle, or a 4- to 6-membered monocyclic non-aromatic heterocycle optionally further substituted by 1 to 3 substituents selected from (1) a cyano group, (2) a halogen atom, (3) a substituted hydroxy group, (4) an optionally substituted heterocyclic group and (5) an optionally substituted hydrocarbon group.

Ring A is more preferably an optionally further substituted 4- to 6-membered monocyclic hydrocarbon ring or an optionally further substituted 5- or 6-membered monocyclic aromatic heterocycle.

As the "4- to 6-membered monocyclic hydrocarbon ring" of the "optionally further substituted 4- to 6-membered monocyclic hydrocarbon ring" for ring A, a benzene ring, a $C_{4-6}$ cycloalkane ring (e.g., cyclobutane ring, cyclopentane ring, cyclohexane ring) or a $C_{4-6}$ cycloalkene ring (e.g., cyclobutene ring, cyclopentene ring, cyclohexene ring) can be mentioned. As the "4- to 6-membered monocyclic hydrocarbon ring", a benzene ring can be preferably mentioned.

As the substituent of the "optionally further substituted 4- to 6-membered monocyclic hydrocarbon ring" for ring A, 1 to 3 substituents selected from (1) a cyano group, (2) a halogen atom, (3) an optionally substituted hydroxy group, (4) an optionally substituted heterocyclic group and (5) an optionally substituted hydrocarbon group can be mentioned.

As the "5- or 6-membered monocyclic aromatic heterocycle" of the "optionally further substituted 5- or 6-membered monocyclic aromatic heterocycle" for ring A, a 5- or 6-membered monocyclic aromatic heterocycle (e.g., thiophene ring, furan ring, pyrrole ring, imidazole ring, pyrazole ring, thiazole ring, isothiazole ring, oxazole ring, isoxazole ring, pyridine ring, pyrazine ring, pyrimidine ring, pyridazine ring, 1,2,4-oxadiazole ring, 1,3,4-oxadiazole ring, 1,2,4-thiadiazole ring, 1,3,4-thiadiazole ring, triazole ring, tetrazole ring, triazine ring) containing, as a ring-constituting atom besides carbon atom, 1 to 4 hetero atoms selected from nitrogen atom, sulfur atom and oxygen atom can be mentioned. As the "5- or 6-membered monocyclic aromatic heterocycle", a pyridine ring, an isoxazole ring or a pyrazole ring can be preferably mentioned.

As the substituent of the "optionally further substituted 5- or 6-membered monocyclic aromatic heterocycle" for ring A, 1 to 3 substituents selected from (1) a cyano group, (2) a halogen atom, (3) an optionally substituted hydroxy group, (4) an optionally substituted heterocyclic group and (5) an optionally substituted hydrocarbon group can be mentioned.

As the "4- to 6-membered monocyclic non-aromatic heterocycle" of the "4- to 6-membered monocyclic non-aromatic heterocycle optionally further substituted by 1 to 3 substituents selected from (1) a cyano group, (2) a halogen atom, (3) an optionally substituted hydroxy group, (4) an optionally substituted heterocyclic group and (5) an optionally substituted hydrocarbon group" for ring A, a 4- to 6-membered monocyclic non-aromatic heterocycle (e.g., azetidine ring, oxetane ring, thietane ring, tetrahydrothiophene ring, tetrahydrofuran ring, pyrroline ring, pyrrolidine ring, imidazoline ring, imidazolidine ring, oxazoline ring, oxazolidine ring, pyrazoline ring, pyrazolidine ring, thiazoline ring, thiazolidine ring, tetrahydroisothiazole ring, tetrahydroisoxazole ring, piperidine ring, piperazine ring, tetrahydropyridine ring, dihydropyridine ring, dihydrothiopyran ring, tetrahydropyrimidine ring, tetrahydropyridazine ring, dihydropyran ring, tetrahydropyran ring, tetrahydrothiopyran ring, morpholine ring, thiomorpholine ring) containing, as a ring-constituting atom besides carbon atom, 1 to 4 hetero atoms selected from nitrogen atom, sulfur atom and oxygen atom can be mentioned. As the "4- to 6-membered monocyclic non-aromatic heterocycle", a piperidine ring can be preferably mentioned.

In ring A, as the "optionally substituted hydroxy group" which is the substituent of the "4- to 6-membered monocyclic non-aromatic heterocycle", a $C_{1-6}$ alkoxy group optionally substituted by 1 to 5 halogen atoms is preferable.

In ring A, as the "substituted hydroxy group" which is the substituent of the "4- to 6-membered monocyclic non-aromatic heterocycle", a $C_{1-6}$ alkoxy group optionally substituted by 1 to 5 halogen atoms is preferable.

In ring A, as the "optionally substituted heterocyclic group" which is the substituent of the "4- to 6-membered monocyclic non-aromatic heterocycle", a 5- to 14-membered aromatic heterocyclic group (e.g., pyridyl, triazolyl, pyrazolyl, imidazolyl) optionally substituted by 1 to 3 $C_{1-6}$ alkyl groups is preferable.

In ring A, as the "optionally substituted hydrocarbon group" which is the substituent of the "4- to 6-membered monocyclic non-aromatic heterocycle", a $C_{1-6}$ alkyl group optionally substituted by 1 to 5 halogen atoms is preferable.

Ring A is preferably
(1) a benzene ring optionally further substituted by 1 to 3 substituents selected from
(a) a halogen atom (e.g., fluorine atom),
(b) a cyano group,
(c) a $C_{1-6}$ alkoxy group (e.g., methoxy) optionally substituted by 1 to 5 halogen atoms (e.g., fluorine atom), and
(d) a 5- to 14-membered aromatic heterocyclic group (e.g., pyrazolyl, triazolyl) optionally substituted by 1 to 3 $C_{1-6}$ alkyl groups (e.g., methyl),
(2) a 5- or 6-membered monocyclic aromatic heterocycle (e.g., pyridine ring, isoxazole ring, pyrazole ring) optionally further substituted by 1 to 3 substituents selected from
(a) a halogen atom (e.g., chlorine atom),
(b) a $C_{1-6}$ alkyl group (e.g., methyl), and
(c) a 5- to 14-membered aromatic heterocyclic group (e.g., pyridyl, triazolyl, pyrazolyl, imidazolyl) optionally substituted by 1 to 3 $C_{1-6}$ alkyl groups (e.g., methyl), or
(3) a 4- to 6-membered monocyclic non-aromatic heterocycle (e.g., piperidine ring) optionally further substituted by 1 to 3 substituents selected from
(a) a cyano group, and
(b) a 5- to 14-membered aromatic heterocyclic group (e.g., pyridyl).

Ring A is more preferably
(1) a benzene ring optionally further substituted by 1 to 3, 5- to 14-membered aromatic heterocyclic groups (e.g., pyrazolyl, triazolyl) optionally substituted by 1 to 3 $C_{1-6}$ alkyl groups (e.g., methyl),
(2) a 5- or 6-membered monocyclic aromatic heterocycle (e.g., pyridine ring) optionally further substituted by 1 to 3 substituents selected from
(a) a halogen atom (e.g., chlorine atom), and
(b) a 5- to 14-membered aromatic heterocyclic group (e.g., pyrazolyl) optionally substituted by 1 to 3 $C_{1-6}$ alkyl groups (e.g., methyl), or
(3) a 4- to 6-membered monocyclic non-aromatic heterocycle (e.g., piperidine ring) optionally further substituted by 1 to 3 substituents selected from
(a) a cyano group, and
(b) a 5- to 14-membered aromatic heterocyclic group (e.g., pyridyl).

Ring A is further preferably
(1) a benzene ring optionally further substituted by 1 to 3, 5- to 14-membered aromatic heterocyclic groups (e.g., pyrazolyl) optionally substituted by 1 to 3 $C_{1-6}$ alkyl groups (e.g., methyl), or
(2) a 5- or 6-membered monocyclic aromatic heterocycle (e.g., pyridine ring) optionally further substituted by 1 to 3, 5- to 14-membered aromatic heterocyclic groups (e.g., pyrazolyl) optionally substituted by 1 to 3 $C_{1-6}$ alkyl groups (e.g., methyl).

In another embodiment, ring A is preferably a benzene ring optionally further substituted by 1 to 3 substituents selected from
(a) a halogen atom (e.g., fluorine atom),
(b) a cyano group,
(c) a $C_{1-6}$ alkoxy group (e.g., methoxy) optionally substituted by 1 to 5 halogen atoms (e.g., fluorine atom), and
(d) a 5- to 14-membered aromatic heterocyclic group (e.g., pyrazolyl, triazolyl) optionally substituted by 1 to 3 $C_{1-6}$ alkyl groups (e.g., methyl).

In another embodiment, ring A is more preferably a benzene ring optionally further substituted by 1 to 3, 5- to 14-membered aromatic heterocyclic groups (e.g., pyrazolyl, triazolyl) optionally substituted by 1 to 3 $C_{1-6}$ alkyl groups (e.g., methyl).

In still another embodiment, ring A is preferably
(1) a benzene ring optionally further substituted by 1 to 3 substituents selected from
(a) a halogen atom (e.g., fluorine atom),
(b) a cyano group,
(c) a $C_{1-6}$ alkoxy group (e.g., methoxy) optionally substituted by 1 to 5 halogen atoms (e.g., fluorine atom), and
(d) a 5- to 14-membered aromatic heterocyclic group (e.g., pyrazolyl, triazolyl) optionally substituted by 1 to 3 $C_{1-6}$ alkyl groups (e.g., methyl), or
(2) a 5- or 6-membered monocyclic aromatic heterocycle (e.g., pyridine ring, isoxazole ring, pyrazole ring) optionally further substituted by 1 to 3 substituents selected from
(a) a halogen atom (e.g., chlorine atom),
(b) a $C_{1-6}$ alkyl group (e.g., methyl), and
(c) a 5- to 14-membered aromatic heterocyclic group (e.g., pyridyl, triazolyl, pyrazolyl, imidazolyl) optionally substituted by 1 to 3 $C_{1-6}$ alkyl groups (e.g., methyl).

X is preferably CH or N.
X is more preferably N.
Preferable embodiments of compound (I) include the following compounds.

[Compound I-1]
Compound (I) wherein
$R^1$ is a hydrogen atom, a halogen atom (e.g., chlorine atom, fluorine atom), a $C_{1-6}$ alkyl group (e.g., methyl) or a $C_{1-6}$ alkoxy group (e.g., methoxy);
$R^2$ is a hydrogen atom, a halogen atom (e.g., chlorine atom), a $C_{1-6}$ alkyl group (e.g., methyl) or a $C_{1-6}$ alkoxy group (e.g., methoxy);
$R^3$ is
(1) a hydrogen atom,
(2) a $C_{1-6}$ alkyl group (e.g., methyl) optionally substituted by 1 to 3 substituents selected from 3- to 14-membered non-aromatic heterocyclic groups (e.g., tetrahydrofuranyl),
(3) a 3- to 14-membered non-aromatic heterocyclic group (e.g., tetrahydropyranyl) optionally substituted by 1 to 3 hydroxy groups,
(4) a 5- to 14-membered aromatic heterocyclic group (e.g., pyridyl) optionally substituted 1 to 3 cyano groups,
(5) a $C_{3-10}$ cycloalkyl group (e.g., cyclopentyl, cyclohexyl) optionally substituted by 1 to 3 hydroxy groups, or (6) a $C_{6-14}$ aryl group (e.g., phenyl) optionally substituted by 1 to 3 substituents selected from
(a) a halogen atom (e.g., fluorine atom), and
(b) a cyano group;
ring A is
(1) a benzene ring optionally further substituted by 1 to 3 substituents selected from
(a) a halogen atom (e.g., fluorine atom),
(b) a cyano group,
(c) a $C_{1-6}$ alkoxy group (e.g., methoxy) optionally substituted by 1 to 5 halogen atoms (e.g., fluorine atom), and
(d) a 5- to 14-membered aromatic heterocyclic group (e.g., pyrazolyl, triazolyl) optionally substituted by 1 to 3 $C_{1-6}$ alkyl groups (e.g., methyl),
(2) a 5- or 6-membered monocyclic aromatic heterocycle (e.g., pyridine ring, isoxazole ring, pyrazole ring) optionally further substituted by 1 to 3 substituents selected from
(a) a halogen atom (e.g., chlorine atom),
(b) a $C_{1-6}$ alkyl group (e.g., methyl), and
(c) a 5- to 14-membered aromatic heterocyclic group (e.g., pyridyl, triazolyl, pyrazolyl, imidazolyl) optionally substituted by 1 to 3 $C_{1-6}$ alkyl groups (e.g., methyl), or
(3) a 4- to 6-membered monocyclic non-aromatic heterocycle (e.g., piperidine ring) optionally further substituted by 1 to 3 substituents selected from
(a) a cyano group, and
(b) a 5- to 14-membered aromatic heterocyclic group (e.g., pyridyl); and
X is CH or N.

[Compound I-2]
Compound (I) wherein
$R^1$ is a hydrogen atom, a halogen atom (e.g., chlorine atom, fluorine atom), a $C_{1-6}$ alkyl group (e.g., methyl) or a $C_{1-6}$ alkoxy group (e.g., methoxy);
$R^2$ is a hydrogen atom, a halogen atom (e.g., chlorine atom), a $C_{1-6}$ alkyl group (e.g., methyl) or a $C_{1-6}$ alkoxy group (e.g., methoxy);
$R^3$ is
(1) a hydrogen atom,
(2) a $C_{1-6}$ alkyl group (e.g., methyl) optionally substituted by 1 to 3 substituents selected from 3- to 14-membered non-aromatic heterocyclic groups (e.g., tetrahydrofuranyl),
(3) a 3- to 14-membered non-aromatic heterocyclic group (e.g., tetrahydropyranyl) optionally substituted by 1 to 3 hydroxy groups,
(4) a 5- to 14-membered aromatic heterocyclic group (e.g., pyridyl) optionally substituted 1 to 3 cyano groups,
(5) a $C_{3-10}$ cycloalkyl group (e.g., cyclopentyl, cyclohexyl) optionally substituted by 1 to 3 hydroxy groups, or
(6) a $C_{6-14}$ aryl group (e.g., phenyl) optionally substituted by 1 to 3 substituents selected from
(a) a halogen atom (e.g., fluorine atom), and
(b) a cyano group;
ring A is
(1) a benzene ring optionally further substituted by 1 to 3 substituents selected from
(a) a halogen atom (e.g., fluorine atom),
(b) a cyano group,
(c) a $C_{1-6}$ alkoxy group (e.g., methoxy) optionally substituted by 1 to 5 halogen atoms (e.g., fluorine atom), and
(d) a 5- to 14-membered aromatic heterocyclic group (e.g., pyrazolyl, triazolyl) optionally substituted by 1 to 3 $C_{1-6}$ alkyl groups (e.g., methyl),
(2) a 5- or 6-membered monocyclic aromatic heterocycle (e.g., pyridine ring, isoxazole ring, pyrazole ring) optionally further substituted by 1 to 3 substituents selected from
(a) a halogen atom (e.g., chlorine atom),
(b) a $C_{1-6}$ alkyl group (e.g., methyl), and
(c) a 5- to 14-membered aromatic heterocyclic group (e.g., pyridyl, triazolyl, pyrazolyl, imidazolyl) optionally substituted by 1 to 3 $C_{1-6}$ alkyl groups (e.g., methyl), or
(3) a 4- to 6-membered monocyclic non-aromatic heterocycle (e.g., piperidine ring) optionally further substituted by 1 to 3 substituents selected from
(a) a cyano group, and
(b) a 5- to 14-membered aromatic heterocyclic group (e.g., pyridyl); and
X is CH or N
(provided that when one of $R^1$ and $R^2$ is a hydrogen atom, the other is other than a hydrogen atom).

[Compound I-2-1]
The aforementioned [compound I-2] wherein
$R^3$ is
(1) a $C_{1-6}$ alkyl group (e.g., methyl) substituted by 1 to 3 substituents selected from 3- to 14-membered non-aromatic heterocyclic groups (e.g., tetrahydrofuranyl),
(2) a 3- to 14-membered non-aromatic heterocyclic group (e.g., tetrahydropyranyl) optionally substituted by 1 to 3 hydroxy groups,
(3) a 5- to 14-membered aromatic heterocyclic group (e.g., pyridyl) optionally substituted 1 to 3 cyano groups,
(4) a $C_{3-10}$ cycloalkyl group (e.g., cyclopentyl, cyclohexyl) optionally substituted by 1 to 3 hydroxy groups, or
(5) a $C_{6-14}$ aryl group (e.g., phenyl) optionally substituted by 1 to 3 substituents selected from
(a) a halogen atom (e.g., fluorine atom), and
(b) a cyano group;
ring A is
(1) a benzene ring optionally further substituted by 1 to 3 substituents selected from
(a) a halogen atom (e.g., fluorine atom),
(b) a cyano group,
(c) a $C_{1-6}$ alkoxy group (e.g., methoxy) optionally substituted by 1 to 5 halogen atoms (e.g., fluorine atom), and
(d) a 5- to 14-membered aromatic heterocyclic group (e.g., pyrazolyl, triazolyl) optionally substituted by 1 to 3 $C_{1-6}$ alkyl groups (e.g., methyl), or
(2) a 5- or 6-membered monocyclic aromatic heterocycle (e.g., pyridine ring, isoxazole ring, pyrazole ring) optionally further substituted by 1 to 3 substituents selected from
(a) a halogen atom (e.g., chlorine atom),
(b) a $C_{1-6}$ alkyl group (e.g., methyl), and
(c) a 5- to 14-membered aromatic heterocyclic group (e.g., pyridyl, triazolyl, pyrazolyl, imidazolyl) optionally substituted by 1 to 3 $C_{1-6}$ alkyl groups (e.g., methyl).

[Compound I-2-2]
The aforementioned [compound I-2-1] wherein
ring A is a benzene ring optionally further substituted by 1 to 3 substituents selected from
(a) a halogen atom (e.g., fluorine atom),
(b) a cyano group,
(c) a $C_{1-6}$ alkoxy group (e.g., methoxy) optionally substituted by 1 to 5 halogen atoms (e.g., fluorine atom), and
(d) a 5- to 14-membered aromatic heterocyclic group (e.g., pyrazolyl, triazolyl) optionally substituted by 1 to 3 $C_{1-6}$ alkyl groups (e.g., methyl).

[Compound I-2-3]
The aforementioned [compound I-2-2] wherein
$R^3$ is
(1) a $C_{1-6}$ alkyl group (e.g., methyl) substituted by 1 to 3 substituents selected from 3- to 14-membered non-aromatic heterocyclic groups (e.g., tetrahydropyranyl), (2) a 3- to 14-membered non-aromatic heterocyclic group (e.g., tetrahydropyranyl) optionally substituted by 1 to 3 hydroxy groups,
(3) a 5- to 14-membered aromatic heterocyclic group (e.g., pyridyl) optionally substituted 1 to 3 cyano groups, or
(4) a $C_{6-14}$ aryl group (e.g., phenyl) optionally substituted by 1 to 3 substituents selected from (a) a halogen atom (e.g., fluorine atom) and (b) a cyano group.
[Compound I-2-4]
The aforementioned [compound I-2-3] wherein X is N.
[Compound I-3]
Compound (I) wherein
$R^1$ is a hydrogen atom, a halogen atom (e.g., fluorine atom) or a $C_{1-6}$ alkyl group (e.g., methyl);
$R^2$ is a $C_{1-6}$ alkyl group (e.g., methyl);
$R^3$ is
(1) a $C_{1-6}$ alkyl group (e.g., methyl) optionally substituted by 1 to 3 substituents selected from 3- to 14-membered non-aromatic heterocyclic groups (e.g., tetrahydrofuranyl),
(2) a 3- to 14-membered non-aromatic heterocyclic group (e.g., tetrahydropyranyl) optionally substituted by 1 to 3 hydroxy groups, or
(3) a $C_{3-10}$ cycloalkyl group (e.g., cyclopentyl, cyclohexyl) optionally substituted by 1 to 3 hydroxy groups;
ring A is
(1) a benzene ring optionally further substituted by 1 to 3, 5- to 14-membered aromatic heterocyclic groups (e.g., pyrazolyl, triazolyl) optionally substituted by 1 to 3 $C_{1-6}$ alkyl groups (e.g., methyl),
(2) a 5- or 6-membered monocyclic aromatic heterocycle (e.g., a pyridine ring) optionally further substituted by 1 to 3 substituents selected from
(a) a halogen atom (e.g., chlorine atom), and
(b) a 5- to 14-membered aromatic heterocyclic group (e.g., pyrazolyl) optionally substituted by 1 to 3 $C_{1-6}$ alkyl groups (e.g., methyl), or
(3) a 4- to 6-membered monocyclic non-aromatic heterocycle (e.g., piperidine ring) optionally further substituted by 1 to 3 substituents selected from
(a) a cyano group, and
(b) a 5- to 14-membered aromatic heterocyclic group (e.g., pyridyl); and
X is CH or N.
[Compound I-3-1]
The aforementioned [compound I-3] wherein
$R^3$ is
(1) a $C_{1-6}$ alkyl group (e.g., methyl) substituted by 1 to 3 substituents selected from 3- to 14-membered non-aromatic heterocyclic groups (e.g., tetrahydrofuranyl),
(2) a 3- to 14-membered non-aromatic heterocyclic group (e.g., tetrahydropyranyl) optionally substituted by 1 to 3 hydroxy groups, or
(3) a $C_{3-10}$ cycloalkyl group (e.g., cyclopentyl, cyclohexyl) optionally substituted by 1 to 3 hydroxy groups; and ring A is
(1) a benzene ring optionally further substituted by 1 to 3, 5- to 14-membered aromatic heterocyclic groups (e.g., pyrazolyl, triazolyl) optionally substituted by 1 to 3 $C_{1-6}$ alkyl groups (e.g., methyl), or
(2) a 5- or 6-membered monocyclic aromatic heterocycle (e.g., a pyridine ring) optionally further substituted by 1 to 3 substituents selected from (a) a halogen atom (e.g., chlorine atom), and (b) a 5- to 14-membered aromatic heterocyclic group (e.g., pyrazolyl) optionally substituted by 1 to 3 $C_{1-6}$ alkyl groups (e.g., methyl).

[Compound I-3-2]
The aforementioned [compound I-3-1] wherein
ring A is a benzene ring optionally further substituted by 1 to 3, 5- to 14-membered aromatic heterocyclic groups (e.g., pyrazolyl, triazolyl) optionally substituted by 1 to 3 $C_{1-6}$ alkyl groups (e.g., methyl).
[Compound I-3-3]
The aforementioned [compound I-3-2] wherein
$R^3$ is
(1) a $C_{1-6}$ alkyl group (e.g., methyl) substituted by 1 to 3 substituents selected from 3- to 14-membered non-aromatic heterocyclic groups (e.g., tetrahydrofuranyl), or
(2) a 3- to 14-membered non-aromatic heterocyclic group (e.g., tetrahydropyranyl) optionally substituted by 1 to 3 hydroxy groups.
[Compound I-3-4]
The aforementioned [compound I-3-3] wherein X is N.
[Compound I-4]
Compound (I) wherein
$R^1$ is a $C_{1-6}$ alkyl group (e.g., methyl);
$R^2$ is a $C_{1-6}$ alkyl group (e.g., methyl);
$R^3$ is
(1) a 3- to 14-membered non-aromatic heterocyclic group (e.g., tetrahydropyranyl) optionally substituted by 1 to 3 hydroxy groups, or
(2) a $C_{3-10}$ cycloalkyl group (e.g., cyclopentyl, cyclohexyl) optionally substituted by 1 to 3 hydroxy groups;
ring A is
(1) a benzene ring optionally further substituted by 1 to 3, 5- to 14-membered aromatic heterocyclic groups (e.g., pyrazolyl) optionally substituted by 1 to 3 $C_{1-6}$ alkyl groups (e.g., methyl), or
(2) a 5- or 6-membered monocyclic aromatic heterocycle (e.g., pyridine ring) optionally further substituted by 1 to 3, 5- to 14-membered aromatic heterocyclic groups (e.g., pyrazolyl) optionally substituted by 1 to 3 $C_{1-6}$ alkyl groups (e.g., methyl); and
X is CH or N.
[Compound I-4-1]
The aforementioned [compound I-4] wherein
$R^1$ is a halogen atom or a $C_{1-6}$ alkyl group (e.g., methyl);
$R^2$ is a $C_{1-6}$ alkyl group (e.g., methyl);
$R^3$ is
(1) a 3- to 14-membered non-aromatic heterocyclic group (e.g., tetrahydropyranyl) optionally substituted by 1 to 3 hydroxy groups, or
(2) a $C_{3-10}$ cycloalkyl group (e.g., cyclopentyl, cyclohexyl) optionally substituted by 1 to 3 hydroxy groups; and
ring A is
(1) a benzene ring optionally further substituted by 1 to 3, 5- to 14-membered aromatic heterocyclic groups (e.g., pyrazolyl) optionally substituted by 1 to 3 $C_{1-6}$ alkyl groups (e.g., methyl), or
(2) a 5- or 6-membered monocyclic aromatic heterocycle (e.g., pyridine ring) optionally further substituted by 1 to 3, 5- to 14-membered aromatic heterocyclic groups (e.g., pyrazolyl) optionally substituted by 1 to 3 $C_{1-6}$ alkyl groups (e.g., methyl).
[Compound I-4-2]
The aforementioned [compound I-4-1] wherein ring A is a benzene ring optionally further substituted by 1 to 3, 5- to 14-membered aromatic heterocyclic groups (e.g., pyrazolyl) optionally substituted by 1 to 3 $C_{1-6}$ alkyl groups (e.g., methyl).
[Compound I-4-3]
The aforementioned [compound I-4-2] wherein
$R^3$ is a 3- to 14-membered non-aromatic heterocyclic group (e.g., tetrahydropyranyl) optionally substituted by 1 to 3 hydroxy groups.

[Compound I-4-4]
The aforementioned [compound I-4-3] wherein X is N.
[Compound I-5]
Compound (I) wherein
$R^1$ is a hydrogen atom, a halogen atom (e.g., fluorine atom), a $C_{1-6}$ alkyl group (e.g., methyl) or a $C_{1-6}$ alkoxy group (e.g., methoxy);
$R^2$ is a hydrogen atom, a halogen atom (e.g., chlorine atom), a $C_{1-6}$ alkyl group (e.g., methyl) or a $C_{1-6}$ alkoxy group (e.g., methoxy);
$R^3$ is
(1) a hydrogen atom,
(2) a $C_{1-6}$ alkyl group (e.g., methyl) optionally substituted by 1 to 3 substituents selected from 3- to 14-membered non-aromatic heterocyclic groups (e.g., tetrahydrofuranyl),
(3) a 3- to 14-membered non-aromatic heterocyclic group (e.g., tetrahydropyranyl) optionally substituted by 1 to 3 hydroxy groups,
(4) a 5- to 14-membered aromatic heterocyclic group (e.g., pyridyl) optionally substituted 1 to 3 cyano groups,
(5) a $C_{3-10}$ cycloalkyl group (e.g., cyclopentyl, cyclohexyl) optionally substituted by 1 to 3 hydroxy groups, or
(6) a $C_{6-14}$ aryl group (e.g., phenyl) optionally substituted by 1 to 3 substituents selected from
(a) a halogen atom (e.g., fluorine atom), and
(b) a cyano group;
ring A is a benzene ring optionally further substituted by 1 to 3 substituents selected from
(1) a halogen atom (e.g., fluorine atom),
(2) a cyano group,
(3) a $C_{1-6}$ alkoxy group (e.g., methoxy) optionally substituted by 1 to 5 halogen atoms (e.g., fluorine atom), and (4) a 5- to 14-membered aromatic heterocyclic group (e.g., pyrazolyl, triazolyl) optionally substituted by 1 to 3 $C_{1-6}$ alkyl groups (e.g., methyl); and
X is CH or N.
[Compound I-6]
Compound (I) wherein
$R^1$ is a halogen atom (e.g., chlorine atom), a $C_{1-6}$ alkyl group (e.g., methyl) or a $C_{1-6}$ alkoxy group (e.g., methoxy);
$R^2$ is a $C_{1-6}$ alkyl group (e.g., methyl);
$R^3$ is
(1) a $C_{1-6}$ alkyl group (e.g., methyl) optionally substituted by 1 to 3 substituents selected from 3- to 14-membered non-aromatic heterocyclic groups (e.g., tetrahydrofuranyl), (2) a 3- to 14-membered non-aromatic heterocyclic group (e.g., tetrahydropyranyl) optionally substituted by 1 to 3 hydroxy groups, or
(3) a $C_{3-10}$ cycloalkyl group (e.g., cyclopentyl, cyclohexyl) optionally substituted by 1 to 3 hydroxy groups;
ring A is a 5- or 6-membered monocyclic aromatic heterocycle (e.g., pyridine ring, isoxazole ring, pyrazole ring) optionally further substituted by 1 to 3 substituents selected from
(1) a halogen atom (e.g., chlorine atom),
(2) a $C_{1-6}$ alkyl group (e.g., methyl), and
(3) a 5- to 14-membered aromatic heterocyclic group (e.g., pyridyl, triazolyl, pyrazolyl, imidazolyl) optionally substituted by 1 to 3 $C_{1-6}$ alkyl groups (e.g., methyl); and
X is CH or N.
[Compound I-7]
Compound (I) wherein
$R^1$ is a $C_{1-6}$ alkyl group (e.g., methyl);
$R^2$ is a $C_{1-6}$ alkyl group (e.g., methyl);
$R^3$ is a $C_{3-10}$ cycloalkyl group (e.g., cyclopentyl) optionally substituted by 1 to 3 hydroxy groups;

ring A is a 4- to 6-membered monocyclic non-aromatic heterocycle (e.g., piperidine ring) optionally further substituted by 1 to 3 substituents selected from
(1) a cyano group, and
(2) a 5- to 14-membered aromatic heterocyclic group (e.g., pyridyl); and
X is CH.

Preferable specific examples of the compound represented by the formula (I) include the compounds of Examples 1-28, 30-32 and 34-59.

When compound (I) is in a form of a salt, examples of such salt include salts with inorganic base, an ammonium salt, salts with organic base, salts with inorganic acid, salts with organic acid, salts with basic or acidic amino acid, and the like.

Preferable examples of the salt with inorganic base include alkali metal salts such as sodium salt, potassium salt and the like; alkaline earth metal salts such as calcium salt, magnesium salt, barium salt and the like; an aluminum salt, and the like.

Preferable examples of the salt with organic base include salts with trimethylamine, triethylamine, pyridine, picoline, ethanolamine, diethanolamine, triethanolamine, dicyclohexylamine, N,N'-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

Among these salts, a pharmaceutically acceptable salt is preferable. When a compound has a basic functional group, preferable examples of the pharmaceutically acceptable salt include salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, p-toluenesulfonic acid and the like. In addition, when a compound has an acidic functional group, examples thereof include inorganic salts such as alkali metal salts (e.g., sodium salt, potassium salt etc.), alkaline earth metal salts (e.g., calcium salt, magnesium salt, barium salt etc.) and the like, ammonium salt and the like.

Compound (I) may be a crystal, and both a single crystal and crystal mixtures are encompassed in the compound (I). The crystal can be produced by crystallization by applying a crystallization method known per se.

Compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, stability etc.). The cocrystal and cocrystal salt can be produced by cocrystallization method known per se.

Compound (I) encompasses solvates (e.g., hydrate) and non-solvates within the scope thereof. Compound (I) may be a compound labeled or substituted with an isotope (e.g., $^2H$, $^3H$, $^{11}C$, $^{14}C$, $^{18}F$, $^{35}S$, $^{125}I$). A compound labeled with or substituted by an isotope may be able to be used, for example, as a tracer used for Positron Emission Tomography (PET) (PET tracer), and may be useful in the field of medical diagnosis and the like.

When compound (I) of the present invention has an asymmetric center, isomers such as enantiomer, diastereomer and the like may be present. Such isomers and a mixture thereof are all encompassed within the scope of the present invention. When an isomer is formed due to the conformation or tautomerism, such isomers and a mixture thereof are all encompassed in compound (I) of the present invention.

The production methods of the compound of the present invention are explained below.

The starting materials and reagents used and the compound obtained in each step in the following production methods may be, each in the form of a salt, and examples of such salt include those similar to the salts of the compound of the present invention and the like.

When the compound obtained in each step is a free form, it can be converted to the objective salt according to a method known per se. When the compound obtained in each step is a salt, it can be converted to the free form or the objective other salt according to a method known per se.

The compound obtained in each step can be used directly as the reaction mixture or as a crude product for the next reaction. Alternatively, the compound obtained in each step can be isolated and purified from a reaction mixture according to a method known per se, for example, a separation means such as concentration, crystallization, recrystallization, distillation, solvent extraction, fractional distillation, column chromatography and the like.

When the raw material compound and reagent used in each step are commercially available, the commercially available product can also be used directly.

In the reaction in each step, while the reaction time varies depending on the kind of the reagent and solvent to be used, it is generally 1 min-48 hr, preferably 10 min-8 hr, unless otherwise specified.

In the reaction in each step, while the reaction temperature varies depending on the kind of the reagent and solvent to be used, it is generally −78° C.-300° C., preferably −78° C.-150° C., unless otherwise specified.

In the reaction in each step, while the pressure varies depending on the kind of the reagent and solvent to be used, it is generally 1 atm-20 atm, preferably 1 atm-3 atm, unless otherwise specified.

Microwave synthesizer such as Initiator manufactured by Biotage and the like may be used for the reaction in each step. While the reaction temperature varies depending on the kind of the reagent and solvent to be used, it is generally room temperature-300° C., preferably 50° C.-250° C., unless otherwise specified. While the reaction time varies depending on the kind of the reagent and solvent to be used, it is generally 1 min-48 hr, preferably 1 min-8 hr, unless otherwise specified.

In the reaction in each step, the reagent is used in an amount of 0.5 equivalents-20 equivalents, preferably 0.8 equivalents-5 equivalents, relative to the substrate, unless otherwise specified. When the reagent is used as a catalyst, the reagent is used in an amount of 0.001 equivalents-1 equivalent, preferably 0.01 equivalents-0.2 equivalents, relative to the substrate. When the reagent is used as a reaction solvent, the reagent is used in a solvent amount.

Unless otherwise specified, the reaction in each step is carried out without solvent, or by dissolving or suspending the raw material compound in a suitable solvent. Examples of the solvent include those described in Examples and the following solvents.

alcohols: methanol, ethanol, tert-butyl alcohol, 2-methoxyethanol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane and the like;
amides: N,N-dimethylformamide, N-methylpyrrolidone and the like;
halogenated hydrocarbons: dichloromethane, carbon tetrachloride and the like;
nitriles: acetonitrile and the like;
sulfoxides: dimethyl sulfoxide and the like;
aromatic organic bases: pyridine and the like;
acid anhydrides: acetic anhydride and the like;
organic acids: formic acid, acetic acid, trifluoroacetic acid and the like;
inorganic acids: hydrochloric acid, sulfuric acid and the like;
esters: ethyl acetate and the like;
ketones: acetone, methyl ethyl ketone and the like;
water.

The above-mentioned solvent can be used in a mixture of two or more kinds thereof in an appropriate ratio.

When a base is used for the reaction in each step, examples thereof include those described in Examples and the following bases.
inorganic bases: sodium hydroxide, magnesium hydroxide, sodium carbonate, calcium carbonate, sodium hydrogen carbonate and the like;
organic bases: triethylamine, diethylamine, N,N-diisopropylethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine, 2,2,6,6-tetramethylpiperidine and the like;
metal alkoxides: sodium ethoxide, potassium tert-butoxide and the like;
alkali metal hydrides: sodium hydride and the like;
metal amides: sodium amide, lithium diisopropylamide, lithium hexamethyldisilazide and the like;
organic lithiums: n-butyllithium and the like.

When an acid or an acid catalyst is used for the reaction in each step, examples thereof include those described in Examples and the following acids and acid catalysts. inorganic acids: hydrochloric acid, sulfuric acid, nitric acid, hydrobromic acid, phosphoric acid and the like;
organic acids: acetic acid, trifluoroacetic acid, citric acid, p-toluenesulfonic acid, 10-camphorsulfonic acid and the like; Lewis acid: boron trifluoride diethyl ether complex, zinc iodide, anhydrous aluminum chloride, anhydrous zinc chloride, anhydrous iron chloride and the like.

Unless otherwise specified, the reaction in each step is carried out according to a method known per se, for example, the method described in Jikken Kagaku Kouza, 5th Edition, vol. 13-19 (the Chemical Society of Japan ed.); Shin Jikken Kagaku Kouza, vol. 14-15 (the Chemical Society of Japan ed.); Fine Organic Chemistry, Revised 2nd Edition (L. F. Tietze, Th. Eicher, Nankodo); Organic Name Reactions, the Reaction Mechanism and Essence, Revised Edition (Hideo Togo, Kodansha); ORGANIC SYNTHESES Collective Volume I-VII (John Wiley & Sons Inc); Modern Organic Synthesis in the Laboratory A Collection of Standard Experimental Procedures (Jie Jack Li, OXFORD UNIVERSITY); Comprehensive Heterocyclic Chemistry III, Vol. 1-Vol. 14 (Elsevier Japan); Strategic Applications of Named Reactions in Organic Synthesis (translated by Kiyoshi Tomioka, Kagakudojin); Comprehensive Organic Transformations (VCH Publishers Inc.), 1989, or the like, or the method described in EXAMPLES.

In each step, protection or deprotection reaction of functional groups is performed according to a method known per se, for example, the methods described in Wiley-Interscience, 2007, "Protective Groups in Organic Synthesis, 4th Ed." (Theodora W. Greene, Peter G. M. Wuts); Thieme, 2004, "Protecting Groups 3rd Ed." (P. J. Kocienski) and the like, or the methods described in the Examples.

Examples of the protecting group for hydroxy group of alcohol and the like and phenolic hydroxyl group include ether-type protecting groups such as methoxymethyl ether, benzyl ether, tert-butyldimethylsilyl ether, tetrahydropyranyl ether and the like; carboxylate-type protecting groups such as acetate, benzoate and the like; sulfonate-type protecting groups such as methanesulfonate and the like; carbonate-type protecting groups such as tert-butyl carbonate and the like; and the like.

Examples of the protecting group for a carbonyl group of aldehyde include acetal-type protecting groups such as dimethyl acetal and the like; cyclic acetal-type protecting groups such as 1,3-dioxane and the like; and the like.

Examples of the protecting group for a carbonyl group of ketone include ketal-type protecting groups such as dimethyl ketal and the like; cyclic ketal-type protecting groups such as 1,3-dioxane and the like; oxime-type protecting groups such as O-methyloxime and the like; hydrazone-type protecting groups such as N,N-dimethylhydrazone and the like; and the like.

Examples of the protecting group for carboxy group include ester-type protecting groups such as methyl ester and the like; amide-type protecting groups such as N,N-dimethylamide and the like; and the like.

Examples of the protecting group for thiol include ether-type protecting groups such as benzyl thioether and the like; ester-type protecting groups such as thioacetate, thiocarbonate, thiocarbamate and the like; and the like.

Examples of the protecting group for amino group, and aromatic heterocycle such as imidazole, pyrrole, indole and the like include carbamate-type protecting groups such as benzyl carbamate, tert-butyl carbamate and the like; amide-type protecting groups such as acetamide and the like; alkylamine-type protecting groups such as N-triphenylmethylamine and the like; sulfonamide-type protecting groups such as methanesulfonamide and the like; and the like.

Protecting groups can be removed by a method known per se, for example, methods using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide), reduction methods and the like.

When reduction reaction is carried out in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane tetrahydrofuran complex and the like; Raney nickel; Raney cobalt; hydrogen; formic acid; triethylsilane and the like. When carbon-carbon double bond or triple bond is reduced, a method using a catalyst such as palladium-carbon, Lindlar's catalyst and the like may be employed.

When oxidation reaction is carried out in each step, examples of the oxidizing agent to be used include peroxides such as m-chloroperbenzoic acid (mCPBA), hydrogen peroxide, tert-butyl hydroperoxide and the like; perchlorates such as tetrabutylammonium perchlorate and the like; chlorates such as sodium chlorate and the like; chlorites such as sodium chlorite and the like; periodic acids such as sodium periodate and the like; hypervalent iodine reagents such as iodosylbenzene and the like; reagents containing manganese such as manganese dioxide, potassium permanganate and the like; leads such as lead tetraacetate and the like; reagents containing chromium such as pyridinium chlorochromate (PCC), pyridinium dichromate (PDC), Jones reagent and the like; halogen compounds such as N-bromosuccinimide (NBS) and the like; oxygen; ozone; sulfur trioxide-pyridine complex; osmium tetroxide; selenium dioxide; 2,3-dichloro-5,6-dicyano-1,4-benzoquinone (DDQ) and the like.

When radical cyclization reaction is carried out in each step, examples of the radical initiator to be used include azo compounds such as azobisisobutyronitrile (AIBN) and the like; water-soluble radical initiators such as 4-4'-azobis-4-cyanopentanoic acid (ACPA) and the like; triethylboron in the presence of air or oxygen; benzoyl peroxide and the like. Examples of the radical reagent to be used include tributylstannane, tristrimethylsilylsilane, 1,1,2,2-tetraphenyldisilane, diphenylsilane, samarium iodide and the like.

When Wittig reaction is carried out in each step, examples of the Wittig reagent to be used include alkylidene phosphoranes and the like. The alkylidene phosphoranes can be prepared according to a method known per se, for example, by reacting a phosphonium salt with a strong base.

When Horner-Emmons reaction is carried out in each step, examples of the reagent to be used include phosphonoacetates such as methyl dimethylphosphonoacetate, ethyl diethylphosphonoacetate and the like; and bases such as alkali metal hydrides, organic lithiums and the like.

When Friedel-Crafts reaction is carried out in each step, a combination of a Lewis acid and an acid chloride or a combination of a Lewis acid and an alkylating agent (e.g., an alkyl halide, an alcohol, an olefin etc.) is used as a reagent. Alternatively, an organic acid or an inorganic acid can also be used instead of a Lewis acid, and an acid anhydride such as acetic anhydride and the like can also be used instead of an acid chloride.

When aromatic nucleophilic substitution reaction is carried out in each step, a nucleophile (e.g., an amine, imidazole etc.) and a base (e.g., an organic base etc.) are used as a reagent.

When nucleophilic addition reaction by a carbanion, nucleophilic 1,4-addition reaction (Michael addition reaction) by a carbanion or nucleophilic substitution reaction by a carbanion is carried out in each step, examples of the base to be used for generation of the carbanion include organic lithiums, metal alkoxides, inorganic bases, organic bases and the like.

When Grignard reagent is carried out in each step, examples of the Grignard reagent to be used include arylmagnesium halides such as phenylmagnesium bromide and the like; and alkylmagnesium halides such as methylmagnesium bromide and the like. The Grignard reagent can be prepared according to a method known per se, for example, by reacting an alkyl halide or an aryl halide with a metal magnesium in an ether or tetrahydrofuran as a solvent.

When Knoevenagel condensation reaction is carried out in each step, a compound having an activated methylene group with two electron withdrawing groups (e.g., malonic acid, diethyl malonate, malononitrile etc.) and a base (e.g., an organic base, a metal alkoxide, an inorganic base) are used as a reagent.

When Vilsmeier-Haack reaction is carried out in each step, phosphoryl chloride and an amide derivative (e.g., N,N-dimethylformamide etc.) are used as a reagent.

When azidation reaction of an alcohol, an alkyl halide or a sulfonate ester is carried out in each step, examples of the azidating agent to be used include diphenylphosphorylazide (DPPA), trimethylsilylazide, sodium azide and the like. For example, for the azidation reaction of an alcohol, a method using diphenylphosphorylazide and 1,8-diazabicyclo[5.4.0]undec-7-ene (DBU), a method using trimethylsilylazide and a Lewis acid, and the like are employed.

When reductive amination reaction is carried out in each step, examples of the reducing agent to be used include sodium triacetoxyborohydride, sodium cyanoborohydride, hydrogen, formic acid and the like. When the substrate is an amine compound, examples of the carbonyl compound to be used include paraformaldehyde, aldehydes such as acetaldehyde and the like, and ketones such as cyclohexanone and the like. When the substrate is a carbonyl compound, examples of the amine to be used include ammonia, primary amines such as methylamine and the like; secondary amines such as dimethylamine and the like, and the like.

When Mitsunobu reaction is carried out in each step, an azodicarboxylate ester (e.g., diethyl azodicarboxylate (DEAD), diisopropyl azodicarboxylate (DIAD) etc.) and triphenylphosphine are used as a reagent.

When esterification reaction, amidation reaction or ureation reaction is carried out in each step, examples of the reagent to be used include acyl halides such as acid chlorides, acid bromides and the like; activated carboxylic acids such as acid anhydrides, activated esters, sulfate esters and the like. Examples of the activating agent of the carboxylic acid include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride n-hydrate (DMT-MM) and the like; carbonate ester condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphorate (HATU); sulfuric acid; combinations thereof and the like. When carbodiimide condensing agent is used, an additive such as 1-hydroxybenzotriazole (HOBt), N-hydroxysuccinimide (HOSu), dimethylaminopyridine (DMAP) and the like may be added to the reaction system.

When coupling reaction is carried out in each step, examples of the metal catalyst to be used include palladium compounds such as palladium(II) acetate, tetrakis(triphenylphosphine)palladium (0), dichlorobis(triphenylphosphine)palladium(II), dichlorobis(triethylphosphine)palladium(II), tris(dibenzylideneacetone)dipalladium (0), 1,1'-bis(diphenylphosphino)ferrocene palladium(II) chloride, palladium (II) acetate, bis(triphenylphosphine)palladium(II) chloride and the like; nickel compounds such as tetrakis(triphenylphosphine)nickel(0) and the like; rhodium compounds such as tris(triphenylphosphine)rhodium(III) chloride and the like; cobalt compounds; copper compounds such as copper oxide, copper(I) iodide and the like; platinum compounds and the like. In addition, a base may be added to the reaction system, and examples thereof include inorganic bases and the like.

When a coupling reaction is carried out in each step, examples of the metal catalyst to be used also include bis(tri-tert-butylphosphine)palladium(0). A base may be further added to the reaction system, and examples thereof include inorganic bases and the like.

When thiocarbonylation reaction is carried out in each step, phosphorus pentasulfide is typically used as the thiocarbonylating agent. Alternatively, a reagent having a 1,3,2,4-dithiadiphosphetane-2,4-disulfide structure (e.g., 2,4-bis(4-methoxyphenyl)-1,3,2,4-dithiadiphosphetane-2,4-disulfide (Lawesson's reagent) etc.) can also be used instead of phosphorus pentasulfide.

When Wohl-Ziegler reaction is carried out in each step, examples of the halogenating agent to be used include N-iodosuccinimide, N-bromosuccinimide (NBS), N-chlorosuccinimide (NCS), bromine, sulfuryl chloride and the like. In addition, the reaction can be accelerated by subjecting heat, light, a radical initiator such as benzoyl peroxide, azobisisobutyronitrile and the like to the reaction system.

When halogenation reaction of a hydroxy group is carried out in each step, examples of the halogenating agent to be used include hydrohalic acids and acid halides of inorganic acids, specifically, hydrochloric acid, thionyl chloride, phosphorus oxychloride and the like for chlorination, bromine, 48% hydrobromic acid, phosphorus tribromide and the like for bromination. In addition, a method of producing an alkyl halide by reacting an alcohol with triphenylphosphine and carbon tetrachloride or carbon tetrabromide or the like can be employed. Alternatively, a method of producing an alkyl halide via two step comprising converting an alcohol to the corresponding sulfonate ester, and then reacting the sulfonate ester with lithium bromide, lithium chloride or sodium iodide can also be employed.

When Arbuzov reaction is carried out in each step, examples of the reagent to be used include alkyl halides such as ethyl bromoacetate and the like; and phosphites such as triethyl phosphite, tri(isopropyl) phosphite and the like.

When sulfonate esterification reaction is carried out in each step, examples of the sulfonating agent to be used include methanesulfonyl chloride, p-toluenesulfonyl chloride, methanesulfonic anhydride, p-toluenesulfonic anhydride, N-phenylbis(trifluoromethanesulfonimide) and the like.

When hydrolysis reaction is carried out in each step, an acid or a base is used as a reagent. For acid hydrolysis reaction of t-butyl ester, formic acid, triethylsilane and the like may be added to reductively-trap t-butyl cation which is by-produced.

When dehydration reaction is carried out in each step, examples of the dehydrating agent to be used include sulfuric acid, diphosphorus pentaoxide, phosphorus oxychloride, N,N'-dicyclohexylcarbodiimide, alumina, polyphosphoric acid and the like.

When a pyrimidinone ring formation reaction of anthranilamide is carried out in each step, examples of the reagent to be used include N,N-dimethylformamide dimethyl acetal, formamidine acetate and the like.

When a triazinone ring formation reaction of anthranilamide is carried out in each step, examples of the reagent to be used include sodium nitrite and the like. As the acid to be used, hydrochloric acid and the like can be mentioned.

Compound (I) wherein X is CH, i.e., compound (IA), can be produced by the method shown in the following schemes or a method analogous thereto or the method described in Examples.

Compound (IA) can be produced from compound (1) by the following method.

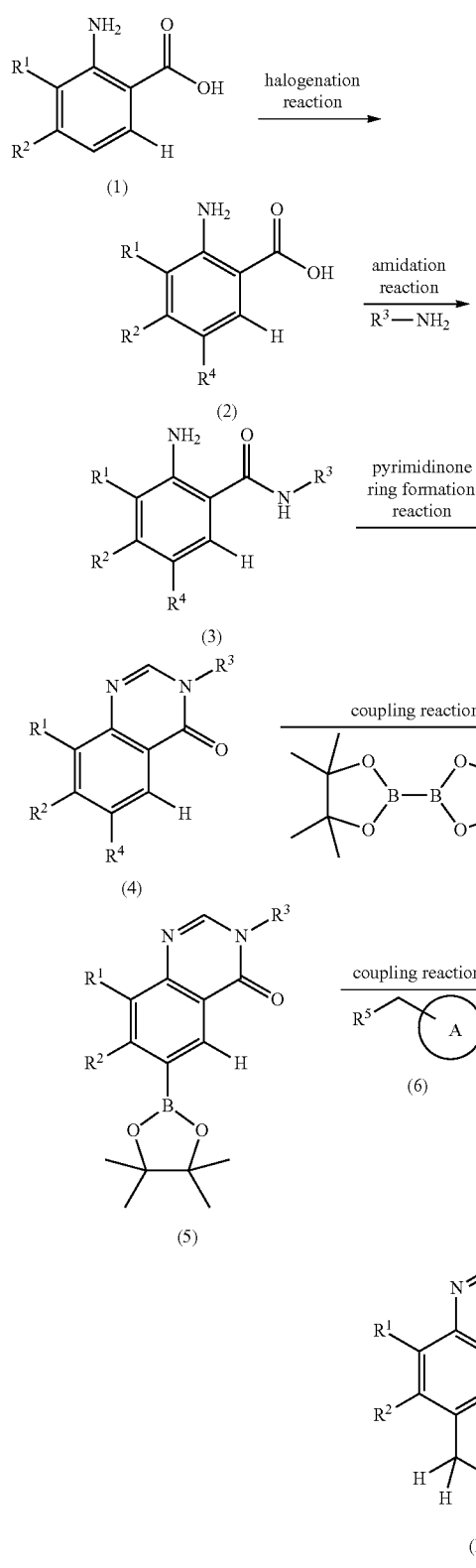

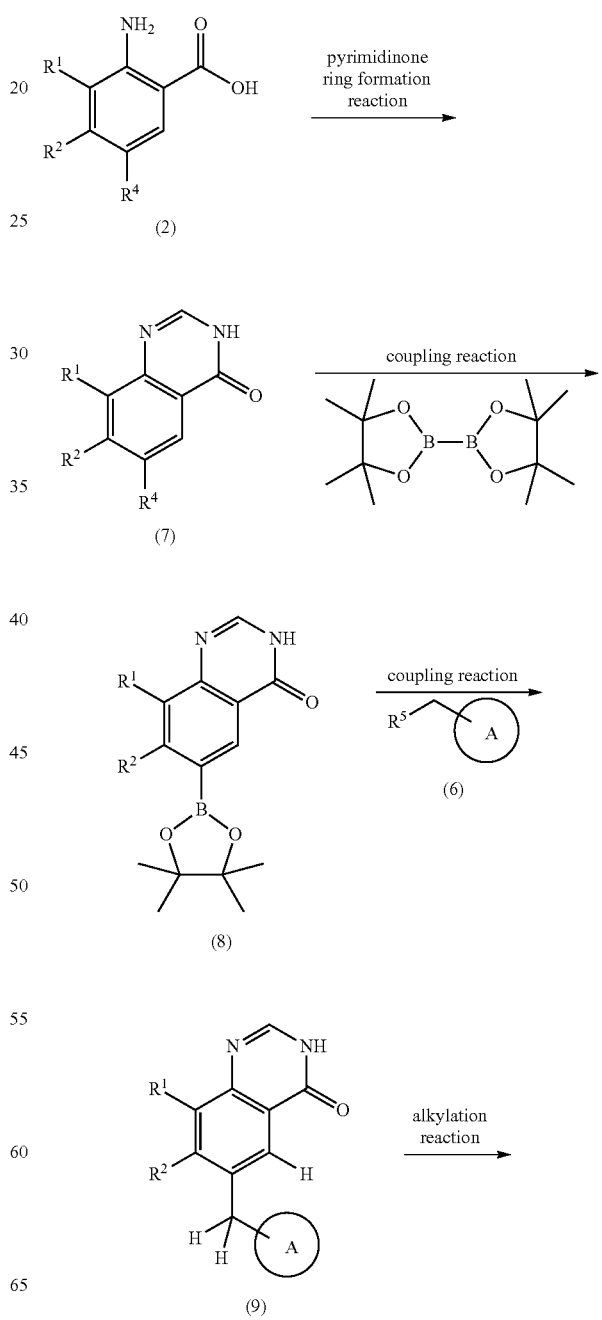

Compound (3) can be produced by an amidation reaction of compound (2) and amines such as $R^3$—$NH_2$ and the like.

Compound (4) can be produced by a pyrimidinone ring formation reaction of compound (3) and N,N-dimethylformamide dimethyl acetal.

Compound (5) can be produced by a coupling reaction of compound (4) and bis(pinacolato)diboron in the presence of a metal catalyst.

Compound (IA) can be produced by a coupling reaction of compound (5) and compound (6) in the presence of a metal catalyst.

Compound (IA) can also be produced from compound (2) by the following method.

In the reaction formulas, $R^4$ and $R^5$ are each a halogen atom and ring A and $R^1$ to $R^3$ mean the same as above.

Compound (2) can be produced by halogenation of compound (1) and a halogenating agent such as bromine and the like.

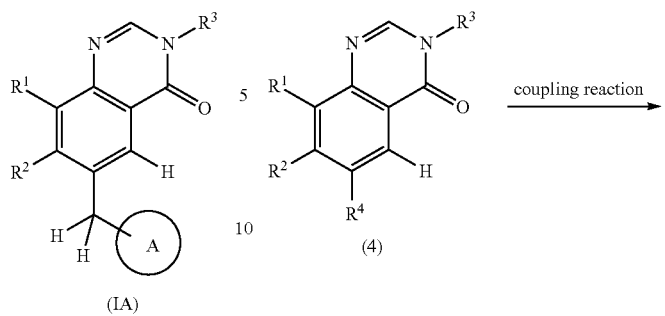

(IA)

In the reaction formulas, ring A and $R^1$ to $R^5$ mean the same as above.

Compound (7) can be produced by a pyrimidinone ring formation reaction of compound (2) and formamidine acetate.

Compound (8) can be produced by a coupling reaction of compound (7) and bis(pinacolato)diboron in the presence of a metal catalyst.

Compound (9) can be produced by a coupling reaction of compound (8) and compound (6) in the presence of a metal catalyst.

Compound (IA) can be produced by an alkylation reaction of compound (9) and alkyl halide.

Compound (IA) can also be produced from compound (4) by the following method.

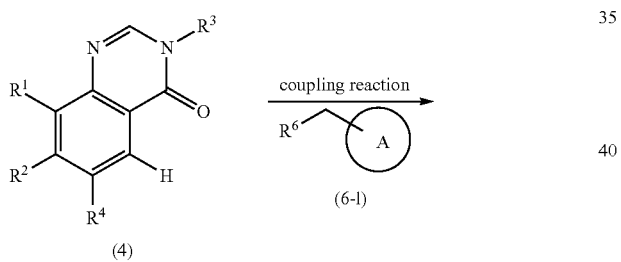

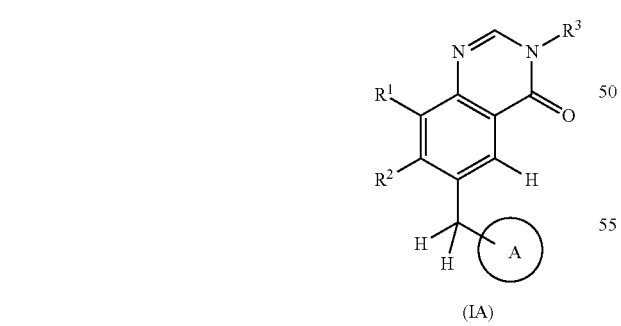

In the reaction formulas, $R^6$ is zinc halide and ring A and $R^1$ to $R^4$ mean the same as above.

Compound (IA) can be produced by a coupling reaction of compound (4) and compound (6-I).

Compound (IA) can also be produced from compound (4) by the following method.

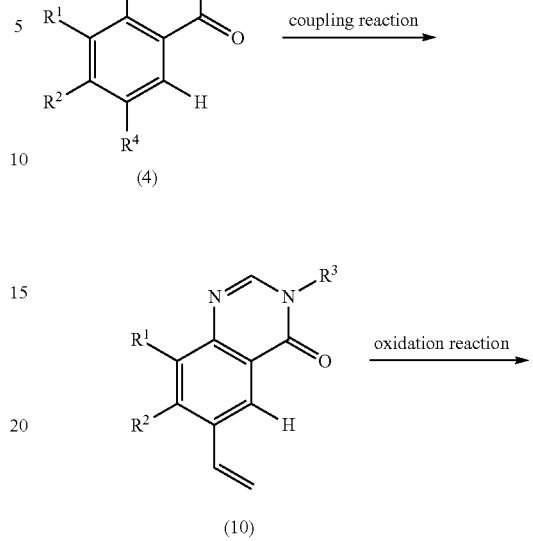

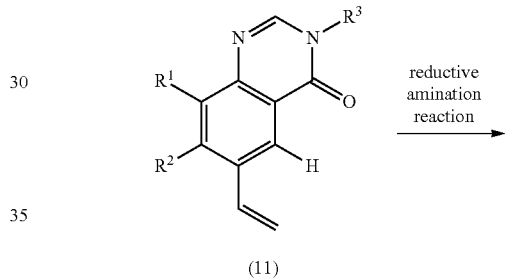

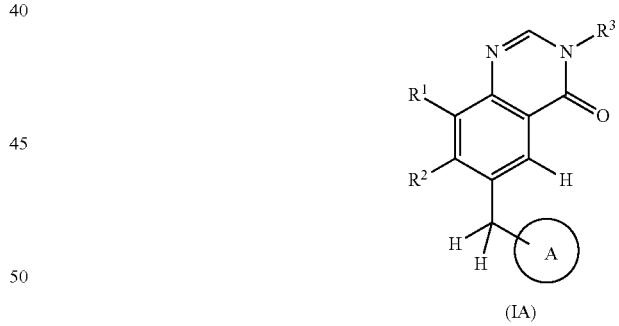

In the reaction formulas, ring A and $R^1$ to $R^4$ mean the same as above.

Compound (10) can be produced by a coupling reaction of compound (4) and vinylboronic acid in the presence of a metal catalyst.

Compound (11) can be produced by an oxidation reaction of compound (10).

Compound (IA) can be produced by a reductive amination reaction using a reducing agent in the presence of compound (11) and amines.

Compound (IA) can also be produced from compound (12) by the following method.

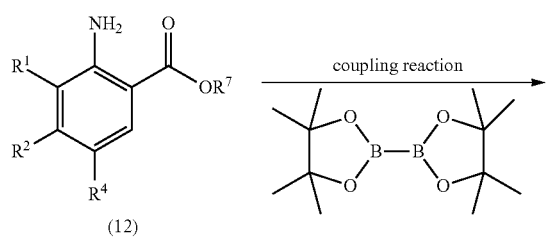

(12)

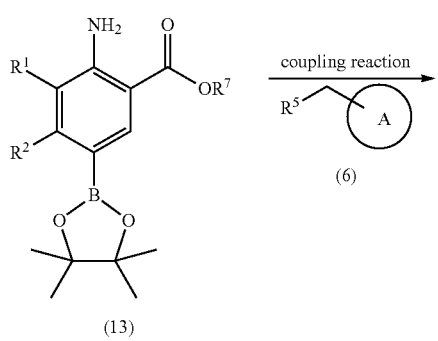

(13)

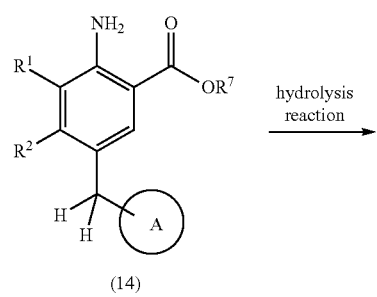

(14)

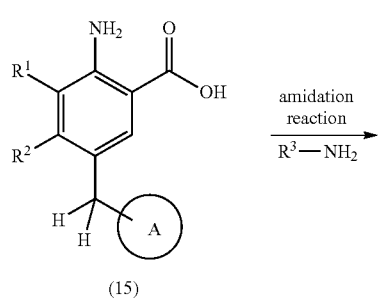

(15)

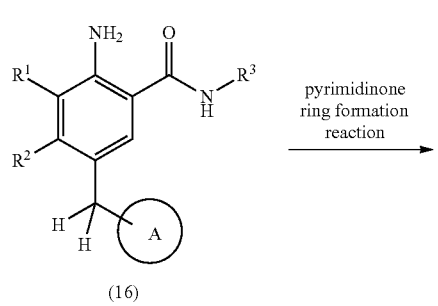

(16)

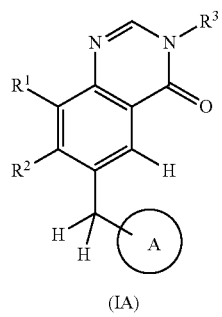

(IA)

In the reaction formulas, $R^7$ is a lower alkyl group ($C_{1-6}$ alkyl group) and ring A and $R^1$ to $R^5$ mean the same as above.

Compound (13) can be produced by a coupling reaction of compound (12) and bis(pinacolato)diboron in the presence of a metal catalyst.

Compound (14) can be produced by a coupling reaction of compound (13) and compound (6) in the presence of a metal catalyst.

Compound (15) can be produced by hydrolysis of compound (14).

Compound (16) can be produced by an amidation reaction of compound (15) and amines such as $R^3$—$NH_2$ and the like.

Compound (IA) can be produced by a pyrimidinone ring formation reaction of compound (16) and N,N-dimethylformamide dimethyl acetal.

Compound (I) wherein X is N, i.e., compound (II), can be produced by the method shown in the following schemes or a method analogous thereto or a method described in the Examples.

Compound (II) can be produced from compound (3) by the following method.

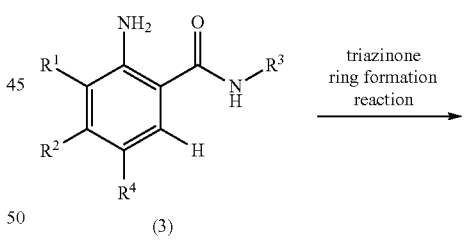

(3)

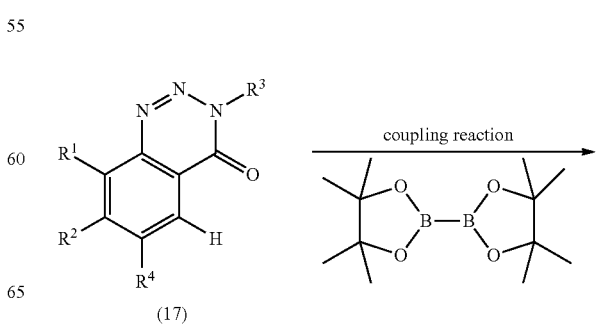

(17)

-continued

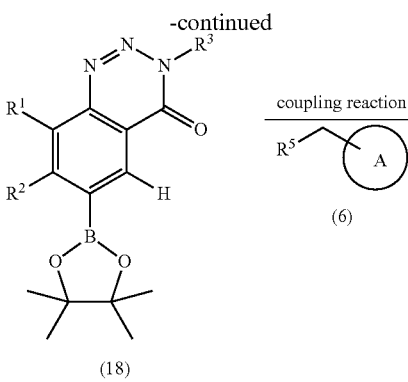

In the reaction formulas, ring A and $R^1$ to $R^5$ mean the same as above.

Compound (17) can be produced by a triazinone ring formation reaction of compound (3) and sodium nitrite.

Compound (18) can be produced by a coupling reaction of compound (17) and bis(pinacolato)diboron in the presence of a metal catalyst.

Compound (II) can be produced by a coupling reaction of compound (18) and compound (6) in the presence of a metal catalyst.

Compound (II) can also be produced from compound (16) by the following method.

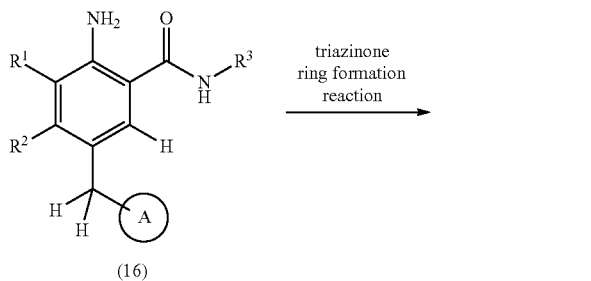

In the reaction formulas, ring A and $R^1$ to $R^3$ mean the same as above.

Compound (II) can be produced by a triazinone ring formation reaction of compound (16) and sodium nitrite.

Compound (1), compound (2), amines, compound (3), N,N-dimethylformamide dimethyl acetal, compound (4), compound (5), compound (6), compound (7), formamidine acetate, compound (8), compound (9), alkyl halide, compound (10), compound (11), compound (12), compound (13), compound (14), compound (15) and compound (16) used as starting materials for the production of Compound (IA) can be produced by a method known per se.

Compound (16), compound (17), sodium nitrite, compound (18) and amines used as starting materials for the production of Compound (II) can be produced by a method known per se.

When compound (IA) and (II) have an optical isomer, a stereoisomer, a regioisomer or a rotamer, these are also encompassed in compound (I), and can be obtained as a single product according to synthesis and separation methods known per se. For example, when compound (IA) and (II) contain an optical isomer, optical isomers resolved from the compounds are also encompassed in compound (IA) and (II).

The optical isomer can be produced according to a method known per se. To be specific, the optical isomer is obtained using an optically active synthetic intermediate, or subjecting the final racemate product to an optical resolution according to a conventional method.

For example, the method of optical resolution may be a method known per se, such as a fractional recrystallization method, a chiral column method, a diastereomer method etc.

1) Fractional Recrystallization Method

A method wherein a salt with a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine etc.) is formed, which is separated by a fractional recrystallization method, and if desired, a neutralization step to give a free optical isomer.

2) Chiral Column Method

A method wherein a racemate or a salt thereof is applied to a column for separation of an optical isomer (a chiral column) to allow separation. In the case of a liquid chromatography, for example, a mixture of the optical isomers is applied to a chiral column such as ENANTIO-OVM (manufactured by Tosoh Corporation), CHIRAL series (manufactured by Daicel Corporation) and the like, and developed with water, various buffers (e.g., phosphate buffer, etc.) and organic solvents (e.g., ethanol, methanol, isopropanol, acetonitrile, trifluoroacetic acid, diethylamine etc.), solely or as a mixed solution thereof to separate the optical isomer.

3) Diastereomer Method

A method wherein a racemic mixture is prepared into a diastereomeric mixture by chemical reaction with an optically active reagent, which is made into a single substance by a typical separation means (e.g., a fractional recrystallization method, a chromatography method etc.) and the like, and is subjected to a chemical treatment such as hydrolysis reaction and the like to remove an optically active reagent moiety, whereby an optical isomer is obtained. For example, when compound (I) contains hydroxy group, or primary or secondary amino group within a molecule, the compound and an optically active organic acid (e.g., MTPA [α-methoxy-α-(trifluoromethyl)phenylacetic acid], (−)-menthoxyacetic acid etc.) and the like are subjected to condensation reaction to give diastereomers of the ester compound or the amide compound, respectively. When compound (I) has a carboxylic acid group, this compound and an optically active amine or an optically active alcohol reagent are subjected to condensation reaction to give diastereomers of the amide compound or the ester compound, respectively. The separated diastereomer is converted to an optical isomer of the original compound by acid hydrolysis or base hydrolysis reaction.

When compound (I) is obtained as a free compound, the compound can be converted to an objective salt according to a method known per se or a method analogous thereto. Conversely, when it is obtained in the form of a salt, the salt can be converted to a free form or other objective salt according to a method known per se or a method analogous thereto.

Compound (I) may be a prodrug, and the prodrug of compound (I) refers to a compound which is converted to compound (I) as a result of a reaction with an enzyme, gastric acid, etc. under physiological conditions in vivo, thus a compound that undergoes enzymatic oxidation, reduction, hydrolysis etc. to convert to compound (I) and a compound that undergoes hydrolysis and the like by gastric acid, etc. to convert to compound (I).

Examples of the prodrug for compound (I) include a compound obtained by subjecting an amino group in compound (I) to acylation, alkylation or phosphorylation (e.g., a compound obtained by subjecting an amino group in compound (I) to eicosanoylation, alanylation, pentylaminocarbonylation, (5-methyl-2-oxo-1,3-dioxolen-4-yl)methoxycarbonylation, tetrahydrofurylation, pyrrolidylmethylation, pivaloyloxymethylation or t-butylation, and the like);
a compound obtained by subjecting a hydroxy group in compound (I) to acylation, alkylation, phosphorylation or boration (e.g., a compound obtained by subjecting a hydroxy group in compound (I) to acetylation, palmitoylation, propanoylation, pivaloylation, succinylation, fumarylation, alanylation or dimethylaminomethylcarbonylation, and the like);
a compound obtained by subjecting a carboxy group in compound (I) to esterification or amidation (e.g., a compound obtained by subjecting a carboxy group in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation, and the like) and the like. Any of these compounds can be produced from compound (I) according to a method known per se.

A prodrug of compound (I) may also be one which is converted to compound (I) under physiological conditions as described in "IYAKUHIN no KAIHATSU (Development of Pharmaceuticals)", Vol. 7, Design of Molecules, p. 163-198 (HIROKAWA SHOTEN).

Compound (I) may be useful for mammals (e.g., mouse, rat, hamster, rabbit, cat, dog, bovine, sheep, monkey, human etc.) as an agent for the prophylaxis or treatment of diseases, for example,
(1) psychiatric diseases [e.g., depression, major depression, bipolar depression, dysthymic disorder, emotional disorder (seasonal affective disorder and the like), recurrent depression, postpartum depression, stress disorder, depression symptom, mania, generalized anxiety disorder, anxiety syndrome, panic disorder, phobia, social phobia, social anxiety disorder, obsessive disorder, post-traumatic stress syndrome, post-traumatic stress disorder, Tourette syndrome, autism, autism spectrum syndrome, fragile X syndrome, Rett syndrome, adjustment disorder, bipolar disorder, neurosis, schizophrenia (e.g., positive symptom, negative symptom, and cognitive impairment), cognitive impairment associated with schizophrenia, chronic fatigue syndrome, anxiety neurosis, compulsive neurosis, epilepsy, anxiety symptom, anxious mental state, emotional abnormality, cyclothymia, nervous erethism, faint, addiction, low sex drive, attention deficit hyperactivity disorder (ADHD), psychotic major depression, intractable major depression, treatment-resistant depression],
(2) neurodegenerative diseases [e.g., Alzheimer's disease, Alzheimer-type senile dementia, Parkinson's disease, Parkinson's disease dementia, Huntington's disease, multi-infarct dementia, frontotemporal dementia, frontotemporal dementia Parkinson's Type, progressive supranuclear palsy, Pick's syndrome, Niemann-Pick syndrome, corticobasal degeneration, Down's syndrome, vascular dementia, post-encephalitic parkinsonism, Lewy body dementia, HIV dementia, amyotrophic lateral sclerosis (ALS), motor neurogenesis disease (MND), Creutzfeldt-Jakob disease or prion disease, cerebral palsy, multiple sclerosis],
(3) age-related cognition and memory disorders [e.g., age-related memory disorders, senile dementia],
(4) sleep disorders [e.g., intrinsic sleep disorders (e.g., psychophysiological insomnia and the like), extrinsic sleep disorder, circadian rhythm disorders (e.g., time zone change syndrome (jet lag), shift work sleep disorder, irregular sleep-wake pattern, delayed sleep phase syndrome, advanced sleep phase syndrome, non-24-hour sleep-wake and the like), parasomnia, sleep disorders associated with internal medical or psychiatric disorder (e.g., chronic obstructive pulmonary diseases, Alzheimer's disease, Parkinson's disease, cerebrovascular dementia, schizophrenia, depression, anxiety neurosis), stress insomnia, insomnia, insomniac neurosis, sleep apnea syndrome],
(5) respiratory depression caused by anesthetics, traumatic disease, or neurodegenerative disease and the like,
(6) traumatic brain injury, cerebral apoplexy, neurotic anorexia, eating disorder, anorexia nervosa, hyperorexia, other eating disorder, alcohol dependence, alcohol abuse, alcoholic amnesia, alcohol paranoia, alcohol preference, alcohol withdrawal, alcoholic insanity, alcohol poisoning, alcoholic jealousy, alcoholic mania, alcohol-dependent psychiatric disorder, alcoholic insanity, pharmacophilia, pharmacophobia, pharmacomania, drug withdrawal, migraine, stress headache, catatonic headache, diabetic neuropathy, obesity, diabetes, muscular convulsion, Meniere's disease, autonomic ataxia, alopecia, glaucoma, hypertension, cardiac disease, tachycardia, congestive cardiac failure, breathing, bronchial asthma, apnea, sudden infant death syndrome, inflammatory disease, allergic disease, impotence, climacteric disorder, infertility, cancer, immunodeficiency syndrome caused by HIV infection, immunodeficiency syndrome caused by stress, cerebrospinal meningitis, acromegaly, incontinence, metabolic syndrome, osteoporosis, peptic ulcer, irritable bowel syndrome, inflammatory bowel disease, ulcerative colitis, Crohn's disease, stress gastrointestinal disorder, nerological vomiting, diarrhea, constipation, postoperative ileus,
(7) pain, and the like.
A cholinergic muscarinic M1 receptor positive allosteric modulator may be particularly preferably useful for the prophylaxis or treatment of Alzheimer's disease, schizophrenia, pain, sleep disorder, Parkinson's disease dementia, Lewy body dementia and the like.

Compound (I) may have a high cholinergic muscarinic M1 receptor positive allosteric modulator activity, and it may be expected to provide an excellent prophylactic or therapeutic effect for the above-mentioned diseases.

Compound (I) may show excellent solubility in water, the second solution of Japanese Pharmacopeia Elution Test, or the second solution of Japanese Pharmacopoeia Disintegration Test, may show excellent pharmacokinetics (e.g., plasma drug half-life, brain penetration, metabolic stability, CYP inhibition), may show low toxicity (e.g., more excellent as a medicament in terms of acute toxicity, chronic toxicity, genetic toxicity, reproductive toxicity, cardiotoxicity, drug interaction, carcinogenicity, phototoxicity, and the like), and may also have excellent properties as a pharmaceutical product such as a few side effects. Therefore, compound (I) may be able to be safely administered orally or parenterally to a mammal (e.g., mouse, rat, hamster, rabbit, cat, dog, bovine, sheep, monkey, human and the like). Examples of the "parenteral" include intravenous, intramuscular, subcutaneous, intra-organ, intranasal, intradermal, instillation, intracerebral, intrarectal, intravaginal, intraperitoneal and intratumor administrations, administration to the vicinity of tumor etc. and direct administration to the lesion.

A medicament containing compound (I) (sometimes to be abbreviated as "the medicament of the present invention" in the present DESCRIPTION) may have any form (preparation form) such as powder, granule, tablet, capsule, orally disintegrable film and the like, or a liquid agent such as syrup, emulsion, injection and the like.

The medicament of the present invention may be able to be produced by a conventional method such as blending, kneading, granulation, tableting, coating, sterilization treatment, emulsification and the like according to the form of the preparation. As for the production of the preparation, for example, each item of the Japanese Pharmacopoeia Preparation General Rules and the like can be referred to. In addition, the medicament of the present invention may be formed into a sustained-release preparation containing an active ingredient and a biodegradable polymer compound. The sustained-release preparation may be able to be produced according to the method described in JP-A-H9-263545.

In the medicament of the present invention, the content of compound (I) varies depending on the form of the preparation, but may be generally 0.01 to 100% by weight, preferably 0.1 to 50% by weight, more preferably 0.5 to 20% by weight, as the amount of compound (I) relative to the whole preparation (whole medicament).

Compound (I) may be used alone or in admixture with a suitable, pharmacologically acceptable carrier, for example, excipients (e.g., starch, lactose, sucrose, calcium carbonate, calcium phosphate, etc.), binders (e.g., starch, arabic gum, carboxymethyl cellulose, hydroxypropyl cellulose, crystalline cellulose, alginic acid, gelatin, polyvinylpyrrolidone, etc.), lubricants (e.g., stearic acid, magnesium stearate, calcium stearate, talc, etc.), disintegrants (e.g., calcium carboxymethylcellulose, talc, etc.), diluents (e.g., water for injection, physiological saline, etc.) and if desired, with the additives (e.g., a stabilizer, a preservative, a colorant, a fragrance, a solubilizing agent, an emulsifier, a buffer, an isotonic agent, etc.) and the like, by a conventional method, which is processed into a dosage form of a solid agent such as powder, fine granule, granule, tablet, capsule and the like or a liquid form such as injection and the like, and safely administered orally or parenterally. When compound (I) is formed as a preparation for topical administration, it may also be directly administered to the affected part of an articular disease. In this case, an injection is preferable. The compound may also be administered as a parenteral agent for topical administration (e.g., intramuscular injection, subcutaneous injection, organ injection, injection to the vicinity of a joint and the like, solid preparation such as implant, granule, powder and the like, liquid such as suspension and the like, ointment etc.) and the like.

For formulation into an injection, for example, compound (I) is formulated into an aqueous suspension with a dispersing agent (e.g., surfactant such as Tween 80, HCO-60 and the like, polysaccharides such as carboxymethylcellulose, sodium alginate, hyaluronic acid and the like, polysorbate etc.), preservative (e.g., methylparaben, propylparaben etc.), isotonic agent (e.g., sodium chloride, mannitol, sorbitol, glucose etc.), buffer (e.g., calcium carbonate etc.), pH adjuster (e.g., sodium phosphate, potassium phosphate etc.) and the like to give a practical preparation for injection. In addition, an oily suspension may be obtained by dispersing the compound together with vegetable oil such as sesame oil, corn oil and the like or a mixture thereof with a phospholipid such as lecithin and the like, or medium-chain triglyceride (e.g., miglyol 812 etc.) to give an injection to be actually used.

The dose of compound (I) may vary depending on the subject of administration, administration route and symptoms and is not particularly limited. For example, for oral administration to adult patients (body weight adult 40 to 80 kg, for example, 60 kg) with Alzheimer's disease, the dose may be, for example, 0.001 to 1000 mg/kg body weight/day, preferably 0.01 to 100 mg/kg body weight/day, more preferably 0.1 to 10 mg/kg body weight/day, as compound (I). This amount may be administered in one to three portions per day.

The medicament of the present invention may be able to use compound (I) solely or as a pharmaceutical composition of compound (I) mixed with a pharmacologically acceptable carrier according to a method known per se (e.g., the method described in the Japanese Pharmacopoeia etc.) as the production method of a pharmaceutical preparation. The medicament of the present invention may be able to be administered safely as a pharmaceutical composition, for example, tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal administrations, and administration to the lesion).

As the aforementioned "pharmacologically acceptable carrier", various organic or inorganic carriers conventionally used as preparation materials (starting materials) may be used. For example, excipient, lubricant, binder, disintegrant and the like are used for solid preparations, and solvent, solubilizing agent, suspending agent, isotonic agent, buffer, soothing agent and the like are used for liquid preparations. Where necessary, preparation additives such as preservative, antioxidant, colorant, sweetening agent and the like may also be used.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binder include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as poly(vinyl alcohol), polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffer include buffer solutions such as phosphates, acetates, carbonates, citrates and the like.

Examples of the soothing agent include benzyl alcohol and the like.

Examples of the preservative include p-hydroxybenzoates, chlorobutanol, benzyl alcohol, phenylethyl alcohol, dehydroacetic acid, sorbic acid and the like.

Examples of the antioxidant include sulfite salt, ascorbic acid, α-tocopherol and the like.

While the pharmaceutical composition may vary according to the dosage form, administration method, carrier and the like, it may be able to be produced according to a conventional method by adding compound (I) in a proportion of generally 0.01-100% (w/w), preferably 0.1-95% (w/w), of the total amount of the preparation.

The compound (I) may be used in combination with other active ingredients (hereinafter to be abbreviated as concomitant drug).

Examples of the concomitant drug include the following. benzodiazepine (chlordiazepoxide, diazepam, potassium clorazepate, lorazepam, clonazepam, alprazolam etc.), L-type calcium channel inhibitor (pregabalin etc.), tricyclic or tetracyclic antidepressant (imipramine hydrochloride, amitriptyline hydrochloride, desipramine hydrochloride, clomipramine hydrochloride etc.), selective serotonin reuptake inhibitor (fluvoxamine maleate, fluoxetine hydrochloride, citalopram hydrobromide, sertraline hydrochloride, paroxetine hydrochloride, escitalopram oxalate etc.), serotonin-noradrenaline reuptake inhibitor (venlafaxine hydrochloride, duloxetine hydrochloride, desvenlafaxine hydrochloride etc.), noradrenaline reuptake inhibitor (reboxetine mesylate etc.), noradrenaline-dopamine reuptake inhibitor (bupropion hydrochloride etc.), mirtazapine, trazodone hydrochloride, nefazodone hydrochloride, bupropion hydrochloride, setiptiline maleate, 5-$HT_{1A}$ agonist (buspirone hydrochloride, tandospirone citrate, osemozotan hydrochloride etc.), 5-$HT_3$ antagonist (cyamemazine etc.), non-cardioselective β blocker (propranolol hydrochloride, oxprenolol hydrochloride etc.), histamine $H_1$ antagonist (hydroxyzine hydrochloride etc.), therapeutic drug for schizophrenia (chlorpromazine, haloperidol, sulpiride, clozapine, trifluoperazine hydrochloride, fluphenazine hydrochloride, olanzapine, quetiapine fumarate, risperidone, aripiprazole etc.), CRF antagonist, other antianxiety drug (meprobamate etc.), tachykinin antagonist (aprepitant, saredutant etc.), medicament that acts on metabotropic glutamate receptor, CCK antagonist, β adrenaline antagonist (amibegron hydrochloride etc.), GAT-1 inhibitor (tiagabine hydrochloride etc.), N-type calcium channel inhibitor, carbonic anhydrase II inhibitor, NMDA glycine site agonist, NMDA antagonist (memantine etc.), peripheral benzodiazepine receptor agonist, vasopressin antagonist, vasopressin V1b antagonist, vasopressin V1a antagonist, phosphodiesterase inhibitor, opioid antagonist, opioid agonist, uridine, nicotinic acid receptor agonist, thyroid hormone (T3, T4), TSH, TRH, MAO inhibitor (phenelzine sulfate, tranylcypromine sulfate, moclobemide etc.), 5-$HT_{2A}$ antagonist, 5-$HT_{2A}$ inverse agonist, COMT inhibitor (entacapone etc.), therapeutic drug for bipolar disorder (lithium carbonate, sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcoholism, therapeutic drug for autism, therapeutic drug for chronic fatigue syndrome, therapeutic drug for convulsion, therapeutic drug for fibromyalgia syndrome, therapeutic drug for headache, therapeutic drug for insomnia (etizolam, zopiclone, triazolam, zolpidem, ramelteon, indiplon etc.), therapeutic drug for quitting smoking, therapeutic drug for myasthenia gravis, therapeutic drug for cerebral infarction, therapeutic drug for mania, therapeutic drug for hypersomnia, therapeutic drug for pain, therapeutic drug for dysthymia, therapeutic drug for autonomic ataxia, therapeutic drug for male and female sexual dysfunction, therapeutic drug for migraine, therapeutic drug for pathological gambler, therapeutic drug for restless legs syndrome, therapeutic drug for substance addiction, therapeutic drug for alcohol-related syndrome, therapeutic drug for irritable bowel syndrome, therapeutic drug for Alzheimer's disease (donepezil, galanthamine, memantine, rivastigmine etc.), therapeutic drug for Parkinson's disease (levodopa, carbidopa, benserazide, selegiline, rasagiline, zonisamide, entacapone, amantadine, talipexole, pramipexole, ropinirole, rotigotine, apomorphine, cabergoline, pergolide, bromocriptine, istradefylline, trihexyphenidyl, biperiden, piroheptine, profenamine, promethazine, droxidopa, combination of those drugs etc.), therapeutic drug for Parkinson's disease dementia (rivastigmine), therapeutic drug for Lewy body dementia (donepezil), therapeutic drug for ALS (riluzole, neurotrophic factor etc.), therapeutic drug for lipid abnormality such as cholesterol-lowering drug (statin series (pravastatin sodium, atorvastatin, simvastatin, rosuvastatin etc.), fibrate (clofibrate etc.), squalene synthetase inhibitor), therapeutic drug for behavior abnormalities or suppressant of dromomania due to dementia (sedatives, antianxiety drug etc.), apoptosis inhibitor, antiobesity drug, therapeutic drug for diabetes, therapeutic drug for hypertension, therapeutic drug for hypotension, therapeutic drug for rheumatism (DMARD), anti-cancer agent, therapeutic drug for hypothyroidism (PTH), calcium receptor antagonist, sex hormone or a derivative thereof (progesterone, estradiol, estradiol benzoate etc.), neuronal differentiation promoter, nerve regeneration promoter, non-steroidal anti-inflammatory drug (meloxicam, tenoxicam, indomethacin, ibuprofen, celecoxib, rofecoxib, aspirin etc.), steroid (dexamethasone, cortisone acetate etc.), anti-cytokine drug (TNF inhibitor, MAP kinase inhibitor etc.), antibody medicament, nucleic acid or nucleic acid derivative, aptamer drug and the like.

By combining compound (I) and a concomitant drug, a superior effect such as
(1) the dose may be able to be reduced as compared to single administration of compound (I) or a concomitant drug,
(2) the drug to be combined with compound (I) may be able to be selected according to the condition of patients (mild case, severe case and the like),
(3) the period of treatment may be able to be set longer by selecting a concomitant drug having different action and mechanism from compound (I),
(4) a sustained treatment effect may be able to be designed by selecting a concomitant drug having different action and mechanism from compound (I),
(5) a synergistic effect may be able to be afforded by a combined use of compound (I) and a concomitant drug, and the like, may be achieved.

Hereinafter compound (I) and a concomitant drug used in combination are referred to as the "combination agent of the present invention".

When using the combination agent of the present invention, the administration time of compound (I) and the concomitant drug is not restricted, and the compound (I) or a pharmaceutical composition thereof and the concomitant drug or a pharmaceutical composition thereof may be able to be administered to an administration subject simultaneously, or may be administered at different times. The dosage of the concomitant drug may be determined according to the dose clinically used, and may be appropriately selected depending on an administration subject, administration route, disease, combination and the like.

The administration mode of the combination agent of the present invention is not particularly restricted, and it may be sufficient that compound (I) and the concomitant drug may be combined in administration. Examples of such administration mode include the following methods:
(1) administration of a single preparation obtained by simultaneously processing compound (I) and the concomitant drug,
(2) simultaneous administration of two kinds of preparations of compound (I) and the concomitant drug, which have been separately produced, by the same administration route, (3) administration of two kinds of preparations of compound (I) and the concomitant drug, which have been separately produced, by the same administration route in a staggered manner, (4) simultaneous administration of two kinds of preparations of compound (I) and the concomitant drug, which have been separately produced, by different administration routes, (5) administration of two kinds of preparations of compound (I) and the concomitant drug, which have been separately produced, by different administration routes in a staggered manner (e.g., administration in the order of compound (I) and the concomitant drug, or in the reverse order) and the like.

The combination agent of the present invention may exhibit low toxicity. For example, compound (I) or(and) the aforementioned concomitant drug may be combined with a pharmacologically acceptable carrier according to the known method to prepare a pharmaceutical composition such as tablets (including sugar-coated tablet and film-coated tablet), powders, granules, capsules (including soft capsule), liquids, injections, suppositories, sustained-release agents, etc. These compositions may be administered safely orally or non-orally (e.g., topical, rectal, intravenous administration etc.). Injection may be administered intravenously, intramuscularly, subcutaneously, or by intraorgan administration or directly to the lesion.

Examples of the pharmacologically acceptable carriers usable for the production of a combination agent in the present invention, various organic or inorganic carrier substances conventionally used as preparation materials may be mentioned. For solid preparations, for example, excipient, lubricant, binder and disintegrant may be used. For liquid preparations, for example, solvent, solubilizing agent, suspending agent, isotonic agent, buffering agent, soothing agent and the like may be used. Where necessary, additives such as conventional preservative, antioxidant, colorant, sweetening agent, adsorbent, wetting agent and the like may be used as appropriate.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binder include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as poly(vinyl alcohol), polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffer include buffer solutions such as phosphates, acetates, carbonates, citrates and the like.

Examples of the soothing agent include benzyl alcohol and the like.

Examples of the preservative include p-hydroxybenzoates, chlorobutanol, benzyl alcohol, phenylethyl alcohol, dehydroacetic acid, sorbic acid and the like.

Examples of the antioxidant include sulfite salt, ascorbic acid, α-tocopherol and the like.

The mixing ratio of compound (I) to the concomitant drug in the combination agent of the present invention may be able to be appropriately selected depending on an administration subject, administration route, diseases and the like.

For example, the content of compound (I) in the combination agent of the present invention differs depending on the form of a preparation, and usually from about 0.01 to about 100 wt %, preferably from about 0.1 to about 50 wt %, further preferably from about 0.5 to about 20 wt %, based on the whole preparation.

The content of the concomitant drug in the combination agent of the present invention differs depending on the form of a preparation, and usually from about 0.01 to about 100 wt %, preferably from about 0.1 to about 50 wt %, further preferably from about 0.5 to about 20 wt %, based on the whole preparation.

The content of additives such as a carrier and the like in the combination agent of the present invention differs depending on the form of a preparation, and usually from about 1 to about 99.99 wt %, preferably from about 10 to about 90 wt %, based on the whole preparation.

When compound (I) and a concomitant drug are separately formulated into preparations, the contents thereof are similar to the above.

EXAMPLE

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, NH means use of aminopropylsilane-bound silica gel. In HPLC (high performance liquid chromatography), C18 means use of octadecyl-bound silica gel. The ratios of elution solvents are volume mixing ratios, unless otherwise specified.

The "osmium oxide (fixed catalyst I)" in Example means osmium(VIII) oxide (about 7% content) fixed to high solvent resistance polymer, which is commercially available from Wako Pure Chemical Industries, Ltd., unless otherwise specified. In addition, "sodium hydride" means a 60% oil dispersion (mineral oil mixture).

In the following Examples, the following abbreviations are used.
MS: mass spectrum
M: molar concentration
$CDCl_3$: deuterochloroform
DMSO: dimethyl sulfoxide
DMSO-$d_6$: deuterodimethyl sulfoxide
$^1$H NMR: proton nuclear magnetic resonance
LC/MS: liquid chromatograph mass spectrometer
ESI: electrospray ionization
APCI: atmospheric chemical ionization
DME: 1,2-dimethoxyethane
DMF: N,N-dimethylformamide
DMA: N,N-dimethylacetamide
THF: tetrahydrofuran
HATU: 2-(7-azabenzotriazol-1-yl)-1,1,3,3-tetramethyluronium hexa fluorophosphate
HOBt: 1-hydroxybenzotriazole
WSC: 1-ethyl-3-(3-dimethylaminopropyl)carbodiimide
SFC: supercritical fluid chromatography
tRn (n=1-4): retention time by high performance liquid chromatography (number shows the order of elution)

$^1$H NMR was measured by Fourier-transform NMR. For the analysis, ACD/SpecManager (trade name) and the like were used. Very mild peaks for protons of a hydroxy group, an amino group and the like are not described.

MS was measured by LC/MS. As ionization, ESI method or APCI method was used. The data indicates those actual measured (found). Generally, molecular ion peaks ([M+H]$^+$, [M−H]$^-$ and the like) are observed. In the case of a compound having a tert-butoxycarbonyl group, a peak after elimination of a tert-butoxycarbonyl group or tert-butyl group may be observed as a fragment ion. In the case of a compound having a hydroxy group, a peak after elimination of $H_2O$ may be observed as a fragment ion. In the case of a salt, a molecular ion peak or fragment ion peak of free form is generally observed.

The unit of the sample concentration (c) by optical rotation ($[\alpha]_D$) is g/100 mL.

Elemental analytical value (Anal.) shows calculated value (Calcd) and measured value (Found).

Example 1

3-(trans-2-hydroxycyclohexyl)-7,8-dimethyl-6-(4-(1H-pyrazol-1-yl)benzyl)quinazolin-4(3H)-one A) 2-amino-5-bromo-3,4-dimethylbenzoic Acid To a solution of 2-amino-3,4-dimethylbenzoic acid (2.0 g) in DMSO (25 mL) was added hydrobromic acid (48% v/v, 10.2 g) under water cooling, and the mixture was stirred at room temperature for 48 hr. To the reaction mixture was added water (25 mL) and the mixture was cooled at 0° C. for 10 min. The precipitate was collected by filtration, washed with water, and dried under reduced pressure to give the title compound (2.41 g).

MS: [M−H]$^-$ 242.0, 244.0.

B) 2-amino-5-bromo-N-(trans-2-hydroxycyclohexyl)-3,4-dimethylbenzamide

To a mixture of 2-amino-5-bromo-3,4-dimethylbenzoic acid (0.50 g), trans-2-aminocyclohexanol hydrochloride (0.78 g), and triethylamine (2.07 g) in DMF (10 mL) was added HATU (1.94 g) at room temperature and the mixture was stirred overnight and further stirred at 80° C. overnight. To the reaction mixture was added a 5% aqueous sodium hydrogen carbonate solution, and the mixture was extracted with ethyl acetate. The organic layer was washed with saturated brine, and dried over anhydrous sodium sulfate. The solvent was evaporated under reduced pressure. The residue was purified by silica gel column chromatography (ethyl acetate/hexane) to give the title compound (0.61 g).

MS: [M+H]$^+$ 341.1, 343.1

C) 6-bromo-3-(trans-2-hydroxycyclohexyl)-7,8-dimethylquinazolin-4(3H)-one

2-Amino-5-bromo-N-(trans-2-hydroxycyclohexyl)-3,4-dimethylbenzamide (0.30 g) was dissolved in N,N-dimethylformamide dimethyl acetal (0.67 g) and the mixture was stirred at 80° C. for 15 hr. The reaction mixture was concentrated under reduced pressure, and the residue was washed with ethyl acetate to give the title compound (0.17 g).

MS: [M+H]$^+$ 351.1, 353.1

D) 3-(trans-2-hydroxycyclohexyl)-7,8-dimethyl-6-(4,4,5,5-tetramethyl-1,3,2-dioxaborolan-2-yl)quinazolin-4(3H)-one To a mixture of 6-bromo-3-(trans-2-hydroxycyclohexyl)-7,8-dimethylquinazolin-4(3H)-one (0.17 g), bis(pinacolato)diboron (0.18 g), potassium acetate (0.14 g) and toluene (4.0 mL) was added bis(triphenylphosphine)palladium(II) chloride (0.02 g), and the mixture was stirred under an argon atmosphere at 110° C. for 16 hr. To the reaction mixture was added water, and the mixture was extracted with ethyl acetate. The organic layer was washed with water and saturated brine, and dried over anhydrous magnesium sulfate and the solvent was evaporated under reduced pressure. The residue was purified by silica gel column chromatography (ethyl acetate/hexane) to give the title compound (0.17 g).

MS: [M+H]$^+$ 399.2

E) 3-(trans-2-hydroxycyclohexyl)-7,8-dimethyl-6-(4-(1H-pyrazol-1-yl)benzyl)quinazolin-4(3H)-one To a mixture of 3-(trans-2-hydroxycyclohexyl)-7,8-dimethyl-6-(4,4,5,5-tetramethyl-1,3,2-dioxaborolan-2-yl)quinazolin-4(3H)-one (0.16 g), sodium carbonate (0.09 g), 1-(4-(bromomethyl)phenyl)-1H-pyrazole (0.10 g), DME (2.4 mL) and water (0.8 mL) was added tetrakis(triphenylphosphine)palladium(0) (0.02 g) under an argon atmosphere, and the mixture was stirred at 80° C. overnight. To the reaction mixture was added water, and the mixture was extracted with ethyl acetate. The organic layer was washed with water and saturated brine, and dried over anhydrous sodium sulfate. The solvent was evaporated under reduced pressure. The residue was purified by silica gel column chromatography (ethyl acetate/hexane) to give the title compound (0.07 g).

$^1$H NMR (300 MHz, DMSO-d$_6$) δ1.27-1.40 (3H, m), 1.64-1.85 (4H, m), 1.96-2.07 (1H, m), 2.28 (3H, s), 2.52 (3H, s), 3.95 (1H, br. s), 4.19 (2H, s), 4.37 (1H, br. s), 4.90 (1H, d, J=5.7 Hz), 6.48-6.55 (1H, m), 7.23 (1H, s), 7.26 (1H, s), 7.67-7.86 (4H, m), 8.38 (1H, s), 8.43 (1H, d, J=2.6 Hz).

Example 2

3-(trans-2-hydroxycyclopentyl)-7,8-dimethyl-6-(4-(1H-pyrazol-1-yl)benzyl)quinazolin-4(3H)-one A) 2-amino-5-bromo-N-(trans-2-hydroxycyclopentyl)-3,4-dimethylbenzamide A mixture of 2-amino-5-bromo-3,4-dimethylbenzoic acid (0.10 g), trans-2-aminocyclopentanol hydrochloride (0.06 g), triethylamine (0.10 g) and HATU (0.19 g) in DMF (2.0 mL) was stirred at room temperature overnight. To the reaction mixture was added 5% aqueous sodium hydrogen carbonate solution, and the mixture was extracted with ethyl acetate. The organic layer was washed with saturated brine, and dried over anhydrous sodium sulfate. The solvent was evaporated under reduced pressure to give the title compound (0.17 g). Further purification was not performed and the compound was used in the next step.

MS: [M+H]$^+$ 327.1, 329.1

B) 6-bromo-3-(trans-2-hydroxycyclopentyl)-7,8-dimethylquinazolin-4(3H)-one

2-Amino-5-bromo-N-(trans-2-hydroxycyclopentyl)-3,4-dimethylbenzamide (0.13 g) was dissolved in N,N-dimethylformamide dimethyl acetal (0.49 mL), and the mixture was stirred at 80° C. for 15 hr. The reaction mixture was concentrated under reduced pressure, and the residue was washed with ethyl acetate-hexane to give the title compound (0.09 g).

MS: [M+H]$^+$ 337.1, 339.1

C) 3-(trans-2-hydroxycyclopentyl)-7,8-dimethyl-6-(4,4,5,5-tetramethyl-1,3,2-dioxaborolan-2-yl)quinazolin-4(3H)-one To a mixture of 6-bromo-3-(trans-2-hydroxycyclopentyl)-7,8-dimethylquinazolin-4(3H)-one (0.09 g), bis(pinacolato)diboron (0.08 g), potassium acetate (0.08 g) and toluene (3 mL) was added bis(triphenylphosphine)palladium(II) chloride (0.01 g), and the mixture was stirred under an argon atmosphere at 110° C. overnight. To the reaction mixture was added 5% aqueous sodium hydrogen carbonate solution, and the mixture was extracted with ethyl acetate. The organic layer was washed with saturated brine, and dried over anhydrous sodium sulfate. The solvent was evaporated under reduced pressure. The residue was crystallized from diisopropyl ether to give the title compound (0.06 g). Further purification was not performed and the compound was used in the next step.

MS: [M+H]$^+$ 385.2

D) 3-(trans-2-hydroxycyclopentyl)-7,8-dimethyl-6-(4-(1H-pyrazol-1-yl)benzyl)quinazolin-4(3H)-one To a mixture of 3-(trans-2-hydroxycyclopentyl)-7,8-dimethyl-6-(4,4,5,5-tetramethyl-1,3,2-dioxaborolan-2-yl)quinazolin-4(3H)-one (0.06 g), sodium carbonate (0.03 g), 1-(4-(bromomethyl)phenyl)-1H-pyrazole (0.04 g), DME (0.75 mL) and water (0.25 mL) was added tetrakis(triphenylphosphine)palladium(0) (0.01 g), and the mixture was stirred under an argon atmosphere at 80° C. overnight. To the reaction mixture was added water, and the mixture was extracted with ethyl acetate. The organic layer was washed with saturated brine, and dried over anhydrous sodium sulfate. The solvent was evaporated under reduced pressure. The residue was purified by silica gel column chromatography (ethyl acetate/hexane) and NH silica gel column chromatography (ethyl acetate/hexane) to give the title compound (0.02 g).

$^1$H NMR (300 MHz, DMSO-d$_6$) δ1.57 (1H, dt, J=12.2, 8.0 Hz), 1.71-1.86 (2H, m), 1.95-2.10 (2H, m), 2.29 (3H, s), 2.52 (3H, s), 3.29 (1H, s), 4.19 (2H, s), 4.33-4.53 (1H, m), 4.53-4.69 (1H, m), 5.06 (1H, d, J=4.9 Hz), 6.45-6.57 (1H, m), 7.25 (2H, d, J=8.3 Hz), 7.67-7.82 (4H, m), 8.36 (1H, s), 8.43 (1H, d, J=2.3 Hz).

Example 3

3-(trans-4-hydroxytetrahydro-2H-pyran-3-yl)-7,8-dimethyl-6-(4-(1H-pyrazol-1-yl)benzyl)quinazolin-4(3H)-one synonym: 1,5-anhydro-2,4-dideoxy-2-(7,8-dimethyl-4-oxo-6-(4-(1H-pyrazol-1-yl)benzyl)quinazolin-3(4H)-yl)-threo-pentitol A) 2-amino-5-bromo-N-(trans-4-hydroxytetrahydro-2H-pyran-3-yl)-3,4-dimethylbenzamide To a mixture of 2-amino-5-bromo-3,4-dimethylbenzoic acid (0.10 g), trans-3-aminotetrahydro-2H-pyran-4-ol hydrochloride (0.05 g), triethylamine (0.10 g) and DMF (2 mL) was added HATU (0.19 g), and the mixture was stirred at room temperature overnight. To the reaction mixture was added water, and the mixture was extracted with ethyl acetate. The organic layer was washed with saturated brine, and dried over anhydrous sodium sulfate. The solvent was evaporated under reduced pressure to give the title compound (0.19 g). Further purification was not performed and the compound was used in the next step.

MS: [M+H]$^+$ 343.1, 345.1

B) 6-bromo-3-(trans-4-hydroxytetrahydro-2H-pyran-3-yl)-7,8-dimethylquinazolin-4(3H)-one 2-Amino-5-bromo-N-(trans-4-hydroxytetrahydro-2H-pyran-3-yl)-3,4-dimethylbenzamide (0.14 g) was dissolved in N,N-dimethylformamide dimethyl acetal (0.49 mL), and the mixture was stirred at 80° C. for 15 hr. The reaction mixture was concentrated under reduced pressure, and the residue was washed with ethyl acetate-hexane to give the title compound (0.10 g). Further purification was not performed and the compound was used in the next step.

MS: [M+H]$^+$ 353.1, 355.1

C) 3-(trans-4-hydroxytetrahydro-2H-pyran-3-yl)-7,8-dimethyl-6-(4,4,5,5-tetramethyl-1,3,2-dioxaborolan-2-yl)quinazolin-4(3H)-one To a mixture of 6-bromo-3-(trans-4-hydroxytetrahydro-2H-pyran-3-yl)-7,8-dimethylquinazolin-4(3H)-one (0.10 g), bis(pinacolato)diboron (0.09 g), potassium acetate (0.09 g) and toluene (3 mL) was added bis(triphenylphosphine)palladium(II) chloride (0.01 g), and the mixture was stirred under an argon atmosphere at 110° C. overnight. To the reaction mixture was added a 5% aqueous sodium hydrogen carbonate solution, and the mixture was extracted with ethyl acetate. The organic layer was washed with saturated brine, and dried over anhydrous sodium sulfate. The solvent was evaporated under reduced pressure. The residue was purified by silica gel column chromatography (ethyl acetate/hexane) to give the title compound (0.11 g).

MS: [M+H]$^+$ 401.2

D) 3-(trans-4-hydroxytetrahydro-2H-pyran-3-yl)-7,8-dimethyl-6-(4-(1H-pyrazol-1-yl)benzyl)quinazolin-4(3H)-one synonym: 1,5-anhydro-2,4-dideoxy-2-(7,8-dimethyl-4-oxo-6-(4-(1H-pyrazol-1-yl)benzyl)quinazolin-3(4H)-yl)-threo-pentitol To a mixture of 3-(trans-4-hydroxytetrahydro-2H-pyran-3-yl)-7,8-dimethyl-6-(4,4,5,5-tetramethyl-1,3,2-dioxaborolan-2-yl)quinazolin-4(3H)-one (0.11 g), sodium carbonate (0.06 g), 1-(4-(bromomethyl)phenyl)-1H-pyrazole (0.06 g), DME (1.5 mL) and water (0.5 mL) was added tetrakis(triphenylphosphine)palladium(0) (0.02 g), and the mixture was stirred under an argon atmosphere at 80° C. overnight. To the reaction mixture was added water, and the mixture was extracted with ethyl acetate. The organic layer was washed with saturated brine, and dried over anhydrous sodium sulfate. The solvent was evaporated under reduced pressure. The residue was purified by silica gel column chromatography (ethyl acetate/hexane) and recrystallized from ethyl acetate and hexane to give the title compound (0.05 g).

$^1$H NMR (300 MHz, CDCl$_3$) δ1.84 (1H, brs), 2.10-2.23 (2H, m), 2.28 (3H, s), 2.57 (3H, s), 3.62 (1H, td, J=11.4, 2.5 Hz), 3.95-4.13 (3H, m), 4.17 (2H, s), 4.35-4.46 (2H, m), 6.39-6.48 (1H, m), 7.11-7.22 (2H, m), 7.50-7.65 (2H, m), 7.70 (1H, d, J=1.7 Hz), 7.87 (1H, d, J=2.5 Hz), 7.98 (1H, s), 8.17 (1H, s).

Example 4

7,8-dimethyl-6-(4-(1H-pyrazol-1-yl)benzyl)-3-(tetrahydrofuran-2-ylmethyl)quinazolin-4(3H)-one

A) 2-amino-5-bromo-3,4-dimethyl-N-((tetrahydrofuran-2-yl)methyl)benzamide

To a mixture of 2-amino-5-bromo-3,4-dimethylbenzoic acid (0.10 g), (tetrahydrofuran-2-yl)methanamine (0.04 g), triethylamine (0.10 g) and DMF (2 mL) was added HATU (0.19 g), and the mixture was stirred at room temperature overnight. To the reaction mixture was added water, and the mixture was extracted with ethyl acetate. The organic layer was washed with saturated brine, and dried over anhydrous sodium sulfate. The solvent was evaporated under reduced pressure to give the title compound (0.18 g). Further purification was not performed and the compound was used in the next step.

MS: [M+H]$^+$ 327.1, 329.1

B) 6-bromo-7,8-dimethyl-3-((tetrahydrofuran-2-yl)methyl)quinazolin-4(3H)-one 2-Amino-5-bromo-3,4-dimethyl-N-((tetrahydrofuran-2-yl)methyl)benzamide (0.13 g) was dissolved in N,N-dimethylformamide dimethyl acetal (0.49 mL), and the mixture was stirred at 80° C. for 15 hr. The reaction mixture was concentrated under reduced pressure, and the residue was washed with ethyl acetate-hexane to give the title compound (0.11 g).

MS: [M+H]$^+$ 337.1, 339.1

C) 7,8-dimethyl-3-((tetrahydrofuran-2-yl)methyl)-6-(4,4,5,5-tetramethyl-1,3,2-dioxaborolan-2-yl)quinazolin-4(3H)-one To a mixture of 6-bromo-7,8-dimethyl-3-((tetrahydrofuran-2-yl)methyl)quinazolin-4(3H)-one (0.11 g), bis(pinacolato)diboron (0.10 g), potassium acetate (0.09 g) and toluene (3 mL) was added bis(triphenylphosphine)palladium(II) chloride (0.01 g), and the mixture was stirred under an argon atmosphere at 110° C. overnight. To the reaction mixture was added a 5% aqueous sodium hydrogen carbonate solution, and the mixture was extracted with ethyl acetate. The organic layer was washed with saturated brine, and dried over anhydrous sodium sulfate. The solvent was evaporated under reduced pressure. The residue was purified by silica gel column chromatography (ethyl acetate/hexane) to give the title compound (0.11 g).

MS: [M+H]$^+$ 385.2

D) 7,8-dimethyl-6-(4-(1H-pyrazol-1-yl)benzyl)-3-(tetrahydrofuran-2-ylmethyl)quinazolin-4(3H)-one To a mixture of 7,8-dimethyl-3-((tetrahydrofuran-2-yl)methyl)-6-(4,4,5,5-tetramethyl-1,3,2-dioxaborolan-2-yl)quinazolin-4(3H)-one (0.11 g), sodium carbonate (0.06 g), 1-(4-(bromomethyl)phenyl)-1H-pyrazole (0.07 g), DME (1.5 mL) and water (0.5 mL) was added tetrakis(triphenylphosphine)palladium(0) (0.02 g), and the mixture was stirred under an argon atmosphere at 80° C. overnight. To the reaction mixture was added water, and the mixture was extracted with ethyl acetate. The organic layer was washed with saturated brine, and dried over anhydrous sodium sulfate. The solvent was evaporated under reduced pressure. The residue was purified by silica gel column chromatography (ethyl acetate/hexane) and recrystallized from ethyl acetate-hexane to give the title compound (0.05 g).
$^1$H NMR (300 MHz, CDCl$_3$) δ1.57-1.70 (1H, m), 1.82-1.96 (2H, m), 2.05-2.13 (1H, m), 2.27 (3H, s), 2.58 (3H, s), 3.68-3.81 (1H, m), 3.81-3.93 (2H, m), 4.17 (2H, s), 4.19-4.27 (1H, m), 4.34 (1H, dd, J=13.6, 3.0 Hz), 6.44 (1H, t, J=2.2 Hz), 7.14-7.22 (2H, m), 7.53-7.62 (2H, m), 7.70 (1H, d, J=1.5 Hz), 7.87 (1H, d, J=2.5 Hz), 8.03 (1H, s), 8.15 (1H, s).

Example 5

7,8-dimethyl-6-(4-(1H-pyrazol-1-yl)benzyl)quinazolin-4(3H)-one

A) 6-bromo-7,8-dimethylquinazolin-4(3H)-one

A mixture of 2-amino-5-bromo-3,4-dimethylbenzoic acid (2.0 g), formamidine acetate (3.41 g) and 2-methoxyethanol (50 mL) was heated under reflux at 130° C. overnight. Then, the reaction mixture was concentrated under reduced pressure. The precipitate was collected by filtration and washed with methanol to give the title compound (1.67 g).
MS: [M−H]$^−$ 251.0, 253.0

B) 7,8-dimethyl-6-(4,4,5,5-tetramethyl-1,3,2-dioxaborolan-2-yl)quinazolin-4(3H)-one To a mixture of 6-bromo-7,8-dimethylquinazolin-4(3H)-one (1.57 g), bis(pinacolato)diboron (1.65 g), potassium acetate (1.83 g) and toluene (45 mL) was added bis(triphenylphosphine)palladium(II) chloride (0.22 g), and the mixture was stirred under an argon atmosphere at 110° C. overnight. To the reaction mixture was added a 5% aqueous sodium hydrogen carbonate solution and the precipitate was collected by filtration and washed with toluene and water to give the title compound (2.30 g). Further purification was not performed and the compound was used in the next step.
MS: [M+H]$^+$ 301.1

C) 7,8-dimethyl-6-(4-(1H-pyrazol-1-yl)benzyl)quinazolin-4(3H)-one

To a mixture of 7,8-dimethyl-6-(4,4,5,5-tetramethyl-1,3,2-dioxaborolan-2-yl)quinazolin-4(3H)-one (1.86 g), sodium carbonate (1.31 g), 1-(4-(bromomethyl)phenyl)-1H-pyrazole (1.47 g), DME (24 mL) and water (8 mL) was added tetrakis(triphenylphosphine)palladium(0) (0.36 g), and the mixture was stirred under an argon atmosphere at 80° C. overnight. To the reaction mixture was added water, and the mixture was extracted with ethyl acetate. The organic layer was washed with saturated brine, and dried over anhydrous sodium sulfate. The solvent was evaporated under reduced pressure. The residue was purified by silica gel column chromatography (ethyl acetate/hexane) and recrystallized from ethyl acetate-hexane to give the title compound (0.05 g).
$^1$H NMR (300 MHz, DMSO-d$_6$) δ2.29 (3H, s), 2.52 (3H, brs), 4.17 (2H, s), 6.46-6.55 (1H, m), 7.25 (2H, d, J=8.5 Hz), 7.64-7.82 (4H, m), 8.07 (1H, s), 8.44 (1H, d, J=2.5 Hz), 12.10 (1H, brs).

Example 6

2-(7,8-dimethyl-4-oxo-6-(4-(1H-pyrazol-1-yl)benzyl)quinazolin-3(4H)-yl)-3-fluorobenzonitrile A mixture of 2,3-difluorobenzonitrile (0.04 g), potassium carbonate (0.06 g), 7,8-dimethyl-6-(4-(1H-pyrazol-1-yl)benzyl)quinazolin-4(3H)-one (0.05 g) and DMF (1 mL) was stirred under an argon atmosphere at 150° C. overnight. To the reaction mixture was added water, and the mixture was extracted with ethyl acetate. The organic layer was washed with saturated brine, and dried over anhydrous sodium sulfate. The solvent was evaporated under reduced pressure. The residue was purified by silica gel column chromatography (ethyl acetate/hexane) and further purified by preparative HPLC (C18, water/acetonitrile, containing 0.1% trifluoroacetic acid), and the object fraction was neutralized with saturated aqueous sodium hydrogen carbonate solution, and the mixture was extracted with ethyl acetate. The organic layer was dried over anhydrous sodium sulfate and the solvent was evaporated under reduced pressure to give the title compound (0.01 g).
$^1$H NMR (300 MHz, CDCl$_3$) δ2.32 (3H, s), 2.63 (3H, s), 4.20 (2H, s), 6.44 (1H, s), 7.21 (2H, d, J=8.5 Hz), 7.52-7.73 (6H, m), 7.88 (1H, d, J=2.5 Hz), 7.95 (1H, d, J=0.9 Hz), 8.09 (1H, s).

Example 8

3,7,8-trimethyl-6-(4-(1H-pyrazol-1-yl)benzyl)quinazolin-4(3H)-one

A) 3,7,8-trimethyl-6-(4,4,5,5-tetramethyl-1,3,2-dioxaborolan-2-yl)quinazolin-4(3H)-one A mixture of 7,8-dimethyl-6-(4,4,5,5-tetramethyl-1,3,2-dioxaborolan-2-yl)quinazolin-4(3H)-one (0.10 g), potassium carbonate (0.14 g), methyl iodide (0.05 g) and DMF (2 mL) was stirred at 95° C. overnight. To the reaction mixture was added water, and the mixture was extracted with ethyl acetate. The organic layer was washed with saturated brine, and dried over anhydrous sodium sulfate. The solvent was evaporated under reduced pressure. The residue was crystallized from ethyl acetate-hexane to give the title compound (0.06 g). Further purification was not performed and the compound was used in the next step.
$^1$H NMR (300 MHz, CDCl$_3$) δ1.24 (12H, s), 2.89 (3H, s), 2.96 (3H, s), 3.57 (3H, s), 8.02 (1H, s), 8.05 (1H, s).

B) 3,7,8-trimethyl-6-(4-(1H-pyrazol-1-yl)benzyl)quinazolin-4(3H)-one

To a mixture of 3,7,8-trimethyl-6-(4,4,5,5-tetramethyl-1,3,2-dioxaborolan-2-yl)quinazolin-4(3H)-one (0.06 g), sodium carbonate (0.04 g), 1-(4-(bromomethyl)phenyl)-1H-pyrazole (0.05 g), DME (0.75 mL) and water (0.25 mL) was added tetrakis(triphenylphosphine)palladium(0) (0.01 g), and the mixture was stirred under an argon atmosphere at 80° C. overnight. To the reaction mixture was added 5% aqueous sodium hydrogen carbonate solution, and the mixture was extracted with ethyl acetate. The organic layer was washed with saturated brine, and dried over anhydrous sodium sulfate. The solvent was evaporated under reduced pressure. The residue was purified by preparative HPLC (C18, water/acetonitrile, containing 0.1% trifluoroacetic acid), the object fraction was neutralized with saturated aqueous sodium hydrogen carbonate solution, and the mixture was extracted with ethyl acetate. The organic layer was dried over anhydrous sodium sulfate, the solvent was evaporated under reduced pressure, and the residue was purified by silica gel column chromatography (ethyl acetate/hexane) to give the title compound (0.006 g).
$^1$H NMR (300 MHz, CDCl$_3$) δ2.27 (3H, s), 2.57 (3H, s), 3.59 (3H, s), 4.18 (2H, s), 6.40-6.47 (1H, m), 7.18 (2H, d, J=8.3 Hz), 7.58 (2H, d, J=8.5 Hz), 7.70 (1H, d, J=1.7 Hz), 7.87 (1H, d, J=2.3 Hz), 8.04 (2H, d, J=4.2 Hz).

Example 9

1-((3-(trans-2-hydroxycyclopentyl)-7,8-dimethyl-4-oxo-3,4-dihydroquinazolin-6-yl)methyl)-4-(pyridin-2-yl)piperidine-4-carbonitrile A) 3-(trans-2-hydroxycyclopentyl)-7,8-dimethyl-6-vinylquinazolin-4(3H)-one A mixture of 6-bromo-3-(trans-2-hydroxycyclopentyl)-7,8-dimethylquinazolin-4(3H)-one (0.10 g), 2-vinyl-4,4,5,5-tetramethyl-1,3,2-dioxaborolane (0.07 g), sodium carbonate (0.06 g), tetrakis(triphenylphosphine)palladium(0) (0.02 g), DME (1.5 mL) and water (0.5 mL) was stirred under an argon atmosphere at 80° C. overnight. The reaction mixture was cooled to room temperature, and poured into water, and the mixture was extracted with ethyl acetate. The organic layer was washed with water and saturated brine, dried over anhydrous magnesium sulfate and the solvent was evaporated under reduced pressure. The residue was purified by silica gel column chromatography (ethyl acetate/hexane) to give the title compound (0.09 g).
MS: [M+H]$^+$ 285.2

B) 3-(trans-2-hydroxycyclopentyl)-7,8-dimethyl-4-oxo-3,4-dihydroquinazoline-6-carbaldehyde A mixture of 3-(trans-2-hydroxycyclopentyl)-7,8-dimethyl-6-vinylquinazolin-4(3H)-one (0.09 g), osmium oxide (immobilized catalyst I) (0.04 g), sodium periodate (0.32 g), acetonitrile (1.5 mL), acetone (1.5 mL) and water (1.5 mL) was stirred at room temperature overnight. Insoluble material was filtered off and the filtrate was diluted with ethyl acetate and washed with saturated brine. The organic layer was dried over anhydrous sodium sulfate, and the solvent was evaporated under reduced pressure to give the title compound (0.03 g). Further purification was not performed and the compound was used in the next step.
MS: [M+H]$^+$ 287.1

C) 1-((3-(trans-2-hydroxycyclopentyl)-7,8-dimethyl-4-oxo-3,4-dihydroquinazolin-6-yl)methyl)-4-(pyridin-2-yl)piperidine-4-carbonitrile A mixture of 3-(trans-2-hydroxycyclopentyl)-7,8-dimethyl-4-oxo-3,4-dihydroquinazoline-6-carbaldehyde (0.03 g), 4-(pyridin-2-yl)piperidine-4-carbonitrile dihydrochloride (0.03 g), triethylamine (0.03 g), THF (1.0 mL) and toluene (1.0 mL) was stirred at room temperature for 5 min and the reaction mixture was concentrated under reduced pressure. To the residue were added THF (1.0 mL) and toluene (1.0 mL), and the mixture was stirred at room temperature for 5 min and the reaction mixture was concentrated under reduced pressure. This operation was performed twice. A mixture of the residue, THF (1.6 mL), and sodium triacetoxyborohydride (0.05 g) was stirred under an argon atmosphere at room temperature overnight. To the reaction mixture was added a 5% aqueous sodium hydrogen carbonate solution at room temperature, and the mixture was extracted with ethyl acetate. The organic layer was washed with saturated brine, and dried over anhydrous sodium sulfate. The solvent was evaporated under reduced pressure. The residue was purified by silica gel column chromatography (ethyl acetate/hexane) and triturated with ethyl acetate and hexane to give the title compound (0.003 g).
$^1$H NMR (300 MHz, CDCl$_3$) δ1.73-1.87 (1H, m), 1.96 (2H, t, J=7.2 Hz), 2.02-2.18 (4H, m), 2.20-2.39 (3H, m), 2.47 (3H, s), 2.54-2.65 (5H, m), 2.98 (2H, d, J=12.3 Hz), 3.18 (1H, d, J=3.2 Hz), 3.69 (2H, s), 4.41 (1H, d, J=3.2 Hz), 4.60-4.74 (1H, m), 7.21-7.25 (1H, m), 7.53-7.62 (1H, m), 7.66-7.80 (1H, m), 8.10 (1H, s), 8.07 (1H, s), 8.61 (1H, d, J=5.5 Hz).

Example 10

3-(trans-2-hydroxycyclopentyl)-7,8-dimethyl-6-(4-(1-methyl-1H-pyrazol-3-yl)benzyl)quinazolin-4(3H)-one A) (4-(1-methyl-1H-pyrazol-3-yl)phenyl)methanol To a mixture of 3-bromo-1-methylpyrazole (0.91 g), toluene (18 mL), ethanol (3.0 mL) and water (3.0 mL) were added (4-(hydroxymethyl)phenyl)boronic acid (1.1 g), sodium carbonate (0.60 g) and dichloro[1,1'-bis(diphenylphosphino)ferrocene]palladium (0.52 g) at room temperature, and the mixture was stirred under an argon atmosphere at 110° C. overnight. The reaction mixture was filtered, and the filtrate was diluted with ethyl acetate, washed with water and saturated brine and dried over anhydrous sodium sulfate. The solvent was evaporated under reduced pressure and the residue was purified by silica gel column chromatography (ethyl acetate/hexane) and triturated with ethyl acetate and hexane to give the title compound (1.1 g).
MS: [M+H]$^+$ 189.1

B) 3-(4-(bromomethyl)phenyl)-1-methyl-1H-pyrazole

A mixture of (4-(1-methyl-1H-pyrazol-3-yl)phenyl)methanol (0.22 g), phosphorus tribromide (0.38 g) and toluene (3 mL) was stirred under ice-cooling for 2 hr. The reaction mixture was poured into a saturated aqueous sodium hydrogen carbonate solution under ice-cooling, and the mixture was extracted with ethyl acetate. The organic layer was washed with water and saturated brine, and dried over anhydrous magnesium sulfate and the solvent was evaporated under reduced pressure. The residue was purified by silica gel column chromatography (ethyl acetate/hexane) to give the title compound (0.21 g).
MS: [M+H]$^+$ 251.0, 253.0

C) 3-(trans-2-hydroxycyclopentyl)-7,8-dimethyl-6-(4-(1-methyl-1H-pyrazol-3-yl)benzyl)quinazolin-4(3H)-one To a mixture of 3-(trans-2-hydroxycyclopentyl)-7,8-dimethyl-6-(4,4,5,5-tetramethyl-1,3,2-dioxaborolan-2-yl)quinazolin-4(3H)-one (0.08 g), sodium carbonate (0.04 g), 3-(4-(bromomethyl)phenyl)-1-methyl-1H-pyrazole (0.05 g), DME (1.0 mL) and water (0.33 mL) was added tetrakis(triphenylphosphine)palladium(0) (0.01 g) under an argon atmosphere, and the mixture was stirred at 85° C. overnight. To the reaction mixture was added a 5% aqueous sodium hydrogen carbonate solution, and the mixture was extracted with ethyl acetate. The organic layer was washed with saturated brine, and dried over anhydrous sodium sulfate. The solvent was evaporated under reduced pressure. The residue was purified by silica gel column chromatography (ethyl acetate/hexane) to give the title compound (0.06 g).

¹H NMR (300 MHz, CDCl₃) δ1.71-2.02 (3H, m), 2.06-2.22 (2H, m), 2.28 (4H, s), 2.56 (3H, s), 3.26 (1H, d, J=3.0 Hz), 3.93 (3H, s), 4.12-4.21 (2H, m), 4.41 (1H, dt, J=5.1, 2.7 Hz), 4.67 (1H, td, J=8.5, 5.7 Hz), 6.49 (1H, d, J=2.3 Hz), 7.05-7.17 (2H, m), 7.30-7.40 (1H, m), 7.62-7.74 (2H, m), 8.03 (1H, s), 8.10 (1H, s).

Example 11

3-(trans-2-hydroxycyclopentyl)-7,8-dimethyl-6-(4-(1-methyl-1H-1,2,3-triazol-4-yl)benzyl)quinazolin-4(3H)-one A) (4-(1-methyl-1H-1,2,3-triazol-4-yl)phenyl)methanol To a solution of triphenylphosphine (1.5 g) in methanol (25 mL) was added copper(II) bromide (0.31 g) at 60° C., and the mixture was stirred at the same temperature for 10 min. The solid was recovered, and washed with ethanol and diethyl ether to give copper(I) bromide triphenylphosphine adduct [CuBr(PPh₃)₃] (1.18 g). The obtained copper(I) bromide triphenylphosphine adduct was added to a mixture of (4-ethynylphenyl)methanol (0.50 g), sodium azide (0.32 g) and methyl iodide (0.54 g) in DMSO (8 mL)-water (2 mL) at room temperature, and the mixture was stirred overnight. To the reaction mixture was added a saturated aqueous ammonium chloride solution at room temperature, and the mixture was extracted with ethyl acetate. The organic layer was washed with water and saturated brine, and dried over anhydrous magnesium sulfate and the solvent was evaporated under reduced pressure. The residue was purified by silica gel column chromatography (ethyl acetate/hexane) to give the title compound (0.45 g).
MS: [M+H]⁺ 190.1

B) 4-(4-(bromomethyl)phenyl)-1-methyl-1H-1,2,3-triazole

A mixture of (4-(1-methyl-1H-1,2,3-triazol-4-yl)phenyl)methanol (0.10 g) in DMF (1 mL) was stirred under an argon atmosphere at 0° C. for 5 min. To the mixture was added phosphorus tribromide (0.17 g) under ice-cooling, and the mixture was stirred under an argon atmosphere at room temperature for 30 min. To the reaction mixture was added a 5% aqueous sodium hydrogen carbonate solution, and the mixture was extracted with ethyl acetate. The organic layer was washed with water and saturated brine, and dried over anhydrous sodium sulfate. The solvent was evaporated under reduced pressure. The residue was washed with hexane to give the title compound (0.12 g).
¹H NMR (300 MHz, CDCl₃) δ4.16 (3H, s), 4.53 (2H, s), 7.40-7.50 (2H, m), 7.75 (1H, s), 7.77-7.84 (2H, m).

C) 3-(trans-2-hydroxycyclopentyl)-7,8-dimethyl-6-(4-(1-methyl-1H-1,2,3-triazol-4-yl)benzyl)quinazolin-4(3H)-one To a mixture of 3-(trans-2-hydroxycyclopentyl)-7,8-dimethyl-6-(4,4,5,5-tetramethyl-1,3,2-dioxaborolan-2-yl)quinazolin-4(3H)-one (0.08 g), sodium carbonate (0.04 g), 4-(4-(bromomethyl)phenyl)-1-methyl-1H-1,2,3-triazole (0.05 g), DME (1.0 mL) and water (0.33 mL) was added tetrakis(triphenylphosphine)palladium(0) (0.01 g), and the mixture was stirred under an argon atmosphere at 85° C. overnight. To the reaction mixture was added a 5% aqueous sodium hydrogen carbonate solution, and the mixture was extracted with ethyl acetate. The organic layer was washed with saturated brine, and dried over anhydrous sodium sulfate. The solvent was evaporated under reduced pressure. The residue was purified by silica gel column chromatography (methanol/ethyl acetate) to give the title compound (0.06 g).
¹H NMR (300 MHz, CDCl₃) δ1.75-1.88 (1H, m), 1.90-2.04 (2H, m), 2.06-2.20 (2H, m), 2.20-2.37 (4H, m), 2.57 (3H, s), 3.30 (1H, d, J=3.0 Hz), 4.00-4.25 (5H, m), 4.32-4.49 (1H, m), 4.67 (1H, td, J=8.6, 5.8 Hz), 7.07-7.21 (2H, m), 7.62-7.77 (3H, m), 8.01 (1H, s), 8.10 (1H, s).

Example 12

3-(trans-2-hydroxycyclopentyl)-7,8-dimethyl-6-((2'-methyl-2,4'-bipyridin-5-yl)methyl)quinazolin-4(3H)-one A) 6-((6-chloropyridin-3-yl)methyl)-3-(trans-2-hydroxycyclopentyl)-7,8-dimethylquinazolin-4(3H)-one To a mixture of 6-bromo-3-(trans-2-hydroxycyclopentyl)-7,8-dimethylquinazolin-4(3H)-one (0.76 g), (6-chloro-3-pyridyl)methylzinc chloride (0.5 M THF solution) (11.3 mL) and THF (3 mL) was added bis(tri-tert-butylphosphine)palladium(0) (0.23 g) under ice-cooling, and the mixture was stirred under an argon atmosphere at room temperature overnight. To the reaction mixture was added a 5% aqueous sodium hydrogen carbonate solution and ethyl acetate was added. Insoluble material was filtered off, and the organic layer was washed with saturated brine and dried over anhydrous sodium sulfate. The solvent was evaporated under reduced pressure. The residue was purified by silica gel column chromatography (ethyl acetate/hexane) to give the title compound (0.72 g).
¹H NMR (300 MHz, CDCl₃) δ1.74-1.90 (1H, m), 1.90-2.03 (2H, m), 2.06-2.21 (2H, m), 2.21-2.37 (4H, m), 2.57 (3H, s), 3.11 (1H, brs), 4.08-4.16 (2H, m), 4.35-4.47 (1H, m), 4.66 (1H, td, J=8.5, 5.8 Hz), 7.16-7.25 (1H, m), 7.30-7.38 (1H, m), 7.97 (1H, s), 8.11 (1H, s), 8.23 (1H, d, J=2.1 Hz).

B) 3-(trans-2-hydroxycyclopentyl)-7,8-dimethyl-6-((2'-methyl-2,4'-bipyridin-5-yl)methyl)quinazolin-4(3H)-one To a mixture of 6-((6-chloropyridin-3-yl)methyl)-3-(trans-2-hydroxycyclopentyl)-7,8-dimethylquinazolin-4(3H)-one (0.10 g), 2-methyl-4-(4,4,5,5-tetramethyl-1,3,2-dioxaborolan-2-yl)pyridine (0.11 g), potassium carbonate (0.14 g), THF (1.5 mL) and water (0.5 mL) was added tetrakis(triphenylphosphine)palladium(0) (0.03 g), and the mixture was stirred under an argon atmosphere at 85° C. overnight. The reaction mixture was diluted with ethyl acetate and dried over anhydrous sodium sulfate. The solvent was evaporated under reduced pressure. The residue was purified by silica gel column chromatography (methanol/ethyl acetate) to give the title compound (0.02 g).
¹H NMR (300 MHz, CDCl₃) δ1.74-1.89 (1H, m), 1.97 (2H, t, J=7.3 Hz), 2.07-2.21 (2H, m), 2.28 (1H, s), 2.31 (3H, s), 2.59 (3H, s), 2.64 (3H, s), 3.15 (1H, d, J=3.4 Hz), 4.21 (2H, s), 4.41 (1H, d, J=7.7 Hz), 4.60-4.72 (1H, m), 7.49 (1H, dd, J=8.2, 2.4 Hz), 7.59-7.65 (1H, m), 7.68 (1H, d, J=8.5 Hz), 7.76 (1H, s), 8.02 (1H, s), 8.12 (1H, s), 8.53-8.62 (2H, m).

Example 14

3-(trans-2-hydroxycyclopentyl)-7,8-dimethyl-6-((6-(1-methyl-1H-1,2,3-triazol-4-yl)pyridin-3-yl)methyl)quinazolin-4(3H)-one

A) 5-(((tert-butyldimethylsilyl)oxy)methyl)-2-chloropyridine

A mixture of (6-chloropyridin-3-yl)methanol (6.50 g), 1H-imidazole (6.16 g), tert-butyldimethylchlorosilane (6.82 g) and THF (40 mL) was stirred at room temperature overnight. The reaction mixture was poured into water at room temperature and the mixture was extracted twice with ethyl acetate. The residue was purified by silica gel column chromatography (ethyl acetate/hexane) to give the title compound (11.1 g).

MS: $[M+H]^+$ 258.1

B) 5-(((tert-butyldimethylsilyl)oxy)methyl)-2-((trimethylsilyl) ethynyl) pyridine A mixture of 5-(((tert-butyldimethylsilyl)oxy)methyl)-2-chloropyridine (8.98 g), ethynyltrimethylsilane (5.13 g), copper(I) iodide (0.33 g), triethylamine (52.9 g), (1,1-bis(diphenylphosphino)ferrocene)dichloropalladium(II) dichloromethane adduct (1.42 g) and acetonitrile (100 mL) was stirred under a nitrogen atmosphere at 70° C. for 3 hr. The reaction mixture was concentrated under reduced pressure and the residue was diluted with water and extracted with ethyl acetate. The organic layer was washed with saturated brine, and dried over anhydrous magnesium sulfate and the solvent was evaporated under reduced pressure. The residue was purified by silica gel column chromatography (ethyl acetate/hexane) to give the title compound (11.1 g).

MS: $[M+H]^+$ 320.0

C) 5-(((tert-butyldimethylsilyl)oxy)methyl)-2-ethynylpyridine

A mixture of 5-(((tert-butyldimethylsilyl)oxy)methyl)-2-((trimethylsilyl)ethynyl)pyridine (11.1 g), potassium carbonate (4.80 g) in methanol (50 mL) was stirred at room temperature for 2 hr. The reaction mixture was concentrated under reduced pressure, and the residue was diluted with saturated aqueous ammonium chloride solution and extracted with ethyl acetate. The organic layer was washed with saturated brine, and dried over anhydrous magnesium sulfate and the solvent was evaporated under reduced pressure to give the title compound (8.60 g).

MS: $[M+H]^+$ 248.0

D) 5-(((tert-butyldimethylsilyl)oxy)methyl)-2-(1-methyl-1H-1,2,3-triazol-4-yl)pyridine To a mixture of 5-(((tert-butyldimethylsilyl)oxy)methyl)-2-ethynylpyridine (8.60 g), copper(I) bromide triphenylphosphine adduct (3.07 g), methyl iodide (5.43 g) and DMSO (80 mL) was added dropwise a solution of sodium azide (3.39 g) in water (20 mL), and the mixture was stirred under a nitrogen atmosphere at room temperature overnight. The reaction mixture was diluted with water at room temperature and the precipitate was collected by filtration. Isolated precipitate was dissolved in ethanol, and the resulting insoluble material was filtered off. The filtrate was extracted with ethyl acetate and the organic layer was washed with saturated brine and dried over anhydrous magnesium sulfate. The solvent was evaporated under reduced pressure and the residue was purified by silica gel column chromatography (ethyl acetate/hexane) to give the title compound (7.03 g).

MS: $[M+H]^+$ 305.3

E) (6-(1-methyl-1H-1,2,3-triazol-4-yl)pyridin-3-yl)methanol

A mixture of 1 M tetra-N-butylammonium fluoride THF solution (69.3 mL) and 5-(((tert-butyldimethylsilyl)oxy)methyl)-2-(1-methyl-1H-1,2,3-triazol-4-yl)pyridine (7.03 g) in THF (70 mL) was stirred at room temperature for 18 hr. The reaction mixture was concentrated and the residue was purified by silica gel column chromatography (methanol/ethyl acetate) to give the title compound (3.78 g).

MS: $[M+H]^+$ 191.2

F) 5-(bromomethyl)-2-(1-methyl-1H-1,2,3-triazol-4-yl)pyridine

To a mixture of (6-(1-methyl-1H-1,2,3-triazol-4-yl)pyridin-3-yl)methanol (0.40 g) in acetonitrile (8 mL) was added phosphorus tribromide (0.85 g) under ice-cooling, and the mixture was stirred under an argon atmosphere at room temperature for 30 min. To the reaction mixture was added saturated aqueous sodium hydrogen carbonate solution, and the mixture was extracted with ethyl acetate. The organic layer was dried over anhydrous sodium sulfate and the solvent was evaporated under reduced pressure. The residue was washed with ethyl acetate-hexane to give the title compound (0.27 g).

MS: $[M+H]^+$ 253.1, 255.1

G) 3-(trans-2-hydroxycyclopentyl)-7,8-dimethyl-6-((6-(1-methyl-1H-1,2,3-triazol-4-yl)pyridin-3-yl)methyl)quinazolin-4(3H)-one To a mixture of 3-(trans-2-hydroxycyclopentyl)-7,8-dimethyl-6-(4,4,5,5-tetramethyl-1,3,2-dioxaborolan-2-yl)quinazolin-4(3H)-one (0.10 g), sodium carbonate (0.06 g), 5-(bromomethyl)-2-(1-methyl-1H-1,2,3-triazol-4-yl)pyridine (0.07 g), DME (1.0 mL) and water (0.33 mL) was added tetrakis(triphenylphosphine)palladium(0) (0.02 g), and the mixture was stirred under an argon atmosphere at 85° C. overnight. The reaction mixture was diluted with ethyl acetate and dried over anhydrous sodium sulfate. The solvent was evaporated under reduced pressure. The residue was purified by silica gel column chromatography (methanol/ethyl acetate) and recrystallized from ethyl acetate-hexane to give the title compound (0.05 g).

$^1$H NMR (300 MHz, CDCl$_3$) δ1.81 (1H, d, J=4.8 Hz), 1.89-2.02 (2H, m), 2.07-2.21 (2H, m), 2.26 (1H, s), 2.30 (3H, s), 2.58 (3H, s), 3.14 (1H, d, J=3.1 Hz), 4.16 (3H, s), 4.17 (2H, s), 4.34-4.48 (1H, m), 4.66 (1H, d, J=5.5 Hz), 7.46 (1H, dd, J=8.2, 2.3 Hz), 8.02 (1H, s), 8.03-8.09 (2H, m), 8.11 (1H, s), 8.41 (1H, s).

Example 15

3-(trans-2-hydroxycyclopentyl)-7,8-dimethyl-6-((6-(1-methyl-1H-pyrazol-4-yl)pyridin-3-yl)methyl)quinazolin-4(3H)-one To a mixture of 6-((6-chloropyridin-3-yl)methyl)-3-(trans-2-hydroxycyclopentyl)-7,8-dimethylquinazolin-4

(3H)-one (0.10 g), 1-methyl-4-(4,4,5,5-tetramethyl-1,3,2-dioxaborolan-2-yl)-1H-pyrazole (0.11 g), potassium carbonate (0.14 g), THF (1.5 mL) and water (0.5 mL) was added tetrakis(triphenylphosphine)palladium(0) (0.03 g), and the mixture was stirred under an argon atmosphere at 85° C. overnight. The reaction mixture was diluted with ethyl acetate and dried over anhydrous sodium sulfate. The solvent was evaporated under reduced pressure. The residue was purified by silica gel column chromatography (methanol/ethyl acetate) to give the title compound (0.09 g).

$^1$H NMR (300 MHz, CDCl$_3$) δ1.81 (1H, dd, J=12.7, 7.4 Hz), 1.88-2.02 (2H, m), 2.06-2.24 (2H, m), 2.24-2.36 (4H, m), 2.57 (3H, s), 3.25 (1H, d, J=3.2 Hz), 3.94 (3H, s), 4.12 (2H, s), 4.35-4.48 (1H, m), 4.66 (1H, td, J=8.6, 5.8 Hz), 7.33 (2H, d, J=1.6 Hz), 7.88 (2H, d, J=6.5 Hz), 8.00 (1H, s), 8.10 (1H, s), 8.38 (1H, s).

Example 17

3-(trans-2-hydroxycyclopentyl)-7,8-dimethyl-6-(4-(1-methyl-1H-pyrazol-4-yl)benzyl)quinazolin-4(3H)-one A) (4-(1-methyl-1H-pyrazol-4-yl)phenyl)methanol A mixture of (4-(hydroxymethyl)phenyl)boronic acid (10.1 g), 4-bromo-1-methyl-1H-pyrazole (9.76 g), potassium phosphate (38.6 g), tetrakis(triphenylphosphine)palladium(0) (3.50 g), toluene (200 mL), ethanol (40 ml) and water (40 ml) was stirred under an argon atmosphere at 80° C. overnight. Water was added to the reaction mixture and insoluble material (including crude crystal of the object product) was collected by filtration. The filtrate was extracted with ethyl acetate, and the organic layer was washed with saturated brine and dried over anhydrous sodium sulfate. The solvent was evaporated under reduced pressure and the residue was triturated with ethyl acetate-hexane. The residue was combined with the crude crystal obtained earlier and dissolved in ethyl acetate at 80° C., and insoluble material was filtered off. The filtrate was concentrated under reduced pressure and the residue was triturated with ethyl acetate-hexane to give the title compound (8.07 g).

$^1$H NMR (300 MHz, CDCl$_3$) δ1.65 (1H, t, J=5.9 Hz), 3.95 (3H, s), 4.69 (2H, d, J=6.0 Hz), 7.32-7.40 (2H, m), 7.44-7.51 (2H, m), 7.61 (1H, s), 7.76 (1H, d, J=0.8 Hz).

B) 4-(4-(chloromethyl)phenyl)-1-methyl-1H-pyrazole

A mixture of (4-(1-methyl-1H-pyrazol-4-yl)phenyl)methanol (8.07 g), mesyl chloride (9.82 g) and triethylamine (8.68 g) in THF (170 mL) was stirred under an argon atmosphere at 50° C. for 5 hr. The reaction mixture was diluted with ethyl acetate, and the organic layer was washed with saturated brine and dried over anhydrous sodium sulfate. The solvent was evaporated under reduced pressure to give the title compound (8.11 g).

MS: [M+H]$^+$ 207.1

C) 3-(trans-2-hydroxycyclopentyl)-7,8-dimethyl-6-(4-(1-methyl-1H-pyrazol-4-yl)benzyl)quinazolin-4(3H)-one To a mixture of 3-(trans-2-hydroxycyclopentyl)-7,8-dimethyl-6-(4,4,5,5-tetramethyl-1,3,2-dioxaborolan-2-yl)quinazolin-4(3H)-one (0.15 g), sodium carbonate (0.08 g), 4-(4-(chloromethyl)phenyl)-1-methyl-1H-pyrazole (0.08 g), DME (1.5 mL) and water (0.5 al) was added tetrakis(triphenylphosphine)palladium(0) (0.02 g), and the mixture was stirred under an argon atmosphere at 85° C. for 6 hr. The reaction mixture was diluted with ethyl acetate and dried over anhydrous sodium sulfate. The solvent was evaporated under reduced pressure. The residue was purified by silica gel column chromatography (methanol/ethyl acetate) and recrystallized from ethyl acetate-hexane to give the title compound (0.12 g).

$^1$H NMR (300 MHz, CDCl$_3$) δ1.75-1.90 (1H, m), 1.90-2.02 (2H, m), 2.06-2.19 (2H, m), 2.28 (1H, s), 2.31 (3H, s), 2.58 (3H, s), 3.18 (1H, d, J=3.0 Hz), 3.93 (3H, s), 4.14 (2H, s), 4.42 (1H, s), 4.59-4.75 (1H, m), 7.10 (2H, d, J=8.3 Hz), 7.36 (2H, d, J=8.2 Hz), 7.56 (1H, s), 7.71 (1H, s), 8.02 (1H, s), 8.10 (1H, s).

Example 22

3-(trans-2-hydroxycyclopentyl)-7,8-dimethyl-6-(4-(1-methyl-1H-1,2,3-triazol-4-yl)benzyl)quinazolin-4(3H)-one (optical isomer: retention time short)

3-(trans-2-Hydroxycyclopentyl)-7,8-dimethyl-6-(4-(1-methyl-1H-1,2,3-triazol-4-yl)benzyl)quinazolin-4(3H)-one (0.04 g) was optically resolved by HPLC (CHIRALPAK AD (AF003), 50 mmID×500 mmL, mobile phase: ethanol/hexane) to give the title compound (0.01 g) having a shorter retention time (tR1).

$^1$H NMR (300 MHz, CDCl$_3$) δ1.74-1.87 (1H, m), 1.88-2.03 (2H, m), 2.03-2.19 (2H, m), 2.19-2.38 (4H, m), 2.58 (3H, s), 3.19 (1H, d, J=3.0 Hz), 4.14 (3H, s), 4.18 (2H, s), 4.41 (1H, d, J=4.7 Hz), 4.60-4.74 (1H, m), 7.17 (2H, d, J=8.3 Hz), 7.65-7.76 (3H, m), 8.03 (1H, s), 8.10 (1H, s).

Example 23

3-(trans-2-hydroxycyclopentyl)-7,8-dimethyl-6-(4-(1-methyl-1H-1,2,3-triazol-4-yl)benzyl)quinazolin-4(3H)-one (optical isomer: retention time long)

3-(trans-2-Hydroxycyclopentyl)-7,8-dimethyl-6-(4-(1-methyl-1H-1,2,3-triazol-4-yl)benzyl)quinazolin-4(3H)-one (0.04 g) was optically resolved by HPLC (CHIRALPAK AD (AF003), 50 mmID×500 mmL, mobile phase: ethanol/hexane) to give the title compound (0.01 g) having a longer retention time (tR2).

$^1$H NMR (300 MHz, CDCl$_3$) δ1.74-1.88 (1H, m), 1.88-2.03 (2H, m), 2.03-2.22 (2H, m), 2.30 (4H, s), 2.58 (3H, s), 3.19 (1H, d, J=3.2 Hz), 4.14 (3H, s), 4.18 (2H, s), 4.35-4.45 (1H, m), 4.62-4.71 (1H, m), 7.17 (2H, d, J=8.0 Hz), 7.68-7.75 (3H, m), 8.03 (1H, s), 8.10 (1H, s).

Example 38

8-fluoro-3-((3S,4S)-4-hydroxytetrahydro-2H-pyran-3-yl)-7-methyl-6-(4-(1H-pyrazol-1-yl)benzyl)quinazolin-4(3H)-one synonym: 1,5-anhydro-2,4-dideoxy-2-(8-fluoro-7-methyl-4-oxo-6-(4-(1H-pyrazol-1-yl)benzyl)quinazolin-3(4H)-yl)-L-threo-pentitol A) methyl 2-amino-5-bromo-3-fluoro-4-methylbenzoate To a mixture of methyl 2-amino-3-fluoro-4-methylbenzoate (21.1 g) and ethyl acetate (105 mL) was added 4N hydrochloric acid/ethyl acetate solution (34.6 mL) at room temperature. To the reaction mixture was added hexane (100 mL), and the precipitate was collected by filtration. To a mixture of the obtained methyl 2-amino-3-fluoro-4-methylbenzoate hydrochloride (18.4 g) and DMF (180 mL) was added N-bromosuccinimide (15.2 g) under ice-cooling, and the mixture was stirred at room temperature for 1 hr. To the reaction mixture was added saturated aqueous sodium hydrogen carbonate solution, and the mixture was extracted twice with ethyl acetate. The organic layer was washed with aqueous sodium thiosulfate solution, water and saturated brine, and dried over anhydrous magnesium sulfate and the solvent was evaporated under reduced pressure. The residue was purified by silica gel column chromatography (ethyl acetate/hexane) to give the title compound (15.8 g).

$^1$H NMR (300 MHz, CDCl$_3$) δ2.31 (3H, d, J=3.0 Hz), 3.87 (3H, s), 5.75 (2H, brs), 7.83 (1H, d, J=1.9 Hz).

B) methyl 5-(4-(1H-pyrazol-1-yl)benzyl)-2-amino-3-fluoro-4-methylbenzoate

Under a nitrogen stream, lithium chloride (0.32 g), zinc powder (0.50 g) and a stirrer bar were added to a reaction container, and the mixture was heated under reduced pressure at 180° C. for 15 min. After cooling to room temperature, the reaction container was filled with nitrogen, THF (2 mL) and 1,2-dibromoethane (0.04 g) were added and the mixture was heated until air bubbles were developed. To the mixture was added trimethylsilyl chloride (0.02 g) and the mixture was stirred at 70° C. for 15 min. To the mixture was added 1-(4-(chloromethyl)phenyl)-1H-pyrazole (0.96 g) at room temperature and the mixture was stirred at 70° C. for 2 hr. The reaction mixture was cooled at room temperature, a mixture of palladium acetate (0.02 g), 2-dicyclohexylphosphino-2',6'-dimethoxybiphenyl (0.06 g) and methyl 2-amino-5-bromo-3-fluoro-4-methylbenzoate (1.0 g) in THF (5 mL) was added dropwise, and the mixture was stirred under a nitrogen atmosphere at 70° C. for 1 hr and then at room temperature overnight. To the reaction mixture was added saturated aqueous ammonium chloride solution, and the mixture was extracted with ethyl acetate. The organic layer was washed with saturated brine, and dried over anhydrous magnesium sulfate and the solvent was evaporated under reduced pressure. The residue was purified by silica gel column chromatography to give the title compound (1.2 g).

MS: [M+H]$^+$ 340.2

C) 5-(4-(1H-pyrazol-1-yl)benzyl)-2-amino-3-fluoro-4-methylbenzoic acid

To a mixture of methyl 5-(4-(1H-pyrazol-1-yl)benzyl)-2-amino-3-fluoro-4-methylbenzoate (0.20 g) and THF (10 mL) was added 4 M aqueous lithium hydroxide solution (0.59 mL), and the mixture was stirred at room temperature overnight and then at 60° C. for 5 hr. The reaction mixture was neutralized with 2 M hydrochloric acid under ice-cooling and extracted with ethyl acetate. The organic layer was washed with saturated brine and dried over anhydrous magnesium sulfate to give the title compound (0.19 g).

MS: [M+H]$^+$ 326.1

D) 5-(4-(1H-pyrazol-1-yl)benzyl)-2-amino-3-fluoro-N-((3S,4S)-4-hydroxytetrahydro-2H-pyran-3-yl)-4-methylbenzamide To a mixture of 5-(4-(1H-pyrazol-1-yl)benzyl)-2-amino-3-fluoro-4-methylbenzoic acid (0.19 g), (3S,4S)-3-aminotetrahydro-2H-pyran-4-ol (0.07 g), WSC hydrochloride (0.14 g), HOBt monohydrate (0.10 g) and DMF (3.0 mL) was added triethylamine (0.07 g), and the mixture was stirred at room temperature overnight. To the reaction mixture was added water at room temperature and the precipitate was washed with water and dried under reduced pressure to give the title compound (0.23 g). Further purification was not performed and the compound was used in the next step.

MS: [M+H]$^+$ 425.2

E) 8-fluoro-3-((3S,4S)-4-hydroxytetrahydro-2H-pyran-3-yl)-7-methyl-6-(4-(1H-pyrazol-1-yl)benzyl)quinazolin-4(3H)-one synonym: 1,5-anhydro-2,4-dideoxy-2-(8-fluoro-7-methyl-4-oxo-6-(4-(1H-pyrazol-1-yl)benzyl)quinazolin-3(4H)-yl)-L-threo-pentitol A mixture of N,N-dimethylformamide dimethyl acetal (1.0 mL) and 5-(4-(1H-pyrazol-1-yl)benzyl)-2-amino-3-fluoro-N-((3S,4S)-4-hydroxytetrahydro-2H-pyran-3-yl)-4-methylbenzamide (0.06 g) was stirred at 85° C. for 3 hr. The reaction mixture was cooled to room temperature and concentrated under reduced pressure. The residue was purified by silica gel column chromatography (ethyl acetate/hexane) to give the title compound (0.01 g).

$^1$H NMR (300 MHz, DMSO-d$_6$) δ1.60 (1H, d, J=10.4 Hz), 1.92-2.06 (1H, m), 2.29 (3H, d, J=2.3 Hz), 3.39-3.54 (1H, m), 3.58-3.75 (1H, m), 3.79-3.97 (2H, m), 4.20 (2H, s), 4.21-4.31 (1H, m), 4.33-4.50 (1H, m), 5.24 (1H, d, J=5.1 Hz), 6.52 (1H, dd, J=2.5, 1.9 Hz), 7.28 (2H, d, J=8.5 Hz), 7.70-7.82 (4H, m), 8.38-8.42 (1H, m), 8.45 (1H, d, J=2.5 Hz).

Example 39

7,8-dimethyl-6-((6-(1-methyl-1H-pyrazol-4-yl)pyridin-3-yl)methyl)-3-(tetrahydrofuran-2-ylmethyl)-1,2,3-benzotriazin-4(3H)-one

A) 6-bromo-7,8-dimethyl-3-((tetrahydrofuran-2-yl)methyl)benzo[d][1,2,3]triazin-4(3H)-one To a mixture of 2-amino-5-bromo-3,4-dimethyl-N-((tetrahydrofuran-2-yl)methyl)benzamide (2.68 g), 6N hydrochloric acid (8.19 mL) and water (30 mL) was added dropwise a solution of sodium nitrite (0.59 g) in water (7.0 mL) under ice-cooling, and the mixture was stirred for 2.5 hr. The reaction mixture was neutralized with 8N aqueous sodium hydroxide solution and the precipitate was collected by filtration to give the title compound (2.37 g). Further purification was not performed and the compound was used in the next step.

MS: [M+H]$^+$ 338.0, 340.0

B) 6-((6-chloropyridin-3-yl)methyl)-7,8-dimethyl-3-((tetrahydrofuran-2-yl)methyl)benzo[d][1,2,3]triazin-4(3H)-one To a mixture of 6-bromo-7,8-dimethyl-3-((tetrahydrofuran-2-yl)methyl)benzo[d][1,2,3]triazin-4(3H)-one (1.25 g), (6-chloro-3-pyridyl)methylzinc chloride (0.5 M THF solution) (18.5 mL) and THF (18 mL) was added bis(tri-tert-butylphosphine)palladium(0) (0.38 g) under ice-cooling, and the mixture was stirred under an argon atmosphere at room temperature for 4 hr. To the reaction mixture were added a 5% aqueous sodium hydrogen carbonate solution and ethyl acetate, and the mixture was stirred at room temperature for 10 min. The insoluble material was filtered off and the organic layer was washed with saturated brine and dried over anhydrous sodium sulfate. The solvent was evaporated under reduced pressure. The residue was triturated with ethyl acetate-hexane to give the title compound (1.12 g).

MS: [M+H]$^+$ 385.1

C) 7,8-dimethyl-6-((6-(1-methyl-1H-pyrazol-4-yl)pyridin-3-yl)methyl)-3-(tetrahydrofuran-2-ylmethyl)-1,2,3-benzotriazin-4(3H)-one To a mixture of 6-((6-chloropyridin-3-yl)methyl)-7,8-dimethyl-3-((tetrahydrofuran-2-yl)methyl)benzo[d][1,2,3]triazin-4(3H)-one (0.20 g), 1-methyl-4-(4,4,5,5-tetramethyl-1,3,2-dioxaborolan-2-yl)-1H-pyrazole (0.22 g), potassium carbonate (0.29 g), THF (1.5 mL) and water (0.5 mL) was added tetrakis(triphenylphosphine)palladium(0) (0.06 g), and the mixture was stirred under an argon atmosphere at 85° C. overnight. The reaction mixture was diluted with ethyl acetate and dried over anhydrous sodium sulfate. The solvent was evaporated under reduced pressure. The residue was purified by silica gel column chromatography (methanol/ethyl acetate) to give the title compound (0.15 g).

$^1$H NMR (300 MHz, CDCl$_3$) δ1.70-1.85 (1H, m), 1.85-2.17 (3H, m), 2.36 (3H, s), 2.79 (3H, s), 3.71-3.85 (1H, m), 3.92-4.01 (4H, m), 4.17 (2H, s), 4.42-4.57 (3H, m), 7.29-7.39 (2H, m), 7.89 (2H, d, J=6.5 Hz), 8.04 (1H, s), 8.38 (1H, s).

Example 40

3-(trans-2-hydroxycyclopentyl)-7,8-dimethyl-6-(4-(1-methyl-1H-1,2,3-triazol-4-yl)benzyl)-1,2,3-benzotriazin-4(3H)-one

A) 6-bromo-3-(trans-2-hydroxycyclopentyl)-7,8-dimethylbenzo[d][1,2,3]triazin-4(3H)-one To a mixture of 2-amino-5-bromo-N-(trans-2-hydroxycyclopentyl)-3,4-dimethylbenzamide (1.34 g), 6N hydrochloric acid (4.5 mL) and water (15 mL) was added dropwise a solution of sodium nitrite (0.30 g) in water (3.5 mL) under ice-cooling, and the mixture was stirred for 2.5 hr. The reaction mixture was neutralized with 8N aqueous sodium hydroxide solution, and the precipitate was collected by filtration to give the title compound (1.35 g). Further purification was not performed and the compound was used in the next step.

$^1$H NMR (300 MHz, CDCl$_3$) δ1.75-1.89 (1H, m), 1.97 (2H, dt, J=14.5, 7.0 Hz), 2.14-2.31 (2H, m), 2.34-2.42 (1H, m), 2.61 (3H, s), 2.71 (1H, brs), 2.87 (3H, s), 4.48-4.62 (1H, m), 5.16 (1H, td, J=8.3, 5.5 Hz), 8.43 (1H, s).

B) 3-(trans-2-hydroxycyclopentyl)-7,8-dimethyl-6-(4,4,5,5-tetramethyl-1,3,2-dioxaborolan-2-yl)benzo[d][1,2,3]triazin-4(3H)-one To a mixture of bis(pinacolato)diboron (1.06 g), potassium acetate (1.18 g), 6-bromo-3-(trans-2-hydroxycyclopentyl)-7,8-dimethylbenzo[d][1,2,3]triazin-4(3H)-one (1.35 g) and toluene (30 mL) was added bis(triphenylphosphine)palladium(II) chloride (0.14 g), and the mixture was stirred under an argon atmosphere at 110° C. overnight. To the reaction mixture were added a 5% aqueous sodium hydrogen carbonate solution and ethyl acetate, and the precipitated crude crystal of the object product was collected by filtration. The filtrate was extracted with ethyl acetate and the organic layer was washed with saturated brine and dried over anhydrous sodium sulfate. The solvent was evaporated under reduced pressure. The residue and the earlier crude crystal were combined to give the title compound (0.75 g).

MS: [M+H]$^+$ 386.0

C) 3-(trans-2-hydroxycyclopentyl)-7,8-dimethyl-6-(4-(1-methyl-1H-1,2,3-triazol-4-yl)benzyl)-1,2,3-benzotriazin-4(3H)-one To a mixture of 3-(trans-2-hydroxycyclopentyl)-7,8-dimethyl-6-(4,4,5,5-tetramethyl-1,3,2-dioxaborolan-2-yl)benzo[d][1,2,3]triazin-4(3H)-one (0.25 g), sodium carbonate (0.14 g), 4-(4-(bromomethyl)phenyl)-1-methyl-1H-1,2,3-triazole (0.16 g), DME (3.0 mL) and water (1.0 mL) was added tetrakis(triphenylphosphine)palladium(0) (0.04 g), and the mixture was stirred under an argon atmosphere at 85° C. overnight. The reaction mixture was diluted with ethyl acetate and dried over anhydrous sodium sulfate. The solvent was evaporated under reduced pressure. The residue was purified by silica gel column chromatography (ethyl acetate/hexane) and recrystallized from ethyl acetate-hexane to give the title compound (0.16 g).

$^1$H NMR (300 MHz, CDCl$_3$) δ1.77-1.89 (1H, m), 1.91-2.01 (2H, m), 2.15-2.30 (1H, m), 2.30-2.43 (5H, m), 2.78-2.84 (4H, m), 4.14 (3H, s), 4.23 (2H, s), 4.46-4.64 (1H, m), 5.16 (1H, td, J=8.3, 5.7 Hz), 7.16 (2H, d, J=8.2 Hz), 7.67-7.78 (3H, m), 8.06 (1H, s).

Example 41

3-((3S,4S)-4-hydroxytetrahydro-2H-pyran-3-yl)-7,8-dimethyl-6-(4-(1H-pyrazol-1-yl)benzyl)-1,2,3-benzotriazin-4(3H)-one synonym: 1,5-anhydro-2,4-dideoxy-2-(7,8-dimethyl-4-oxo-6-(4-(1H-pyrazol-1-yl)benzyl)-1,2,3-benzotriazin-3(4H)-yl)-threo-pentitol

A) 6-bromo-3-(trans-4-hydroxytetrahydro-2H-pyran-3-yl)-7,8-dimethyl-1,2,3-benzotriazin-4(3H)-one To a mixture of 2-amino-5-bromo-N-(trans-4-hydroxytetrahydro-2H-pyran-3-yl)-3,4-dimethylbenzamide (1.01 g), 6N hydrochloric acid (3.22 mL) and water (10 mL) was added dropwise under ice-cooling a solution of sodium nitrite (0.21 g) in water (2.2 mL), and the mixture was stirred for 2.5 hr. The reaction mixture was neutralized with 8N aqueous sodium hydroxide solution and the precipitate was collected by filtration to give the title compound (0.99 g).

MS: [M+H]$^+$ 353.2, 355.0

B) 3-(trans-4-hydroxytetrahydro-2H-pyran-3-yl)-7,8-dimethyl-6-(4,4,5,5-tetramethyl-1,3,2-dioxaborolan-2-yl)-1,2,3-benzotriazin-4(3H)-one To a mixture of bis(pinacolato)diboron (0.45 g), potassium acetate (0.50 g), 6-bromo-3-(trans-4-hydroxytetrahydro-2H-pyran-3-yl)-7,8-dimethyl-1,2,3-benzotriazin-4(3H)-one (0.60 g) and toluene (15 mL) was added bis(triphenylphosphine)palladium(II) chloride (0.06 g), and the mixture was stirred under an argon atmosphere at 110° C. overnight. To the reaction mixture was added a 5% aqueous sodium hydrogen carbonate solution, and the mixture was extracted with ethyl acetate. The organic layer was washed with saturated brine, and dried over anhydrous sodium sulfate and the solvent was evaporated under reduced pressure. The residue was recrystallized from ethyl acetate-hexane to give the title compound (0.40 g).

MS: [M+H]⁺ 402.2

C) 3-((3S,4S)-4-hydroxytetrahydro-2H-pyran-3-yl)-7,8-dimethyl-6-(4-(1H-pyrazol-1-yl)benzyl)-1,2,3-benzotriazin-4(3H)-one synonym: 1,5-anhydro-2,4-dideoxy-2-(7,8-dimethyl-4-oxo-6-(4-(1H-pyrazol-1-yl)benzyl)-1,2,3-benzotriazin-3(4H)-yl)-threo-pentitol To a mixture of 3-(trans-4-hydroxytetrahydro-2H-pyran-3-yl)-7,8-dimethyl-6-(4,4,5,5-tetramethyl-1,3,2-dioxaborolan-2-yl)-1,2,3-benzotriazin-4(3H)-one (0.20 g), sodium carbonate (0.11 g), 1-(4-(bromomethyl)phenyl)-1H-pyrazole (0.12 g), DME (3.0 mL) and water (1.0 mL) was added tetrakis(triphenylphosphine)palladium(0) (0.03 g), and the mixture was stirred under an argon atmosphere at 85° C. for 1 hr. The reaction mixture was diluted with ethyl acetate and dried over anhydrous sodium sulfate. The solvent was evaporated under reduced pressure. The residue was purified by silica gel column chromatography (ethyl acetate/hexane) and recrystallized from ethyl acetate-hexane to give the title compound (0.15 g).

¹H NMR (300 MHz, CDCl₃) δ1.83-2.02 (1H, m), 2.07 (1H, d, J=6.4 Hz), 2.23 (1H, dd, J=13.0, 5.1 Hz), 2.36 (3H, s), 2.80 (3H, s), 3.54-3.65 (1H, m), 3.82 (1H, t, J=10.8 Hz), 4.02-4.20 (2H, m), 4.23 (2H, s), 4.45-4.60 (1H, m), 5.09 (1H, td, J=10.3, 4.6 Hz), 6.38-6.49 (1H, m), 7.14-7.21 (2H, m), 7.56-7.65 (2H, m), 7.71 (1H, d, J=1.5 Hz), 7.88 (1H, d, J=2.4 Hz), 8.06 (1H, s).

Example 42

3-(trans-4-hydroxytetrahydro-2H-pyran-3-yl)-6-((6-(1H-imidazol-1-yl)pyridin-3-yl)methyl)-7,8-dimethyl-1,2,3-benzotriazin-4(3H)-one Synonym: 1,5-anhydro-2,4-dideoxy-2-(6-((6-(1H-imidazol-1-yl)pyridin-3-yl)methyl)-7,8-dimethyl-4-oxo-1,2,3-benzotriazin-3(4H)-yl)-threo-pentitol

A) 6-(1H-imidazol-1-yl)pyridine-3-carbaldehyde

A mixture of 6-chloropyridine-3-carbaldehyde (19.3 g), imidazole (11.1 g) and potassium carbonate (37.5 g) in DMF (200 mL) was heated at 100° C. for 16 hr. After cooling to room temperature, the reaction mixture was concentrated under reduced pressure. To the residue was added dichloromethane and the mixture was washed twice with water. The organic layer was dried over anhydrous sodium sulfate, and the solvent was evaporated under reduced pressure. The residue was purified by silica gel column chromatography (ethyl acetate) to give the title compound (10.0 g).

¹H NMR (400 MHz, CDCl₃) δ7.24 (1H, s), 7.50 (1H, d, J=8.8 Hz), 7.71 (1H, s), 8.31 (1H, dd, J=8.8, 2.4 Hz), 8.46 (1H, s), 8.94 (1H, d, J=2.0 Hz), 10.10 (1H, s).

B) (6-(1H-imidazol-1-yl)pyridin-3-yl)methanol

To a mixture of 6-(1H-imidazol-1-yl)pyridine-3-carbaldehyde (10.0 g) and methanol (100 mL) was added sodium borohydride (3.29 g) under ice-cooling, and the mixture was stirred at the same temperature for 1 hr. To the reaction mixture was added water, and the mixture was diluted with dichloromethane-isopropanol (10:1). The precipitate was collected by filtration and dried under reduced pressure to give the title compound (8.50 g).

¹H NMR (400 MHz, CDCl₃) δ4.57 (2H, d, J=5.2 Hz), 5.39 (1H, t, J=5.6 Hz), 7.12 (1H, s), 7.78 (1H, d, J=8.4 Hz), 7.85-7.97 (2H, m), 8.43 (1H, d, J=1.2 Hz), 8.51 (1H, s).

C) 5-(bromomethyl)-2-(1H-imidazol-1-yl)pyridine phosphate

To a mixture of (6-(1H-imidazol-1-yl)pyridin-3-yl)methanol (3.92 g) and dichloromethane (50 mL) was added phosphorus tribromide (6.07 g) at 0° C., and the mixture was stirred at 23° C. for 16 hr. The reaction mixture was filtered, and the solid collected by filtration was washed with dichloromethane and dried under reduced pressure to give the title compound (5.28 g).

¹H NMR (400 MHz, CDCl₃) δ4.85 (2H, s), 7.93 (1H, s), 8.08 (1H, d, J=8.8 Hz), 8.28 (1H, dd, J=8.4, 2.4 Hz), 8.48 (1H, s), 8.73 (1H, d, J=1.6 Hz), 9.97 (1H, s).

D) 3-(trans-4-hydroxytetrahydro-2H-pyran-3-yl)-6-((6-(1H-imidazol-1-yl)pyridin-3-yl)methyl)-7,8-dimethyl-1,2,3-benzotriazin-4 (3H)-one Synonym: 1,5-anhydro-2,4-dideoxy-2-(6-((6-(1H-imidazol-1-yl)pyridin-3-yl)methyl)-7,8-dimethyl-4-oxo-1,2,3-benzotriazin-3(4H)-yl)-threo-pentitol To a mixture of 3-(trans-4-hydroxytetrahydro-2H-pyran-3-yl)-7,8-dimethyl-6-(4,4,5,5-tetramethyl-1,3,2-dioxaborolan-2-yl)-1,2,3-benzotriazin-4(3H)-one (0.20 g), sodium carbonate (0.53 g), DME (3.0 mL) and water (1.0 mL) were added 5-(bromomethyl)-2-(1H-imidazol-1-yl)pyridine phosphate (0.25 g) and tetrakis(triphenylphosphine)palladium(0) (0.03 g), and the mixture was stirred under an argon atmosphere at 85° C. for 1 hr. To the reaction mixture was added a 5% aqueous sodium hydrogen carbonate solution, and the mixture was extracted with ethyl acetate. The organic layer was washed with saturated brine and dried over anhydrous sodium sulfate. The solvent was evaporated under reduced pressure. The residue was purified by silica gel column chromatography (methanol/ethyl acetate) and recrystallized from methanol-ethyl acetate-hexane to give the title compound (0.05 g).

¹H NMR (300 MHz, CDCl₃) δ1.85-2.01 (1H, m), 2.04-2.10 (1H, m), 2.23 (1H, dd, J=13.1, 4.6 Hz), 2.39 (3H, s), 2.81 (3H, s), 3.52-3.65 (1H, m), 3.82 (1H, t, J=10.8 Hz), 4.14 (2H, td, J=11.0, 5.0 Hz), 4.23 (2H, s), 4.42-4.58 (1H, m), 5.09 (1H, td, J=10.3, 4.9 Hz), 7.19 (1H, s), 7.29 (1H, s), 7.51 (1H, dd, J=8.2, 2.2 Hz), 7.60 (1H, d, J=1.5 Hz), 8.04 (1H, s), 8.30 (2H, s).

Example 43

3-((3S,4S)-4-hydroxytetrahydro-2H-pyran-3-yl)-7,8-dimethyl-6-(4-(1H-pyrazol-1-yl)benzyl)-1,2,3-benzotriazin-4(3H)-one synonym: 1,5-anhydro-2,4-dideoxy-2-(7,8-dimethyl-4-oxo-6-(4-(1H-pyrazol-1-yl)benzyl)-1,2,3-benzotriazin-3(4H)-yl)-L-threo-pentitol

A) 2-amino-5-bromo-N-((3S,4S)-4-hydroxytetrahydro-2H-pyran-3-yl)-3,4-dimethylbenzamide A mixture of 2-amino-5-bromo-3,4-dimethylbenzoic acid (0.42 g), (3S,4S)-3-aminotetrahydro-2H-pyran-4-ol (0.20 g), triethylamine (0.43 g), WSC hydrochloride (0.39 g) and HOBt (anhydride) (0.28 g) in DMF (8 mL) was stirred at room temperature overnight. To the reaction mixture was added a 5% aqueous sodium hydrogen carbonate solution, and the mixture was extracted with ethyl acetate. The organic layer was washed with saturated brine and dried over anhydrous sodium sulfate. The solvent was evaporated under reduced pressure to give the title compound (0.59 g; containing DMF). Further purification was not performed and the compound was used in the next step.
MS: [M+H]$^+$ 343.1, 345.1

B) 6-bromo-3-((3S,4S)-4-hydroxytetrahydro-2H-pyran-3-yl)-7,8-dimethylbenzo[d][1,2,3]triazin-4(3H)-one To a mixture of 2-amino-5-bromo-N-((3S,4S)-4-hydroxytetrahydro-2H-pyran-3-yl)-3,4-dimethylbenzamide (0.59 g; containing DMF), 6N hydrochloric acid (1.88 mL) and water (6 mL) was added dropwise under ice-cooling a solution of sodium nitrite (0.12 g) in water (1.3 mL), and the mixture was stirred for 1 hr. The reaction mixture was neutralized with 8N aqueous sodium hydroxide solution and the precipitate was collected by filtration to give the title compound (0.50 g).
$^1$H NMR (300 MHz, CDCl$_3$) δ1.82-2.00 (1H, m), 2.00-2.15 (1H, m), 2.15-2.29 (1H, m), 2.61 (3H, s), 2.82-2.89 (3H, m), 3.58 (1H, td, J=12.2, 2.1 Hz), 3.79 (1H, t, J=10.8 Hz), 4.05-4.18 (2H, m), 4.48 (1H, td, J=10.4, 5.0 Hz), 5.07 (1H, td, J=10.3, 4.7 Hz), 8.43 (1H, s).

C) 3-((3S,4S)-4-hydroxytetrahydro-2H-pyran-3-yl)-7,8-dimethyl-6-(4,4,5,5-tetramethyl-1,3,2-dioxaborolan-2-yl)-1,2,3-benzotriazin-4(3H)-one To a mixture of bis(pinacolato)diboron (0.38 g), potassium acetate (0.42 g), 6-bromo-3-((3S,4S)-4-hydroxytetrahydro-2H-pyran-3-yl)-7,8-dimethylbenzo[d][1,2,3]triazin-4(3H)-one (0.50 g) and toluene (10 mL) was added bis(triphenylphosphine)palladium(II) chloride (0.05 g), and the mixture was stirred under an argon atmosphere at 110° C. for 4 hr. To the reaction mixture was added a 5% aqueous sodium hydrogen carbonate solution, and the mixture was extracted with ethyl acetate. The organic layer was washed with saturated brine and dried over anhydrous sodium sulfate. The solvent was evaporated under reduced pressure. The residue was crystallized from ethyl acetate-hexane to give the title compound (0.50 g).
MS: [M+H]$^+$ 402.2

D) 3-((3S,4S)-4-hydroxytetrahydro-2H-pyran-3-yl)-7,8-dimethyl-6-(4-(1H-pyrazol-1-yl)benzyl)-1,2,3-benzotriazin-4(3H)-one synonym: 1,5-anhydro-2,4-dideoxy-2-(7,8-dimethyl-4-oxo-6-(4-(1H-pyrazol-1-yl)benzyl)-1,2,3-benzotriazin-3(4H)-yl)-L-threo-pentitol To a mixture of 3-((3S,4S)-4-hydroxytetrahydro-2H-pyran-3-yl)-7,8-dimethyl-6-(4,4,5,5-tetramethyl-1,3,2-dioxaborolan-2-yl)-1,2,3-benzotriazin-4(3H)-one (0.10 g), sodium carbonate (0.05 g), 1-(4-(bromomethyl)phenyl)-1H-pyrazole (0.06 g), DME (1.5 mL) and water (0.5 mL) was added tetrakis(triphenylphosphine)palladium(0) (0.01 g), and the mixture was stirred under an argon atmosphere at 85° C. for 1 hr. The reaction mixture was diluted with ethyl acetate and dried over anhydrous sodium sulfate. The solvent was evaporated under reduced pressure. The residue was purified by silica gel column chromatography (ethyl acetate/hexane) wand recrystallized from ethyl acetate-hexane to give the title compound (0.08 g).
$^1$H NMR (300 MHz, CDCl$_3$) δ1.84-2.01 (1H, m), 2.06 (1H, d, J=6.5 Hz), 2.16-2.28 (1H, m), 2.36 (3H, s), 2.80 (3H, s), 3.53-3.65 (1H, m), 3.82 (1H, t, J=10.8 Hz), 4.05-4.21 (2H, m), 4.23 (2H, s), 4.40-4.58 (1H, m), 5.09 (1H, td, J=10.3, 4.7 Hz), 6.41-6.49 (1H, m), 7.13-7.22 (2H, m), 7.55-7.65 (2H, m), 7.71 (1H, d, J=1.5 Hz), 7.88 (1H, d, J=2.0 Hz), 8.06 (1H, s).

Example 47

3-((3S,4S)-4-hydroxytetrahydro-2H-pyran-3-yl)-7,8-dimethyl-6-(4-(1-methyl-1H-pyrazol-3-yl)benzyl)-1,2,3-benzotriazin-4(3H)-one Synonym: 1,5-anhydro-2,4-dideoxy-2-(7,8-dimethyl-6-(4-(1-methyl-1H-pyrazol-3-yl)benzyl)-4-oxo-1,2,3-benzotriazin-3(4H)-yl)-L-threo-pentitol To a mixture of 3-((3S,4S)-4-hydroxytetrahydro-2H-pyran-3-yl)-7,8-dimethyl-6-(4,4,5,5-tetramethyl-1,3,2-dioxaborolan-2-yl)-1,2,3-benzotriazin-4(3H)-one (0.26 g), sodium carbonate (0.17 g), 3-(4-(chloromethyl)phenyl)-1-methyl-1H-pyrazole (0.15 g), DME (2.0 mL) and water (0.67 mL) was added tetrakis(triphenylphosphine)palladium (0) (0.04 g), and the mixture was stirred under an argon atmosphere at 85° C. for 4 hr. The reaction mixture was diluted with ethyl acetate and dried over anhydrous sodium sulfate. The solvent was evaporated under reduced pressure. The residue was purified by silica gel column chromatography (ethyl acetate/hexane) and recrystallized from ethyl acetate-hexane to give the title compound (0.19 g).
$^1$H NMR (300 MHz, CDCl$_3$) δ1.85-2.03 (1H, m), 2.07 (1H, d, J=6.5 Hz), 2.23 (1H, dd, J=12.9, 5.0 Hz), 2.35 (3H, s), 2.79 (3H, s), 3.51-3.66 (1H, m), 3.72-3.86 (1H, m), 3.94 (3H, s), 4.04-4.26 (4H, m), 4.40-4.60 (1H, m), 5.09 (1H, td, J=10.3, 4.5 Hz), 6.49 (1H, d, J=2.3 Hz), 7.05-7.14 (2H, m), 7.36 (1H, d, J=2.2 Hz), 7.64-7.75 (2H, m), 8.07 (1H, s).

Example 49

8-fluoro-3-((3S,4S)-4-hydroxytetrahydro-2H-pyran-3-yl)-7-methyl-6-(4-(1H-pyrazol-1-yl)benzyl)-1,2,3-benzotriazin-4(3H)-one Synonym: 1,5-anhydro-2,4-dideoxy-2-(8-fluoro-7-methyl-4-oxo-6-(4-(1H-pyrazol-1-yl)benzyl)-1,2,3-benzotriazin-3(4H)-yl)-L-threo-pentitol To a mixture of 5-(4-(1H-pyrazol-1-yl)benzyl)-2-amino-3-fluoro-N-((3S,4S)-4-hydroxytetrahydro-2H-pyran-3-yl)-4-methylbenzamide (0.06 g) and 2N hydrochloric acid (0.42 mL) was added under ice-cooling a solution of sodium nitrite (0.01 g) in water (1.0 mL), and the mixture was stirred at the same temperature for 3 hr. The reaction mixture was neutralized with 8N aqueous sodium hydroxide solution under ice-cooling and the precipitate was collected by filtration. The residue was purified by silica gel column chromatography (ethyl acetate/hexane) and triturated with ethanol to give the title compound (0.03 g).
$^1$H NMR (300 MHz, CDCl$_3$) δ1.53-1.79 (1H, m), 1.98-2.09 (1H, m), 2.39 (3H, d, J=2.5 Hz), 3.39-3.73 (3H, m), 3.87-4.00 (2H, m), 4.25 (1H, dd, J=10.1, 5.2 Hz), 4.31 (2H, s), 4.74-4.89 (1H, m), 5.19 (1H, d, J=4.7 Hz), 6.53 (1H, dd,

Example 50

3-(trans-2-hydroxycyclopentyl)-7,8-dimethyl-6-((6-(1-methyl-1H-pyrazol-4-yl)pyridin-3-yl)methyl)quinazolin-4(3H)-one (optical isomer: retention time short)

3-(trans-2-Hydroxycyclopentyl)-7,8-dimethyl-6-((6-(1-methyl-1H-pyrazol-4-yl)pyridin-3-yl)methyl)quinazolin-4(3H)-one (0.06 g) was optically resolved by SFC (CHIRALCEL IB, 50 mmID×500 mmL, mobile phase: carbon dioxide/methanol=700/300) and triturated with ethyl acetate-diisopropyl ether to give the title compound (0.02 g) having a shorter retention time (tR1).

$^1$H NMR (300 MHz, DMSO-$d_6$) δ1.43-1.64 (1H, m), 1.67-2.15 (5H, m), 2.30 (3H, s), 2.53 (3H, s), 3.87 (3H, s), 4.14 (2H, s), 4.43 (1H, dd, J=7.2, 5.1 Hz), 4.52-4.71 (1H, m), 5.05 (1H, d, J=4.9 Hz), 7.41-7.49 (1H, m), 7.52-7.60 (1H, m), 7.75-8.44 (5H, m).

Example 51

3-(trans-2-hydroxycyclopentyl)-7,8-dimethyl-6-((6-(1-methyl-1H-pyrazol-4-yl)pyridin-3-yl)methyl)quinazolin-4(3H)-one (optical isomer: retention time long)

3-(trans-2-Hydroxycyclopentyl)-7,8-dimethyl-6-((6-(1-methyl-1H-pyrazol-4-yl)pyridin-3-yl)methyl)quinazolin-4(3H)-one (0.06 g) was optically resolved by SFC (CHIRALCEL IB, 50 mmID×500 mmL, mobile phase: carbon dioxide/methanol=700/300) and triturated with ethyl acetate-diisopropyl ether to give the title compound (0.02 g) having a longer retention time (tR2).

$^1$H NMR (300 MHz, DMSO-$d_6$) δ1.43-1.63 (1H, m), 1.66-2.12 (5H, m), 2.30 (3H, s), 2.53 (3H, s), 3.87 (3H, s), 4.14 (2H, s), 4.35-4.51 (1H, m), 4.54-4.69 (1H, m), 5.05 (1H, d, J=4.9 Hz), 7.39-7.49 (1H, m), 7.52-7.60 (1H, m), 7.73-8.45 (5H, m).

Example 52

3-(trans-4-hydroxytetrahydro-2H-pyran-3-yl)-7,8-dimethyl-6-(4-(1H-pyrazol-1-yl)benzyl)quinazolin-4(3H)-one (optical isomer: retention time short)

Synonym: 1,5-anhydro-2,4-dideoxy-2-(7,8-dimethyl-4-oxo-6-(4-(1H-pyrazol-1-yl)benzyl)quinazolin-3(4H)-yl)-threo-pentitol (optical isomer: retention time short)

3-(trans-4-Hydroxytetrahydro-2H-pyran-3-yl)-7,8-dimethyl-6-(4-(1H-pyrazol-1-yl)benzyl)quinazolin-4(3H)-one (0.03 g) was optically resolved by HPLC (CHIRALPAK IC, 50 mmID×500 mmL, mobile phase: ethanol) and triturated with ethyl acetate to give the title compound (0.01 g) having a shorter retention time (tR1).

$^1$H NMR (300 MHz, DMSO-$d_6$) δ1.49-1.72 (1H, m), 1.93-2.07 (1H, m), 2.29 (3H, s), 2.52 (3H, brs), 3.46 (1H, t, J=11.2 Hz), 3.59-3.74 (1H, m), 3.77-3.97 (2H, m), 4.19 (2H, s), 4.22-4.33 (1H, m), 4.34-4.50 (1H, m), 5.21 (1H, d, J=5.3 Hz), 6.49-6.56 (1H, m), 7.19-7.29 (2H, m), 7.71 (1H, d, J=1.7 Hz), 7.72-7.78 (2H, m), 7.82 (1H, s), 8.38 (1H, s), 8.43 (1H, d, J=2.5 Hz).

Example 53

3-(trans-4-hydroxytetrahydro-2H-pyran-3-yl)-7,8-dimethyl-6-(4-(1H-pyrazol-1-yl)benzyl)quinazolin-4(3H)-one (optical isomer: retention time long)

Synonym: 1,5-anhydro-2,4-dideoxy-2-(7,8-dimethyl-4-oxo-6-(4-(1H-pyrazol-1-yl)benzyl)quinazolin-3(4H)-yl)-threo-pentitol (optical isomer: retention time long)

3-(trans-4-hydroxytetrahydro-2H-pyran-3-yl)-7,8-dimethyl-6-(4-(1H-pyrazol-1-yl)benzyl)quinazolin-4(3H)-one (0.03 g) was optically resolved by HPLC (CHIRALPAK IC, 50 mmID×500 mmL, mobile phase: ethanol) and triturated with ethyl acetate to give the title compound (0.01 g) having a longer retention time (tR2).

$^1$H NMR (300 MHz, DMSO-$d_6$) δ1.48-1.70 (1H, m), 1.95-2.06 (1H, m), 2.29 (3H, s), 2.52 (3H, s), 3.38-3.54 (1H, m), 3.60-3.74 (1H, m), 3.78-3.95 (2H, m), 4.19 (2H, s), 4.21-4.32 (1H, m), 4.40 (1H, brs), 5.21 (1H, d, J=5.5 Hz), 6.52 (1H, dd, J=2.5, 1.9 Hz), 7.16-7.31 (2H, m), 7.71 (1H, d, J=1.5 Hz), 7.72-7.78 (2H, m), 7.82 (1H, s), 8.38 (1H, s), 8.43 (1H, d, J=2.5 Hz).

Example 54

6-((6-chloropyridin-3-yl)methyl)-3-((1S,2S)-2-hydroxycyclohexyl)-7,8-dimethylquinazolin-4(3H)-one A) 2-amino-5-bromo-N-((1S,2S)-2-hydroxycyclohexyl)-3,4-dimethylbenzamide A mixture of 2-amino-5-bromo-3,4-dimethylbenzoic acid (1.91 g), (1S,2S)-2-aminocyclohexanol (0.99 g), HOBt monohydrate (1.20 g), WSC hydrochloride (1.80 g) and DMF (30 mL) was stirred at room temperature overnight. To the reaction mixture was added water at room temperature and the precipitate was collected by filtration. The precipitate was washed with water and dried under reduced pressure to give the title compound (2.63 g).

MS: [M+H]$^+$ 341.0, 343.0

B) 6-bromo-3-((1S,2S)-2-hydroxycyclohexyl)-7,8-dimethylquinazolin-4(3H)-one

A mixture of 2-amino-5-bromo-N-((1S,2S)-2-hydroxycyclohexyl)-3,4-dimethylbenzamide (2.63 g) and N,N-dimethylformamide dimethyl acetal (10.2 mL) was stirred at 90° C. overnight. The reaction mixture was concentrated under reduced pressure, water was added to the residue and the mixture was stirred at room temperature for 10 min. The solid was collected by filtration, washed with water and dried under reduced pressure to give the title compound (2.39 g).

MS: [M+H]$^+$ 351.0, 353.0

C) 6-((6-chloropyridin-3-yl)methyl)-3-((1S,2S)-2-hydroxycyclohexyl)-7,8-dimethylquinazolin-4(3H)-one To a mixture of 6-bromo-3-((1S,2S)-2-hydroxycyclohexyl)-7,8-dimethylquinazolin-4(3H)-one (1.0 g), bis(tri-tert-butylphosphine)palladium(0) (0.07 g) and THF (10 mL) was added (6-chloro-3-pyridyl)methylzinc chloride (0.5 M THF solution) (7.97 mL), and the mixture was stirred under an argon atmosphere at 80° C. overnight. To the reaction mixture was added water, and insoluble material was filtered off through celite. The filtrate was extracted with a mixed solution of ethyl acetate and THF. The organic layer was washed with water and saturated brine, and dried over anhydrous magnesium sulfate and the solvent was evaporated under reduced pressure. The residue was purified by silica gel column chromatography (ethyl acetate/hexane) to give the title compound (0.95 g).

$^1$H NMR (300 MHz, CDCl$_3$) δ1.33-1.54 (3H, m), 1.83-2.07 (4H, m), 2.18-2.23 (1H, m), 2.24 (3H, s), 2.55 (3H, s), 3.82-4.02 (1H, m), 4.10 (2H, s), 4.40-4.65 (1H, m), 7.16-7.23 (1H, m), 7.26 (1H, s), 7.32 (1H, dd, J=8.2, 2.5 Hz), 7.93 (1H, s), 8.10 (1H, s), 8.23 (1H, d, J=2.1 Hz).

Example 55

3-((3R,4S)-3-hydroxytetrahydro-2H-pyran-4-yl)-7,8-dimethyl-6-(4-(1H-pyrazol-1-yl)benzyl)quinazolin-4(3H)-one Synonym: 1,5-anhydro-2,3-dideoxy-3-(7,8-dimethyl-4-oxo-6-(4-(1H-pyrazol-1-yl)benzyl)quinazolin-3(4H)-yl)-L-threo-pentitol A) methyl 2-amino-5-bromo-3,4-dimethylbenzoate To a mixed solution of 2-amino-5-bromo-3,4-dimethylbenzoic acid (3.0 g) and DMF (50 mL) was added cesium carbonate (6.01 g), and the mixture was stirred at room temperature for 30 min. To the reaction solution was added methyl iodide (2.09 g), and the mixture was stirred at room temperature overnight. To the reaction mixture was added water, and the mixture was extracted with ethyl acetate. The organic layer was washed with water, and dried over anhydrous magnesium sulfate and the solvent was evaporated under reduced pressure. The residue was purified by silica gel column chromatography (ethyl acetate/hexane) to give the title compound (3.0 g).

MS: [M+H]$^+$ 257.8, 259.8

B) methyl 2-amino-3,4-dimethyl-5-(4,4,5,5-tetramethyl-1,3,2-dioxaborolan-2-yl)benzoate To a mixture of methyl 2-amino-5-bromo-3,4-dimethylbenzoate (3.7 g), bis(pinacolato)diboron (7.28 g), potassium acetate (4.22 g) and toluene (100 mL) was added bis(triphenylphosphine)palladium(II) chloride (1.01 g), and the mixture was stirred under an argon atmosphere at 110° C. overnight. Insoluble material was filtered off and the filtrate was concentrated under reduced pressure. The residue was purified by silica gel column chromatography (ethyl acetate/hexane) and triturated with ethyl acetate-hexane to give the title compound (0.7 g).

MS: [M+H]$^+$ 306.0

C) methyl 5-(4-(1H-pyrazol-1-yl)benzyl)-2-amino-3,4-dimethylbenzoate

To a mixture of methyl 2-amino-3,4-dimethyl-5-(4,4,5,5-tetramethyl-1,3,2-dioxaborolan-2-yl)benzoate (0.69 g), 1-(4-(chloromethyl)phenyl)-1H-pyrazole (0.46 g), 2 M aqueous sodium carbonate solution (2.26 mL) and DME (20 mL) was added (1,1-bis(diphenylphosphino)ferrocene)dichloropalladium(II) dichloromethane adduct (0.09 g) under an argon atmosphere and the mixture was stirred at 80° C. overnight. The reaction mixture was dried over anhydrous sodium sulfate and concentrated under reduced pressure. The residue was purified by silica gel column chromatography (ethyl acetate/hexane) to give the title compound (0.65 g).

MS: [M+H]$^+$ 336.1

D) 5-(4-(1H-pyrazol-1-yl)benzyl)-2-amino-3,4-dimethylbenzoic Acid

To a mixed solution of methyl 5-(4-(1H-pyrazol-1-yl)benzyl)-2-amino-3,4-dimethylbenzoate (0.65 g) and THF (5 mL)-methanol (5 mL) was added 8 M aqueous sodium hydroxide solution (2.42 mL), and the mixture was stirred at 60° C. for 5 hr. The reaction mixture was adjusted with 6 M hydrochloric acid to pH 4 under ice-cooling. The resulting precipitate was collected by filtration, washed with water and dried under reduced pressure to give the title compound (0.51 g).

MS: [M+H]$^+$ 322.1

E) 5-(4-(1H-pyrazol-1-yl)benzyl)-2-amino-N-((3R,4S)-3-hydroxytetrahydro-2H-pyran-4-yl)-3,4-dimethylbenzamide To a mixture of 5-(4-(1H-pyrazol-1-yl)benzyl)-2-amino-3,4-dimethylbenzoic acid (0.50 g), (3R,4S)-4-aminotetrahydro-2H-pyran-3-ol hydrochloride (0.25 g), WSC hydrochloride (0.36 g), HOBt monohydrate (0.26 g) and DMF (3 mL) was added triethylamine (0.32 g), and the mixture was stirred at room temperature for 4 hr. To the reaction mixture was added water, and the precipitate was collected by filtration, washed with water and dried under reduced pressure to give the title compound (0.65 g).

MS: [M+H]$^+$ 421.2

F) 3-((3R,4S)-3-hydroxytetrahydro-2H-pyran-4-yl)-7,8-dimethyl-6-(4-(1H-pyrazol-1-yl)benzyl)quinazolin-4(3H)-one Synonym: 1,5-anhydro-2,3-dideoxy-3-(7,8-dimethyl-4-oxo-6-(4-(1H-pyrazol-1-yl)benzyl)quinazolin-3(4H)-yl)-L-threo-pentitol A mixture of 5-(4-(1H-pyrazol-1-yl)benzyl)-2-amino-N-((3R,4S)-3-hydroxytetrahydro-2H-pyran-4-yl)-3,4-dimethylbenzamide (0.50 g) and N,N-dimethylformamide dimethyl acetal (1.6 mL) was stirred at 90° C. for 4 hr. The reaction mixture was concentrated under reduced pressure, water was added to the residue, and the mixture was stirred at room temperature for 10 min. The precipitate was collected by filtration, washed with water and dried under reduced pressure. The obtained solid was purified by silica gel column chromatography (ethyl acetate/hexane) and triturated with ethyl acetate to give the title compound (0.22 g).

$^1$H NMR (300 MHz, DMSO-d$_6$) δ1.78-1.91 (1H, m), 2.08-2.24 (1H, m), 2.29 (3H, s), 2.53 (3H, s), 3.11 (1H, t, J=10.4 Hz), 3.35-3.49 (1H, m), 3.85-4.00 (2H, m), 4.02-4.15 (1H, m), 4.19 (2H, s), 4.41-4.61 (1H, m), 5.23 (1H, d, J=5.5 Hz), 6.50-6.53 (1H, m), 7.20-7.29 (2H, m), 7.71 (1H, d, J=1.7 Hz), 7.72-7.77 (2H, m), 7.84 (1H, s), 8.39-8.48 (2H, m).

Example 56

3-((3R,4S)-3-hydroxytetrahydro-2H-pyran-4-yl)-7,8-dimethyl-6-(4-(1H-pyrazol-1-yl)benzyl)-1,2,3-benzotriazin-4(3H)-one Synonym: 1,5-anhydro-2,3-dideoxy-3-(7,8-dimethyl-4-oxo-6-(4-(1H-pyrazol-1-yl)benzyl)-1,2,3-benzotriazin-3(4H)-yl)-L-threo-pentitol To a mixture of 5-(4-(1H-pyrazol-1-yl)benzyl)-2-amino-N-((3R,4S)-3-hydroxytetrahydro-2H-pyran-4-yl)-3,4-dimethylbenzamide (0.15 g) and 2 M hydrochloric acid (1.07 mL) was added dropwise under ice-cooling a solution of sodium nitrite (0.03 g) in water (1.0 mL), and the mixture was stirred at room temperature for 3 hr. The reaction mixture was neutralized with 8 M aqueous sodium hydroxide solution under ice-cooling, and the precipitate was collected by filtration. The obtained solid was further purified by silica gel column chromatography (ethyl acetate/hexane) and triturated with ethyl acetate to give the title compound (0.15 g).

$^1$H NMR (300 MHz, DMSO-$d_5$) δ1.93 (1H, dd, J=12.8, 4.3 Hz), 2.13 (1H, qd, J=12.5, 4.6 Hz), 2.38 (3H, s), 2.76 (3H, s), 3.20 (1H, t, J=10.7 Hz), 3.44-3.56 (1H, m), 3.88-4.01 (2H, m), 4.10 (1H, ddt, J=15.1, 10.1, 5.0 Hz), 4.30 (2H, s), 4.97 (1H, ddd, J=11.9, 9.8, 4.5 Hz), 5.21 (1H, d, J=5.1 Hz), 6.52 (1H, dd, J=2.5, 1.7 Hz), 7.22-7.30 (2H, m), 7.71 (1H, d, J=1.3 Hz), 7.74-7.81 (2H, m), 7.93 (1H, s), 8.44 (1H, dd, J=2.5, 0.4 Hz).

Example 57

3-((1S,2S)-2-hydroxycyclohexyl)-7,8-dimethyl-6-((6-(1-methyl-1H-pyrazol-3-yl)pyridin-3-yl)methyl)quinazolin-4(3H)-one To a mixture of 6-((6-chloropyridin-3-yl)methyl)-3-((1S,2S)-2-hydroxycyclohexyl)-7,8-dimethylquinazolin-4(3H)-one (0.10 g), 1-methyl-3-(4,4,5,5-tetramethyl-1,3,2-dioxaborolan-2-yl)-1H-pyrazole (0.06 g), 2 M aqueous sodium carbonate solution (0.25 mL) and DME (3.0 mL) was added tetrakis(triphenylphosphine)palladium(0) (0.01 g) under an argon atmosphere and the mixture was stirred at 90° C. overnight. The reaction mixture was dried over anhydrous sodium sulfate and concentrated under reduced pressure. The residue was purified by silica gel column chromatography (ethyl acetate/hexane) and triturated with ethyl acetate to give the title compound (0.07 g).

$^1$H NMR (300 MHz, DMSO-$d_6$) δ1.23-1.43 (3H, m), 1.64-1.86 (4H, m), 1.96-2.07 (1H, m), 2.29 (3H, s), 2.52 (3H, s), 3.89 (3H, s), 3.92-4.00 (1H, m), 4.18 (2H, s), 4.25-4.50 (1H, m), 4.89 (1H, d, J=5.3 Hz), 6.75 (1H, d, J=2.3 Hz), 7.47 (1H, dd, J=8.1, 2.3 Hz), 7.74 (1H, d, J=2.3 Hz), 7.78-7.86 (2H, m), 8.38 (1H, s), 8.43 (1H, d, J=1.7 Hz).

Example 58

3-((3S,4S)-4-hydroxytetrahydro-2H-pyran-3-yl)-7,8-dimethyl-6-((6-(1-methyl-1H-pyrazol-3-yl)pyridin-3-yl)methyl)-1,2,3-benzotriazin-4(3H)-one Synonym: 1,5-anhydro-2,4-dideoxy-2-(7,8-dimethyl-6-((6-(1-methyl-1H-pyrazol-3-yl)pyridin-3-yl)methyl)-4-oxo-1,2,3-benzotriazin-3(4H)-yl)-L-threo-pentitol A) 6-((6-chloropyridin-3-yl)methyl)-3-((3S,4S)-4-hydroxytetrahydro-2H-pyran-3-yl)-7,8-dimethyl-benzo[d][1,2,3]triazin-4(3H)-one To a mixture of 6-bromo-3-((3S,4S)-4-hydroxytetrahydro-2H-pyran-3-yl)-7,8-dimethylbenzo[d][1,2,3]triazin-4(3H)-one (0.44 g), bis(tri-tert-butylphosphine)palladium(0) (0.03 g) and THF (1.0 mL) was added (6-chloro-3-pyridyl)methylzinc chloride (0.5 M THF solution) (5.0 mL), and the mixture was stirred under an argon atmosphere at 80° C. overnight. To the reaction mixture was added water, and the mixture was extracted with a mixed solution of ethyl acetate and THF. The organic layer was washed with water and saturated brine, and dried over anhydrous magnesium sulfate and the solvent was evaporated under reduced pressure. The residue was purified by silica gel column chromatography (ethyl acetate/hexane) to give the title compound (0.20 g).

MS: [M+H]$^+$ 401.2

B) 3-((3S,4S)-4-hydroxytetrahydro-2H-pyran-3-yl)-7,8-dimethyl-6-((6-(1-methyl-1H-pyrazol-3-yl)pyridin-3-yl)methyl)-1,2,3-benzotriazin-4(3H)-one Synonym: 1,5-anhydro-2,4-dideoxy-2-(7,8-dimethyl-6-((6-(1-methyl-1H-pyrazol-3-yl)pyridin-3-yl)methyl)-4-oxo-1,2,3-benzotriazin-3(4H)-yl)-L-threo-pentitol To a mixture of 6-((6-chloropyridin-3-yl)methyl)-3-((3S,4S)-4-hydroxytetrahydro-2H-pyran-3-yl)-7,8-dimethyl-benzo[d][1,2,3]triazin-4(3H)-one (0.06 g), 1-methyl-3-(4,4,5,5-tetramethyl-1,3,2-dioxaborolan-2-yl)-1H-pyrazole (0.04 g), 2 M aqueous sodium carbonate solution (0.14 mL) and DME (3.0 mL) was added tetrakis(triphenylphosphine)palladium(0) (0.01 g) under an argon atmosphere, and the mixture was stirred at 90° C. overnight. The reaction mixture was dried over anhydrous sodium sulfate and concentrated under reduced pressure. The residue was purified by silica gel column chromatography (ethyl acetate/hexane) and triturated with ethyl acetate to give the title compound (0.03 g).

$^1$H NMR (300 MHz, DMSO-$d_6$) δ1.55-1.82 (1H, m), 2.03 (1H, dd, J=12.8, 4.9 Hz), 2.39 (3H, s), 2.75 (3H, s), 3.48 (1H, t, J=11.7 Hz), 3.58 (1H, t, J=11.0 Hz), 3.89 (3H, s), 3.95 (2H, dd, J=10.7, 4.4 Hz), 4.20-4.27 (1H, m), 4.30 (2H, s), 4.82 (1H, td, J=10.2, 4.8 Hz), 5.17 (1H, d, J=5.1 Hz), 6.75 (1H, d, J=2.3 Hz), 7.51 (1H, dd, J=8.2, 2.2 Hz), 7.74 (1H, d, J=2.1 Hz), 7.82 (1H, d, J=8.1 Hz), 7.93 (1H, s), 8.45 (1H, d, J=1.5 Hz).

Example 59

3-((1S,2S)-2-hydroxycyclohexyl)-7,8-dimethyl-6-((6-(1-methyl-1H-pyrazol-4-yl)pyridin-3-yl)methyl)quinazolin-4(3H)-one To a mixture of 6-((6-chloropyridin-3-yl)methyl)-3-((1S,2S)-2-hydroxycyclohexyl)-7,8-dimethylquinazolin-4(3H)- one (0.10 g), 1-methyl-4-(4,4,5,5-tetramethyl-1,3,2-dioxaborolan-2-yl)-1H-pyrazole (0.06 g), 2 M aqueous sodium carbonate solution (0.25 mL) and DME (3.0 mL) was added tetrakis(triphenylphosphine)palladium(0) (0.01 g) under an argon atmosphere and the mixture was stirred at 90° C. overnight. The reaction mixture was dried over anhydrous sodium sulfate and concentrated under reduced pressure. The residue was purified by silica gel column chromatography (ethyl acetate/hexane, thereafter methanol/ethyl acetate) and triturated with ethyl acetate to give the title compound (0.01 g)

$^1$H NMR (300 MHz, DMSO-d$_6$) δ1.24-1.39 (3H, m), 1.66-1.84 (4H, m), 2.00-2.05 (1H, m), 2.30 (3H, s), 2.52 (3H, s), 3.87 (3H, s), 3.89-4.02 (1H, m), 4.15 (2H, s), 4.20-4.51 (1H, m), 4.88 (1H, d, J=5.5 Hz), 7.40-7.48 (1H, m), 7.51-7.58 (1H, m), 7.79 (1H, s), 7.93 (1H, s), 8.21 (1H, s), 8.33-8.40 (2H, m).

The compounds of Examples 1-6, 8-12, 14, 15, 17, 22, 23, 38-43, 47 and 49-59 in Table 1 were produced by the methods shown in the above-mentioned Examples, and the compounds of Examples 7, 13, 16, 18-21, 24-28, 30-32, 34-37, 44-46 and 48 in Table 1 were produced by the methods shown in the above-mentioned production methods or Examples or a method analogous thereto. Example compounds are shown in Table 1. In the Tables, MS means measured values.

TABLE 1-1

| Ex. No. | IUPAC name | structural formula | salt | MS |
|---|---|---|---|---|
| 1 | 3-(trans-2-hydroxycyclohexyl)-7,8-dimethyl-6-(4-(1H-pyrazol-1-yl))benzyl)quinaolin-4(3H)-one | | | 429.2 |
| 2 | 3-(trans-2-hydroxycyclopentyl)-7,8-dimethyl-6-(4-(1H-pyrazol-1-yl)benzyl)quinazolin-4(3H)-one | | | 415.2 |
| 3 | 3-(trans-4-hydroxytetrahydro-2H-pyran-3-yl)-7,8-dimethyl-6-(4-(1H-pyrazol-1-yl)benzyl)quinazolin-4(3H)-one synonym: 1,5-anhydro-2,4-dideoxy-2-(7,8-dimethyl-4-oxo-6-(4-(1H-pyrazol-1-yl)benzyl)quinazolin-3(4H)-yl)-threo-pentitol | | | 431.2 |

TABLE 1-1-continued

| Ex. No. | IUPAC name | structural formula | salt | MS |
|---|---|---|---|---|
| 4 | 7,8-dimethyl-6-(4-(1H-pyrazol-1-yl)benzyl)-3-(tetrahydrofuran-2-ylmethyl)quinazolin-4(3H)-one | | | 415.2 |
| 5 | 7,8-dimethyl-6-(4-(1H-pyrazol-1-yl)benzyl)quinazolin-4(3H)-one | | | 331.2 |
| 6 | 2-(7,8-dimethyl-4-oxo-6-(4-(1H-pyrazol-1-yl)benzyl)quinazolin-3(4H)-yl)-3-fluorobenzonitrile | | | 450.1 |

TABLE 1-1-continued
| Ex. No. | IUPAC name | structural formula | salt | MS |
|---|---|---|---|---|
| 7 | 3-(7,8-dimethyl-4-oxo-6-(4-(1H-pyrazol-1-yl)benzyl)quinazolin-3(4H)-yl)pyridine-2-carbonitrile | 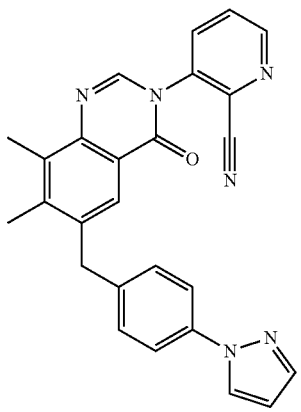 [SMILES: Cc1c(Cc2ccc(-n3cccn3)cc2)cc2c(=O)n(-c3cccnc3C#N)cnc2c1C] | | 433.1 |
| 8 | 3,7,8-trimethyl-6-(4-(1H-pyrazol-1-yl)benzyl)quinazolin-4(3H)-one | 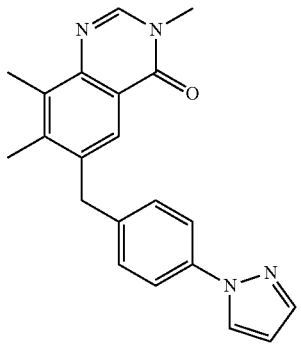 [SMILES: Cc1c(Cc2ccc(-n3cccn3)cc2)cc2c(=O)n(C)cnc2c1C] | | 345.2 |
| 9 | 1-((3-(trans-2-hydroxycyclopentyl)-7,8-dimethyl-4-oxo-3,4-dihydroquinazolin-6-yl)methyl)-4-(pyridin-2-yl)piperidine-4-carbonitrile | 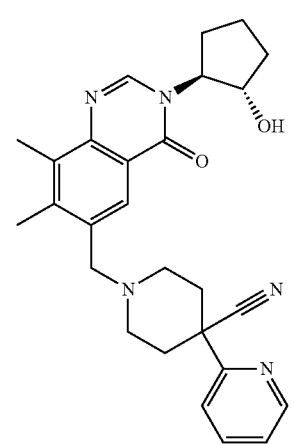 [SMILES: Cc1c(CN2CCC(C#N)(c3ccccn3)CC2)cc2c(=O)n([C@H]3CCC[C@@H]3O)cnc2c1C] | | 458.2 |

TABLE 1-1-continued

| Ex. No. | IUPAC name | structural formula | salt | MS |
|---|---|---|---|---|
| 10 | 3-(trans-2-hydroxycyclopentyl)-7,8-dimethyl-6-(4-(1-methyl-1H-pyrazol-3-yl)benzyl)quinazolin-4(3H)-one | | | 429.2 |
| 11 | 3-(trans-2-hydroxycyclopentyl)-7,8-dimethyl-6-(4-(1-methyl-1H-1,2,3-triazol-4-yl)benzyl)quinazolin-4(3H)-one | | | 430.2 |
| 12 | 3-(trans-2-hydroxycyclopentyl)-7,8-dimethyl-6-((2'-methyl-2,4'-bipyridin-5-yl)methyl)quinazolin-4(3H)-one | | | 441.2 |

TABLE 1-1-continued

| Ex. No. | IUPAC name | structural formula | salt | MS |
|---|---|---|---|---|
| 13 | 3-trans-2-hydroxycyclopentyl)-8-methyl-6-(4-(1H-pyrazol-1-yl)benzyl)quinazolin-4(3H)-one | | | 401.1 |
| 14 | 3-(trans-2-hydroxycyclopentyl)-7,8-dimethyl-6-((6-(1-methyl-1H-1,2,3-triazol-4-yl)pyridin-3-yl)methyl)quinazolin-4(3H)-one | | | 431.1 |
| 15 | 3-(trans-2-hydroxycyclopentyl)-7,8-dimethyl-6-((6-(1-methyl-1H-pyrazol-4-yl)pyridin-3-yl)methyl)quinazolin-4(3H)-one | | | 430.2 |

TABLE 1-1-continued

| Ex. No. | IUPAC name | structural formula | salt | MS |
|---|---|---|---|---|
| 16 | 7-chloro-3-(trans-2-hydroxycyclopentyl)-6-(4-(1H-pyrazol-1-yl)benzyl)quinazolin-4(3H)-one | | | 421.1 |
| 17 | 3-(trans-2-hydroxycyclopentyl)-7,8-dimethyl-6-(4-(1-methyl-1H-pyrazol-4-yl)benzyl)quinazolin-4(3H)-one | | | 429.1 |
| 18 | 3-(trans-2-hydroxycyclopentyl)-7-methoxy-6-(4-(1-methyl-1H-pyrazol-4-yl)benzyl)quinazolin-4(3H)-one | | | 431.1 |
| 19 | 6-((6-chloropyridin-3-yl)methyl)-3-(trans-2-hydroxycyclohexyl)-7,8-dimethylquinazolin-4(3H)-one | | | 398.1 |

TABLE 1-1-continued
| Ex. No. | IUPAC name | structural formula | salt | MS |
|---|---|---|---|---|
| 20 | 3-(trans-2-hydroxycyclopentyl)-8-methoxy-6-(4-(1-methyl-1H-pyrazol-4-yl)benzyl)quinazolin-4(3H)-one | 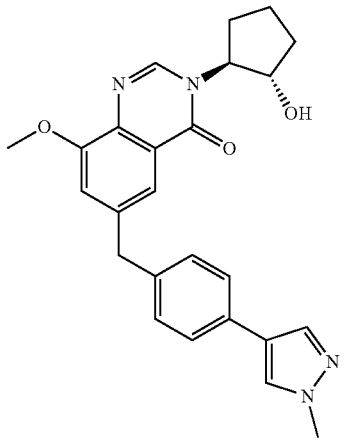 [SMILES: COc1cc(Cc2ccc(-c3cnn(C)c3)cc2)cc2c(=O)n([C@H]3CCC[C@@H]3O)cnc12] | | 431.1 |
| 21 | 3-(trans-2-hydroxycyclopentyl)-7-methyl-6-(4-(1-methyl-1H-1,2,3-triazol-4-yl)benzyl)quinazolin-4(3H)-one | 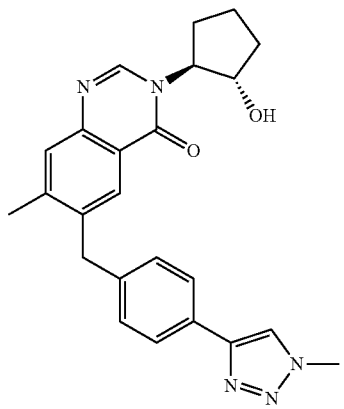 | | 416.1 |
| 22 | 3-(trans-2-hydroxycyclopentyl)-7,8-dimethyl-6-(4-(1-methyl-1H-1,2,3-triazol-4-yl)benzyl)quinazolin-4(3H)-one (optical isomer: retention time short) | 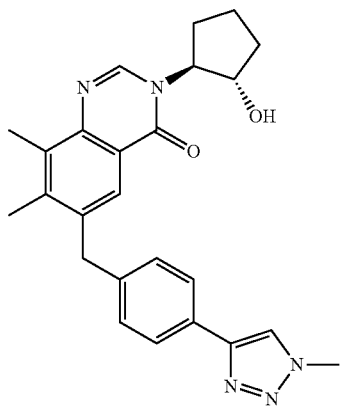 | | 430.1 |

TABLE 1-1-continued

| Ex. No. | IUPAC name | structural formula | salt | MS |
|---|---|---|---|---|
| 23 | 3-(trans-2-hydroxycyclopentyl)-7,8-dimethyl-6-(4-(1-methyl-1H-1,2,3-triazol-4-yl)benzyl)quinazolin-4(3H)-one (optical isomer: retention time long) | | | 430.1 |
| 24 | 8-methoxy-7-methyl-6-((6-(1-methyl-1H-pyrazol-4-yl)pyridin-3-yl)methyl)-3-(tetrahydrofuran-2-ylmethyl)quinazolin-4(3H)-one hydrochloride | | HCl | 446.2 |
| 25 | 8-chloro-7-methyl-6-((6-(1-methyl-1H-pyrazo-4-yl)pyridin-3-yl)methyl)-3-(tetrahydrofuran-2-ylmethyl)quinazolin-4(3H)-one hydrochloride | | HCl | 450.0 |
| 26 | 3-(trans-2-hydroxycyclohexyl)-6-(4-methoxybenzyl)-7,8-dimethylquinazolin-4(3H)-one | | | 393.2 |

TABLE 1-1-continued

| Ex. No. | IUPAC name | structural formula | salt | MS |
|---|---|---|---|---|
| 27 | 6-(3-(difluoromethoxy)benzyl)-3-(trans-2-hydroxycyclohexyl)-7,8-dimethylquinazolin-4(3H)-one | | | 429.1 |
| 28 | 3-fluoro-4-((3-(trans-2-hydroxycyclohexyl)-7,8-dimethyl-4-oxo-3,4-dihydroquinazolin-6-yl)methyl)benzonitrile | | | 406.1 |
| 30 | 4-fluooro-2-((3-(trans-2-hydroxycyclohexyl)-7,8-dimethyl-4-oxo-3,4-dihydroquinazolin-6-yl)methyl)benzonitrile | | | 406.1 |

TABLE 1-1-continued

| Ex. No. | IUPAC name | structural formula | salt | MS |
|---|---|---|---|---|
| 31 | 3-((3-(trans-2-hydroxycyclohexyl)-7,8-dimethyl-4-oxo-3,4-dihydroquinazolin-6-yl)methyl)benzonitrile | | | 388.1 |
| 32 | 6-((3,5-dimethyl-1,2-oxazol-4-yl)methyl)-3-(trans-2-hydroxycyclohexyl)-7,8-dimethylquinazolin-4(3H)-one | | | 382.1 |
| 34 | 3-(trans-2-hydroxycyclohexyl)-7,8-dimethyl-6-((1-methyl-1H-pyrazol-3-yl)methyl)quinazolin-4(3H)-one | | | 367.1 |
| 35 | 3-(trans-2-hydroxycyclohexyl)-7,8-dimethyl-6-((6-methylpyridin-3-yl)methyl)quinazolin-4(3H)-one | | | 378.2 |

TABLE 1-1-continued

| Ex. No. | IUPAC name | structural formula | salt | MS |
|---|---|---|---|---|
| 36 | 6-((2-chloropyridin-4-yl)methyl)-3-(trans-2-hydroxycyclohexyl)-7,8-dimethylquinazolin-4(3H)-one | 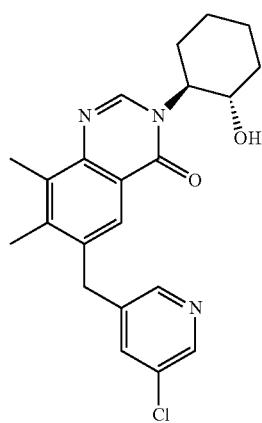 [SMILES: Cc1c(Cc2cncc(Cl)c2)cc2c(=O)n([C@H]3CCCC[C@@H]3O)cnc2c1C] | | 398.1 |
| 37 | 3-trans-2-hydroxycyclopentyl)-8-methoxy-7-methyl-6-((6-(1H-pyrazol-1-yl)pyridin-3-yl)methyl)quinazolin-4(3H)-one | 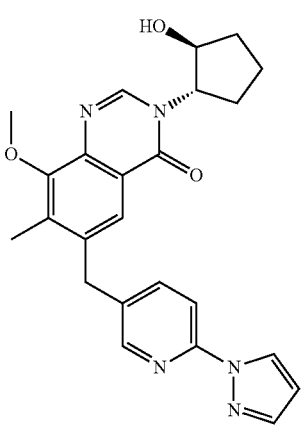 [SMILES: COc1c(C)c(Cc2ccc(-n3cccn3)nc2)cc2c(=O)n([C@H]3CCC[C@@H]3O)cnc12] | | 432.0 |
| 38 | 8-fluoro-3-((3S,4S)-4-hydroxytetrahydro-2H-pyran-3-yl)-7-methyl-6-(4-(1H-pyrazol-1-yl)benzyl)quinazolin-4(3H)-one synonym: 1,5-anhydro-2,4-dideoxy-2-(8-fluoro-7-methyl-4-oxo-6-(4-(1H-pyrazol-1-yl)benzyl)quinazolin-3(4H)-yl)-L-threo-pentitol | 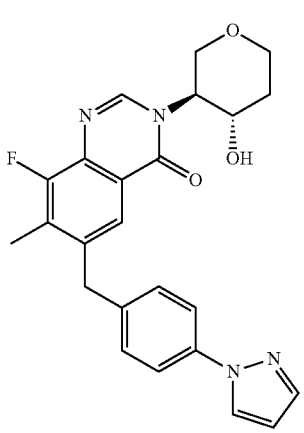 [SMILES: Cc1c(Cc2ccc(-n3cccn3)cc2)cc2c(=O)n([C@H]3COCC[C@@H]3O)cnc2c1F] | | 435.2 |

TABLE 1-1-continued

| Ex. No. | IUPAC name | structural formula | salt | MS |
|---|---|---|---|---|
| 39 | 7,8-dimethyl-6-((6-(1-methyl-1H-pyrazol-4-yl)pyridin-3-yl)methyl)-3-(tetrahydrofuran-2-ylmethyl)-1,2,3-benzotriazin-4(3H)-one | 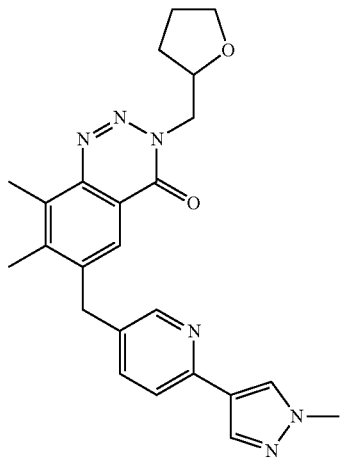 | | 431.1 |
| 40 | 3-(trans-2-hydroxycyclopentyl)-7,8-dimethyl-6-(4-(1-methyl-1H-1,2,3-triazol-4-yl)benzyl)-1,2,3-benzotriazin-4(3H)-one | 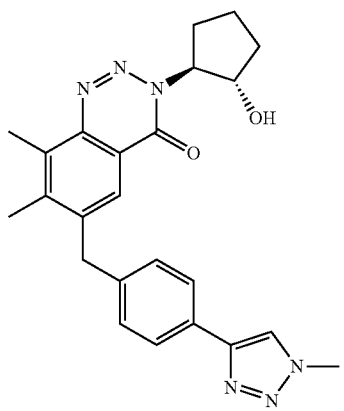 | | 431.4 |
| 41 | 3-((3S,4S)-4-hydroxytetrahydro-2H-pyran-3-yl)-7,8-dimethyl-6-(4-(1H-pyrazol-1-yl)benzyl)-1,2,3-benzotriazin-4(3H)-one synonym: 1,5-anhydro-2,4-dideoxy-2-(7,8-dimethyl-4-oxo-6-(4-(1H-pyrazol-1-yl)benzyl)-1,2,3-benzotriazin-3(4H)-yl)-threo-pentitol | 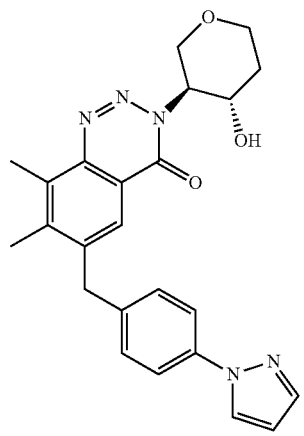 [SMILES: Cc1c(Cc2ccc(-n3cccn3)cc2)cc2c(=O)n([C@H]3COCC[C@@H]3O)nnc2c1C] | | 432.1 |

TABLE 1-1-continued

| Ex. No. | IUPAC name | structural formula | salt | MS |
|---|---|---|---|---|
| 42 | 3-(trans-4-hydroxytetrahydro-2H-pyran-3-yl)-6-((6-(1H-imidazol-1-yl)pyridin-3-yl)methyl)-7,8-dimethyl-1,2,3-benzotriazin-4(3H)-one<br>synonym: 1,5-anhydro-2,4-dideoxy-2-(6-((6-(1H-imidazol-1-yl)pyridin-3-yl)methyl)-7,8-dimethyl-4-oxo-1,2,3-benzotriazin-3(4H)-yl)-threo-pentitol | | | 433.1 |
| 43 | 3-((3S,4S)-4-hydroxytetrahydro-2H-pyran-3-yl)-7,8-dimethyl-6-(4-(1H-pyrazol-1-yl)benzyl)-1,2,3-benzotriazin-4(3H)-one<br>synonym: 1,5-anhydro-2,4-dideoxy-2-(7,8-dimethyl-4-oxo-6-(4-(1H-pyrazol-1-yl)benzyl)-1,2,3-benzotriazin-3(4H)-yl)-L-threo-pentitol | | | 432.1 |
| 44 | 3-[(3S,4S)-4-hydroxytetrahydro-2H-pyran-3-yl]-7,8-dimethyl-6-{[6-(1H-pyrazol-1-yl)pyridin-3-yl]methyl}-1,2,3-benzotriazin-4(3H)-one<br>synonym: 1,5-anhydro-2,4-dideoxy-2-(7,8-dimethyl-4-oxo-6-((6-(1H-pyrazol-1-yl)pyridin-3-yl)methyl)-1,2,3-benzotriazin-3(4H)-yl)-L-threo-pentitol | | | 433.1 |

TABLE 1-1-continued

| Ex. No. | IUPAC name | structural formula | salt | MS |
|---|---|---|---|---|
| 45 | 8-chloro-7-methyl-6-((6-(1-methyl-1H-pyrazol-3-yl)pyridin-3-yl)methyl)-3-(tetrahydrofuran-2-ylmethyl)1,2,3-benzotriazin-4(3H)-one | | | 451.1 |
| 46 | 3-(trans-4-hydroxytetrahydro-2H-pyran-3-yl)-7,8-dimethyl-6-(4-(1-methyl-1H-pyrazol-3-yl)benzyl)-1,2,3-benzotriazin-4(3H)-one<br>synonym: 1,5-anhydro-2,4-dideoxy-2-(7,8-dimethyl-6-(4-(1-methyl-1H-pyrazol-3-yl)benzyl)-4-oxo-1,2,3-benzotriazin-3(4H)-yl)-threo-pentitol | | | 446.1 |
| 47 | 3-((3S,4S)-4-hydroxytetrahydro-2H-pyran-3-yl)-7,8-dimethyl-6-(4-(1-methyl-1H-pyrazol-3-yl)benzyl)-1,2,3-benzotriazin-4(3H)-one<br>synonym: 1,5-anhydro-2,4-dideoxy-2-(7,8-dimethyl-6-(4-(1-methyl-1H-pyrazol-3-yl)benzyl)-4-oxo-1,2,3-benzotriazin-3(4H)-yl)-L-threo-pentitol | | | 446.0 |

TABLE 1-1-continued

| Ex. No. | IUPAC name | structural formula | salt | MS |
|---|---|---|---|---|
| 48 | 3-((3S,4S)-4-hydroxytetrahydro-2H-pyran-3-yl)-7-methyl-6-(4-(1-methyl-1H-pyrazol-3-yl)benzyl)-1,2,3-benzotriazin-4(3H)-one synonym: 1,5-anhydro-2,4-dideoxy-2-(7-methyl-6-(4-(1-methyl-1H-pyrazol-3-yl)benzyl)-4-oxo-1,2,3-benzotriazin-3(4H)-yl)-L-threo-pentitol | | | 432.1 |
| 49 | 8-fluoro-3-((3S,4S)-4-hydroxytetrahydro-2H-pyran-3-yl)-7-methyl-6-(4-(1H-pyrazol-1-yl)benzyl)-1,2,3-benzotriazin-4(3H)-one synonym: 1,5-anhydro-2,4-dideoxy-2-(8-fluoro-7-methyl-4-oxo-6-(4-(1H-pyrazol-1-yl)benzyl)-1,2,3-benzotriazin-3(4H)-yl)-L-threo-pentitol | | | 436.2 |
| 50 | 3-(trans-2-hydroxycyclopentyl)-7,8-dimethyl-6-((6-(1-methyl-1H-pyrazol-4-yl)pyridin-3-yl)methyl)quinazolin-4(3H)-one (optical isomer: retention time short) | | | 430.2 |

TABLE 1-1-continued

| Ex. No. | IUPAC name | structural formula | salt | MS |
|---|---|---|---|---|
| 51 | 3-(trans-2-hydroxycyclopentyl)-7,8-dimethyl-6-((6-(1-metthyl-1H-pyrazol-4-yl)pyridin-3-yl)methyl)quinazolin-4(3H)-one (optical isomer: retention time long) | | | 430.2 |
| 52 | 3-(trans-4-hydroxytetrahydro-2H-pyran-3-yl)-7,8-dimethyl-6-(4-(1H-pyrazol-1-yl)benzyl)quinazolin-4(3H)-one synonym: 1,5-anhydro-2,4-dideoxy-2-(7,8-dimethyl-4-oxo-6-(4-(1H-pyrazol-1-yl)benzyl)quinazolin-3(4H)-yl)-threo-pentitol (optical isomer: retention time short) | | | 431.2 |
| 53 | 3-(trans-4-hydroxytetrahydro-2H-pyran-3-yl)-7,8-dimethyl-6-(4-(1H-pyrazol-1-yl)benzyl)quinazolin-4(3H)-one synonym: 1,5-anhydro-2,4-dideoxy-2-(7,8-dimethyl-4-oxo-6-(4-(1H-pyrazol-1-yl)benzyl)quinazolin-3(4H)-yl)-threo-pentitiol (optical isomer: retention time long) | | | 431.3 |

TABLE 1-1-continued

| Ex. No. | IUPAC name | structural formula | salt | MS |
|---|---|---|---|---|
| 54 | 6-((6-chloropyridin-3-yl)methyl)-3-((1S,2S)-2-hydroxycyclohexyl)-7,8-dimethylquinazolin-4(3H)-one | | | 398.4 |
| 55 | 3-((3R,4S)-3-hydroxytetrahydro-2H-pyran-4-yl)-7,8-dimethyl-6-(4-(1H-pyrazol-1-yl)benzyl)quinazolin-4-(3H)-one synonym: 1,5-anhydro-2,3-dideoxy-3-(7,8-dimethyl-4-oxo-6-(4-(1H-pyrazol-1-yl)benzyl)quinazolin-3(4H)-yl)-L-threo-pentitol | | | 431.2 |
| 56 | 3-((3R,4S)-3-hydroxytetrahydro-2H-pyran-4-yl)-7,8-dimethyl-6-(4-(1H-pyrazol-1-yl)benzyl)-1,2,3-benzotriazin-4(3H)-one synonym: 1,5-anhydro-2,3-dideoxy-3-(7,8-dimethyl-4-oxo-6-(4-(1H-pyrazol-1-yl)benzyl)-1,2,3-benzotriazin-3(4H)-yl)-L-threo-pentitol | | | 432.2 |
| 57 | 3-((1S,2S)-2-hydroxycyclohexyl)-7,8-dimethyl-6-((6-(1-methyl-1H-pyrazol-3-yl)pyridin-3-yl)methyl)quinazolin-4(3H)-one | | | 444.3 |

TABLE 1-1-continued

| Ex. No. | IUPAC name | structural formula | salt | MS |
|---|---|---|---|---|
| 58 | 3-((3S,4S)-4-hydroxytetrahydro-2H-pyran-3-yl)-7,8-dimethyl-6-((6-(1-methyl-1H-pyrazol-3-yl)pyridin-3-yl)methyl)-1,2,3-benzotriazin-4(3H)-one synonym: 1,5-anhydro-2,4-dideoxy-2-(7,8-dimethyl-6-((6-(1-methyl-1H-pyrazol-3-yl)pyridin-3-yl)methyl)-4-oxo-1,2,3-benzotriazin-3(4H)-yl)-L-threo-pentitol | | | 447.1 |
| 59 | 3-((1S,2S)-2-hydroxycyclohexyl)-7,8-dimethyl-6-((6-(1-methyl-1H-pyrazol-4-yl)pyridin-3-yl)methyl)quinazolin-4(3H)-one | | | 444.3 |

Formulation Example 1

| (1) | compound obtained in Example 1 | 10.0 g |
|---|---|---|
| (2) | Lactose | 60.0 g |
| (3) | Cornstarch | 35.0 g |
| (4) | Gelatin | 3.0 g |
| (5) | Magnesium stearate | 2.0 g |

A mixture of the compound (10.0 g) obtained in Example 1, lactose (60.0 g) and cornstarch (35.0 g) is granulated by passing through a 1 mm mesh sieve while using 10 wt % aqueous gelatin solution (30 mL) (3.0 g as gelatin) and the granules are dried at 40° C. and sieved again. The obtained granules are mixed with magnesium stearate (2.0 g) and the mixture is compressed. The obtained core tablets are coated with a sugar coating of an aqueous suspension of saccharose, titanium dioxide, talc and gum arabic. The coated tablets are glazed with beeswax to give 1000 coated tablets.

Formulation Example 2

| (1) | compound obtained in Example 1 | 10.0 g |
|---|---|---|
| (2) | Lactose | 70.0 g |
| (3) | Cornstarch | 50.0 g |
| (4) | Soluble starch | 7.0 g |
| (5) | Magnesium stearate | 3.0 g |

The compound (10.0 g) obtained in Example 1 and magnesium stearate (3.0 g) are granulated using aqueous soluble starch solution (70 mL) (7.0 g as soluble starch), and the obtained granules are dried, and mixed with lactose (70.0 g) and cornstarch (50.0 g). The mixture is compressed to give 1000 tablets.

Experimental Example 1

Measurement of M1 receptor positive allosteric modulator (M1PAM) activity

The activity of a test compound in the presence of acetylcholine at EC20 concentration (final concentration 0.8 nM), which affords an action corresponding to about 20% of the maximum activity, was measured as PAM activity. The method is as follows. CHO-K1 cells stably expressing a human M1 receptor (hCHRM1) were plated on a 384-well black clear bottom plate (BD Falcon) at 5,000 cells/well, and cultured in an incubator at 37° C., 5% $CO_2$ for 1 day. The medium in the cell plate was removed, and assay buffer A containing a calcium indicator (Recording medium (DOJINDO LABORATORIES), 0.1% BSA (Wako Pure Chemical Industries, Ltd.), 2.5 µg/mL Fluo-4 AM (DOJINDO LABORATORIES), 0.08% Pluronic F127 (DOJINDO LABORATORIES) and 1.25 mM probenecid (DOJINDO LABORATORIES) were added at 30 µL/well. The cells were left standing in the incubator at 37° C., 5% $CO_2$ for 30 min, and further left standing at room temperature for 30 min. A test compound prepared by diluting with assay buffer B (HESS (Invitrogen), 20 mM HEPES (Invitrogen), 0.1% BSA) containing 3.2 nM acetylcholine was added at 10 µL/well, and the fluorescence was measured by FDSS/µcell (Hamamatsu Photonics K.K.) for 1 min every for 1 second. With the definition that the amount of change in the fluorescence on addition of acetylcholine (final concentration 1 µM) is 100% and that on addition of DMSO instead of a test compound is 0%, the activity (%) of the test compound was calculated, and the inflection point in the concentration-dependent curve of the test compound was calculated as IP values. The results are shown in Table 2.

TABLE 2

| Ex. No. | IP value (nM) | activity (%) at 10 µM |
|---|---|---|
| 1 | 52 | 92 |
| 2 | 61 | 96 |
| 3 | 15 | 98 |
| 11 | 15 | 101 |
| 12 | 39 | 99 |
| 14 | 11 | 100 |
| 15 | 11 | 100 |
| 17 | 55 | 90 |
| 19 | 66 | 97 |
| 20 | 61 | 97 |
| 21 | 51 | 97 |
| 22 | 79 | 95 |
| 23 | 13 | 88 |
| 25 | 62 | 95 |
| 35 | 41 | 96 |
| 38 | 17 | 100 |
| 39 | 85 | 97 |
| 40 | 70 | 94 |
| 41 | 29 | 101 |
| 42 | 31 | 100 |
| 43 | 14 | 100 |
| 44 | 32 | 100 |
| 45 | 25 | 95 |
| 46 | 32 | 97 |
| 47 | 38 | 95 |
| 48 | 59 | 98 |
| 49 | 18 | 97 |
| 50 | 6.5 | 102 |
| 51 | 79 | 97 |
| 52 | 6.0 | 98 |
| 54 | 23 | 96 |
| 55 | 7.4 | 99 |
| 56 | 15 | 98 |
| 57 | 7.3 | 98 |
| 58 | 14 | 95 |
| 59 | 4.8 | 94 |

As shown in Table 2, the compound of the present invention has a superior cholinergic muscarine M1 receptor positive allosteric modulator activity.

INDUSTRIAL APPLICABILITY

The compound of the present invention may be useful as a cholinergic muscarinic M1 receptor positive allosteric modulator, or a medicament such as an agent for the prophylaxis or treatment of Alzheimer's disease, schizophrenia, pain, sleep disorder, Parkinson's disease dementia, Lewy body dementia and the like.

This application is based on a patent application No. 2015-206780 filed in Japan (filing date: Oct. 20, 2015), the entire contents of which are incorporated by reference herein.

The invention claimed is:
1. A compound represented by the formula:

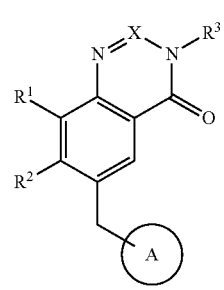

wherein
$R^1$ is a hydrogen atom, a halogen atom, a $C_{1-6}$ alkyl group or a $C_{1-6}$ alkoxy group;
$R^2$ is a hydrogen atom, a halogen atom, a $C_{1-6}$ alkyl group or a $C_{1-6}$ alkoxy group;
$R^3$ is
(1) a hydrogen atom,
(2) a $C_{1-6}$ alkyl group optionally substituted by 1 to 3 substituents selected from 3- to 14-membered non-aromatic heterocyclic groups,
(3) a 3- to 14-membered non-aromatic heterocyclic group optionally substituted by 1 to 3 hydroxy groups,
(4) a 5- to 14-membered aromatic heterocyclic group optionally substituted 1 to 3 cyano groups,
(5) a $C_{3-10}$ cycloalkyl group optionally substituted by 1 to 3 hydroxy groups, or
(6) a $C_{6-14}$ aryl group optionally substituted by 1 to 3 substituents selected from
    (a) a halogen atom, and
    (b) a cyano group;
ring A is
(1) a benzene ring optionally further substituted by 1 to 3 substituents selected from
    (a) a halogen atom,
    (b) a cyano group,
    (c) a $C_{1-6}$ alkoxy group optionally substituted by 1 to 5 halogen atoms, and
    (d) a 5- to 14-membered aromatic heterocyclic group optionally substituted by 1 to 3 $C_{1-6}$ alkyl groups,
(2) a 5- or 6-membered monocyclic aromatic heterocycle optionally further substituted by 1 to 3 substituents selected from
    (a) a halogen atom,
    (b) a $C_{1-6}$ alkyl group, and
    (c) a 5- to 14-membered aromatic heterocyclic group optionally substituted by 1 to 3 $C_{1-6}$ alkyl groups, or
(3) a 4- to 6-membered monocyclic non-aromatic heterocycle optionally further substituted by 1 to 3 substituents selected from
    (a) a cyano group, and
    (b) a 5- to 14-membered aromatic heterocyclic group; and
X is CH or N,
or a salt thereof.
2. The compound according to claim 1, wherein
$R^1$ is a hydrogen atom, a halogen atom, a $C_{1-6}$ alkyl group or a $C_{1-6}$ alkoxy group;
$R^2$ is a hydrogen atom, a halogen atom, a $C_{1-6}$ alkyl group or a $C_{1-6}$ alkoxy group;
when one of $R^1$ and $R^2$ is a hydrogen atom, then the other is other than a hydrogen atom;

R³ is
(1) a hydrogen atom,
(2) a C$_{1-6}$ alkyl group optionally substituted by 1 to 3 substituents selected from 3- to 14-membered non-aromatic heterocyclic groups,
(3) a 3- to 14-membered non-aromatic heterocyclic group optionally substituted by 1 to 3 hydroxy groups,
(4) a 5- to 14-membered aromatic heterocyclic group optionally substituted 1 to 3 cyano groups,
(5) a C$_{3-10}$ cycloalkyl group optionally substituted by 1 to 3 hydroxy groups, or
(6) a C$_{6-14}$ aryl group optionally substituted by 1 to 3 substituents selected from
  (a) a halogen atom, and
  (b) a cyano group;
ring A is
(1) a benzene ring optionally further substituted by 1 to 3 substituents selected from
  (a) a halogen atom,
  (b) a cyano group,
  (c) a C$_{1-6}$ alkoxy group optionally substituted by 1 to 5 halogen atoms, and
  (d) a 5- to 14-membered aromatic heterocyclic group optionally substituted by 1 to 3 C$_{1-6}$ alkyl groups,
(2) a 5- or 6-membered monocyclic aromatic heterocycle optionally further substituted by 1 to 3 substituents selected from
  (a) a halogen atom,
  (b) a C$_{1-6}$ alkyl group, and
  (c) a 5- to 14-membered aromatic heterocyclic group optionally substituted by 1 to 3 C$_{1-6}$ alkyl groups, or
(3) a 4- to 6-membered monocyclic non-aromatic heterocycle optionally further substituted by 1 to 3 substituents selected from
  (a) a cyano group, and
  (b) a 5- to 14-membered aromatic heterocyclic group; and
X is CH or N,
or a salt thereof.

3. The compound according to claim 1, wherein
R¹ is a hydrogen atom, a halogen atom or a C$_{1-6}$ alkyl group;
R² is a C$_{1-6}$ alkyl group;
R³ is
(1) a C$_{1-6}$ alkyl group optionally substituted by 1 to 3 substituents selected from 3- to 14-membered non-aromatic heterocyclic groups,
(2) a 3- to 14-membered non-aromatic heterocyclic group optionally substituted by 1 to 3 hydroxy groups, or
(3) a C$_{3-10}$ cycloalkyl group optionally substituted by 1 to 3 hydroxy groups;
ring A is
(1) a benzene ring optionally further substituted by 1 to 3, 5- to 14-membered aromatic heterocyclic groups optionally substituted by 1 to 3 C$_{1-6}$ alkyl groups,
(2) a 5- or 6-membered monocyclic aromatic heterocycle optionally further substituted by 1 to 3 substituents selected from
  (a) a halogen atom, and
  (b) a 5- to 14-membered aromatic heterocyclic group optionally substituted by 1 to 3 C$_{1-6}$ alkyl groups, or
(3) a 4- to 6-membered monocyclic non-aromatic heterocycle optionally further substituted by 1 to 3 substituents selected from
  (a) a cyano group, and
  (b) a 5- to 14-membered aromatic heterocyclic group; and
X is CH or N,
or a salt thereof.

4. The compound according to claim 1, wherein
R¹ is a halogen atom or a C$_{1-6}$ alkyl group;
R² is a C$_{1-6}$ alkyl group;
R³ is
(1) a 3- to 14-membered non-aromatic heterocyclic group optionally substituted by 1 to 3 hydroxy groups, or
(2) a C$_{3-10}$ cycloalkyl group optionally substituted by 1 to 3 hydroxy groups;
ring A is
(1) a benzene ring optionally further substituted by 1 to 3, 5- to 14-membered aromatic heterocyclic groups optionally substituted by 1 to 3 C$_{1-6}$ alkyl groups, or
(2) a 5- or 6-membered monocyclic aromatic heterocycle optionally further substituted by 1 to 3, 5- to 14-membered aromatic heterocyclic groups optionally substituted by 1 to 3 C$_{1-6}$ alkyl groups; and
X is CH or N,
or a salt thereof.

5. 8-Fluoro-3-((3S,4S)-4-hydroxytetrahydro-2H-pyran-3-yl)-7-methyl-6-(4-(1H-pyrazol-1-yl)benzyl)quinazolin-4(3H)-one, or a salt thereof.

6. 3-((3S,4S)-4-Hydroxytetrahydro-2H-pyran-3-yl)-7,8-dimethyl-6-(4-(1-methyl-1H-pyrazol-3-yl)benzyl)-1,2,3-benzotriazin-4(3H)-one, or a salt thereof.

7. 3-((1S,2S)-2-Hydroxycyclohexyl)-7,8-dimethyl-6-((6-(1-methyl-1H-pyrazol-4-yl)pyridin-3-yl)methyl)quinazolin-4(3H)-one, or a salt thereof.

8. A pharmaceutical composition comprising the compound according to claim 1 or a salt thereof, and a pharmaceutically acceptable carrier.

9. A method of cholinergic muscarinic M1 receptor positive allosteric modulation in a mammal, which comprises administering an effective amount of the compound according to claim 1 or a salt thereof to the mammal.

10. The compound according to claim 2, wherein
R³ is
(1) a C$_{1-6}$ alkyl group substituted by 1 to 3 substituents selected from 3- to 14-membered non-aromatic heterocyclic groups,
(2) a 3- to 14-membered non-aromatic heterocyclic group optionally substituted by 1 to 3 hydroxy groups,
(3) a 5- to 14-membered aromatic heterocyclic group optionally substituted 1 to 3 cyano groups,
(4) a C$_{3-10}$ cycloalkyl group optionally substituted by 1 to 3 hydroxy groups, or
(5) a C$_{6-14}$ aryl group optionally substituted by 1 to 3 substituents selected from
  (a) a halogen atom, and
  (b) a cyano group; and
ring A is
(1) a benzene ring optionally further optionally substituted by 1 to 3 substituents selected from
  (a) a halogen atom,
  (b) a cyano group,
  (c) a C$_{1-6}$ alkoxy group optionally substituted by 1 to 5 halogen atoms, and
  (d) a 5- to 14-membered aromatic heterocyclic group optionally substituted by 1 to 3 C$_{1-6}$ alkyl groups, or
(2) a 5- or 6-membered monocyclic aromatic heterocycle optionally further substituted by 1 to 3 substituents selected from
  (a) a halogen atom,
  (b) a C$_{1-6}$ alkyl group, and
  (c) a 5- to 14-membered aromatic heterocyclic group optionally substituted by 1 to 3 C$_{1-6}$ alkyl groups,
or a salt thereof.

11. The compound according to claim 3, wherein
$R^3$ is
(1) a $C_{1-6}$ alkyl group substituted by 1 to 3 substituents selected from 3- to 14-membered non-aromatic heterocyclic groups,
(2) a 3- to 14-membered non-aromatic heterocyclic group optionally substituted by 1 to 3 hydroxy groups, or
(3) a $C_{3-10}$ cycloalkyl group optionally substituted by 1 to 3 hydroxy groups; and
ring A is
(1) a benzene ring optionally further substituted by 1 to 3, 5- to 14-membered aromatic heterocyclic groups optionally substituted by 1 to 3 $C_{1-6}$ alkyl groups, or (2) a 5- or 6-membered monocyclic aromatic heterocycle optionally further substituted by 1 to 3 substituents selected from
  (a) a halogen atom, and
  (b) a 5- to 14-membered aromatic heterocyclic group optionally substituted by 1 to 3 $C_{1-6}$ alkyl groups,
or a salt thereof.

* * * * *